United States Patent [19]
Mizuno et al.

[11] Patent Number: 5,876,325
[45] Date of Patent: Mar. 2, 1999

[54] SURGICAL MANIPULATION SYSTEM

[75] Inventors: Hitoshi Mizuno; Yuuichi Ikeda; Akihiro Horii; Shuichi Takayama; Akio Nakada; Naoki Uchiyama; Yasuhiro Ueda, all of Tokyo; Koichi Umeyama, Kasukabe; Sakae Takehana, Tokyo, all of Japan

[73] Assignee: Olympus Optical Co., Ltd., Tokyo, Japan

[21] Appl. No.: 940,613

[22] Filed: Sep. 30, 1997

Related U.S. Application Data

[63] Continuation of Ser. No. 316,833, Sep. 30, 1994.

[30] Foreign Application Priority Data

| Nov. 2, 1993 | [JP] | Japan | 5-274405 |
| Nov. 15, 1993 | [JP] | Japan | 5-285206 |
| Dec. 27, 1993 | [JP] | Japan | 5-348786 |
| Jun. 10, 1994 | [JP] | Japan | 6-128648 |
| Jun. 14, 1994 | [JP] | Japan | 6-131809 |
| Jun. 14, 1994 | [JP] | Japan | 6-131810 |
| Jun. 14, 1994 | [JP] | Japan | 6-131811 |

[51] Int. Cl.$^6$ ...................................................... A61B 1/00
[52] U.S. Cl. .......................... 600/102; 600/117; 600/118; 395/93
[58] Field of Search .................................... 600/102, 109, 600/117, 118; 395/93–96, 99, 82; 901/2, 3, 33, 34, 41, 44, 46

[56] References Cited

U.S. PATENT DOCUMENTS

| 3,923,166 | 12/1975 | Fletcher et al. | 901/2 |
| 4,604,016 | 8/1986 | Joyce | 414/7 |
| 4,837,734 | 6/1989 | Ichikawa et al. | 901/2 |
| 4,853,874 | 8/1989 | Iwanmoto et al. | 414/2 |
| 5,047,701 | 9/1991 | Takarada et al. | 901/9 |
| 5,105,367 | 4/1992 | Tsuchihashi et al. | 395/99 |
| 5,217,003 | 6/1993 | Wilk . | |
| 5,339,799 | 8/1994 | Kami et al. | 600/117 |
| 5,351,676 | 10/1994 | Putman | 600/117 |
| 5,410,638 | 4/1995 | Colgate et al. | 395/99 |
| 5,524,180 | 6/1996 | Wang et al. | 600/117 |
| 5,540,649 | 7/1996 | Bonnell et al. | 600/102 |

OTHER PUBLICATIONS

Taubes, Gary, "Surgery In Cyberspace", *Discover*, Dec. 1994, pp. 85–94.

International Encyclopedia of Robotics: Applications Automation, vol. 3, 1988. pp. 1710–1718 & Fisher, et al., Virtual Enivironment Display System, Oct. 1986, pp. 1–11.

*Primary Examiner*—John P. Leubecker
*Attorney, Agent, or Firm*—Frishauf, Holtz, Goodman, Langer & Chick

[57] ABSTRACT

A surgical manipulator system comprising at least one surgical manipulator, at least one guide, a detector, and a drive controller. The surgical manipulator has a surgical device for performing a desired operation. The guide guides the surgical device. The detector detects a position and/or orientation relationship between the surgical device and the guide, and/or a position and/or orientation relationship between the surgical device and another surgical device. The drive controller controls the surgical manipulator such that the surgical device is guided by the guide.

18 Claims, 45 Drawing Sheets

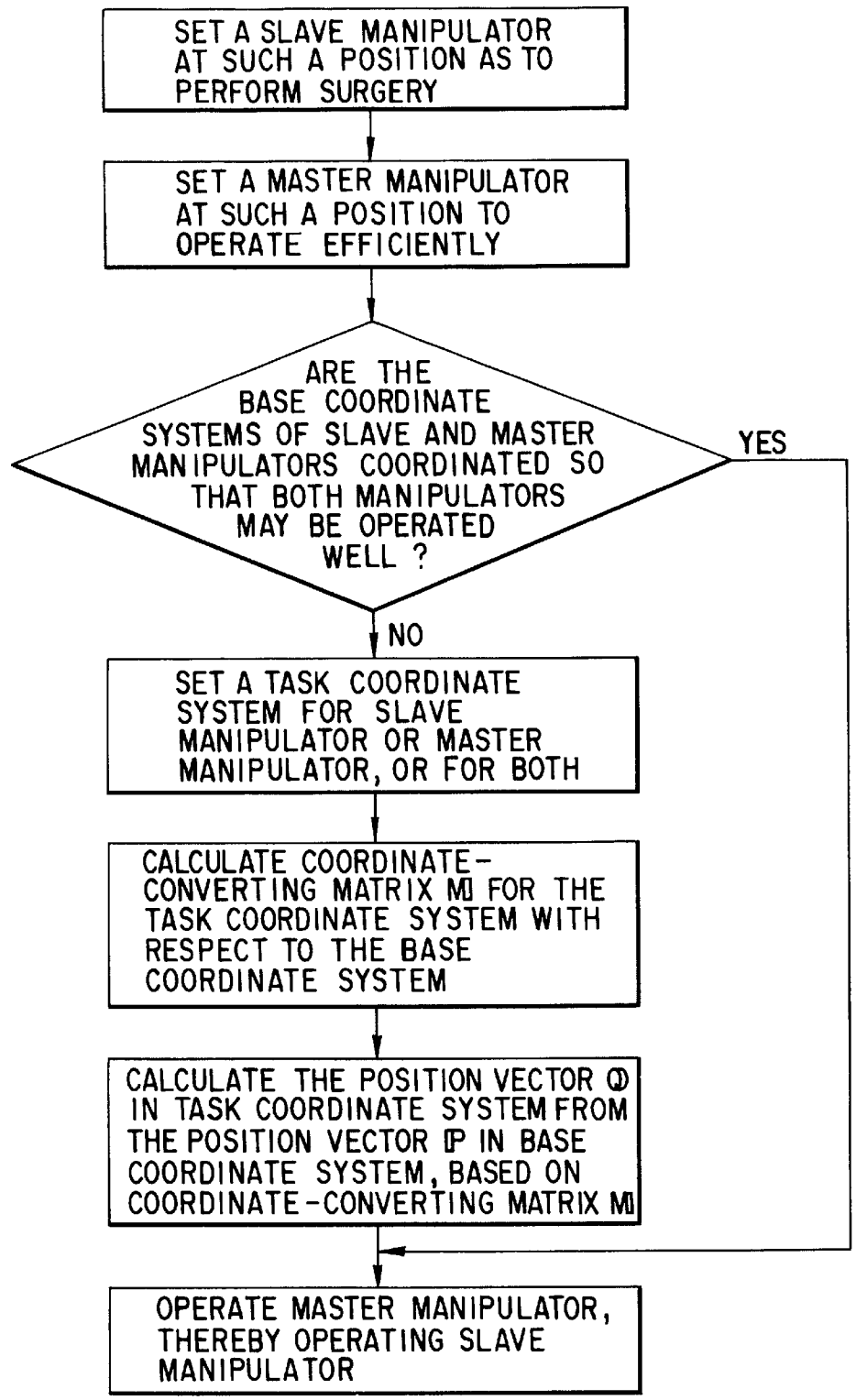
F I G. 5

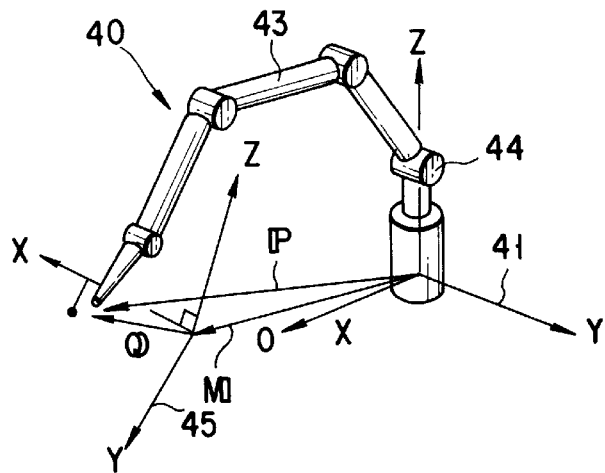
F I G. 6
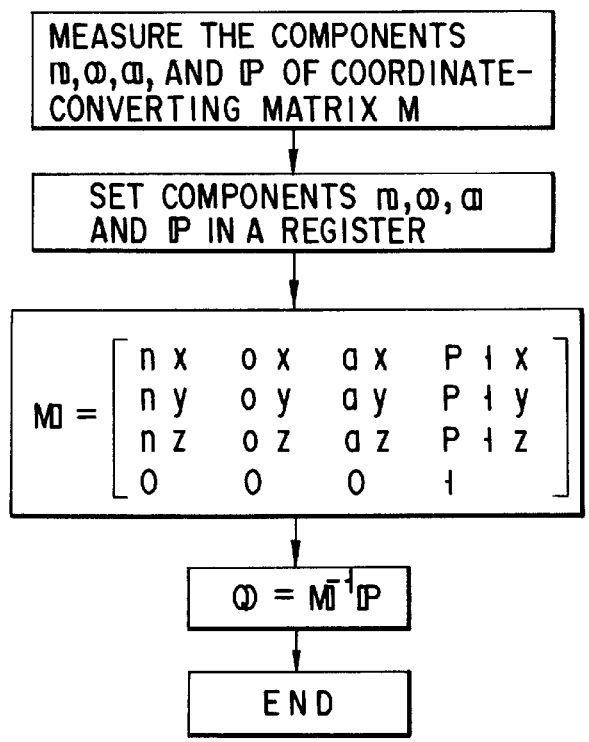
F I G. 7

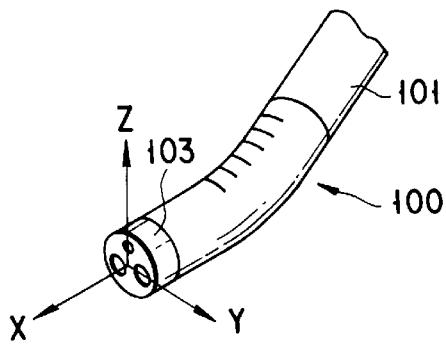
F I G. 19A
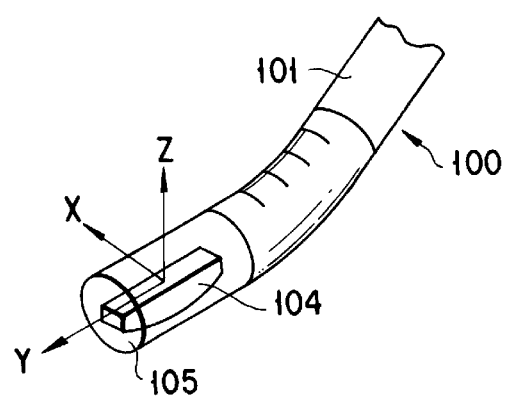
F I G. 19B
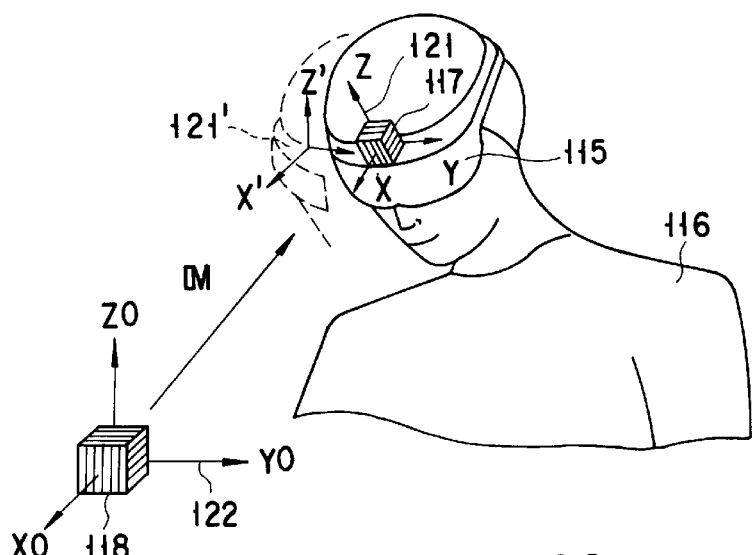
F I G. 20
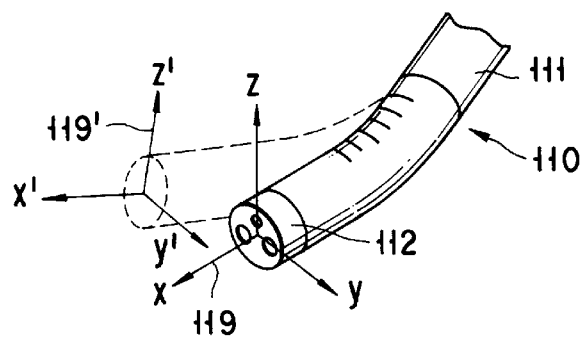
F I G. 21

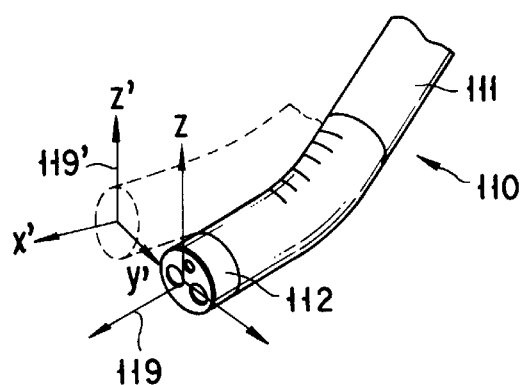
F I G. 22A
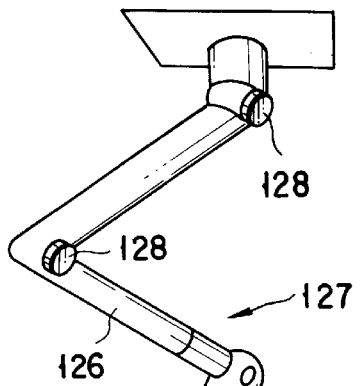
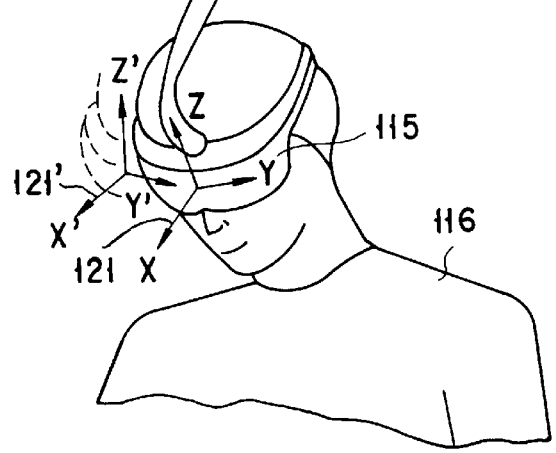
F I G. 22B
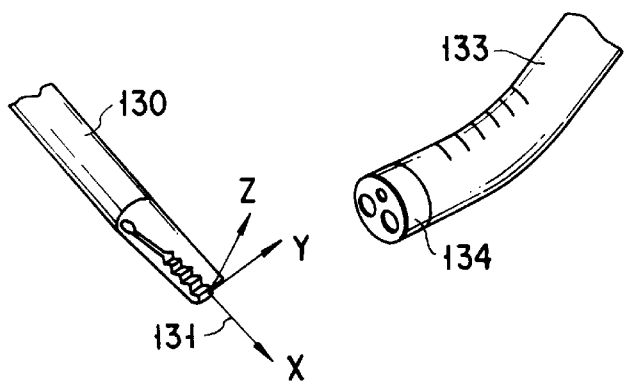
F I G. 23
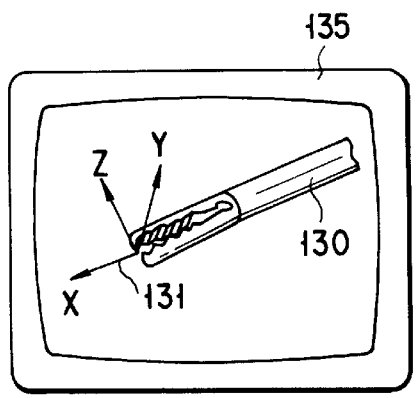
F I G. 24

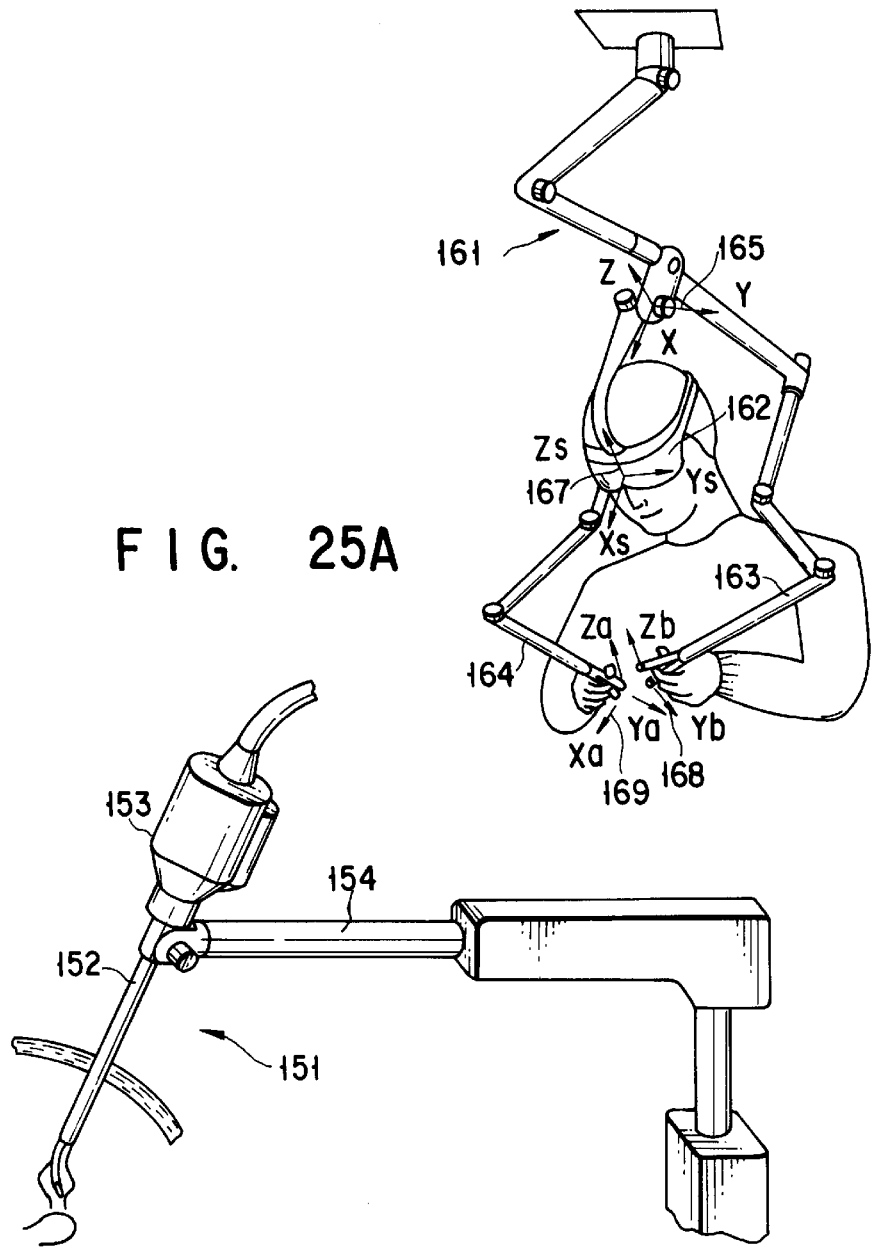
FIG. 25A
FIG. 25B
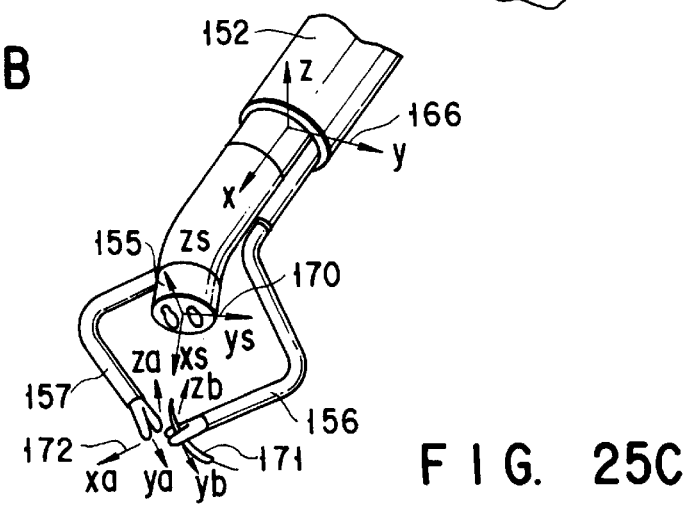
FIG. 25C

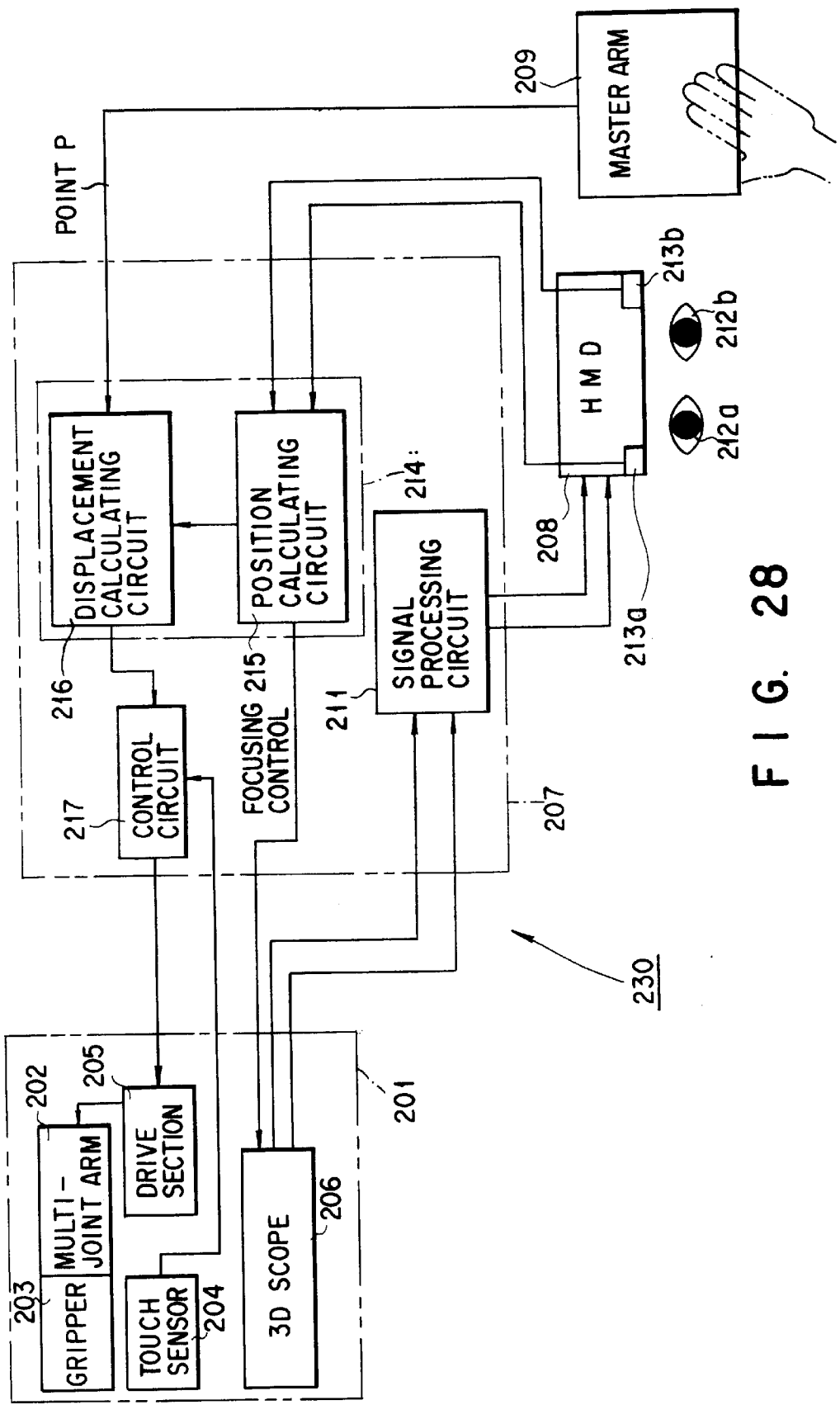
F I G. 28

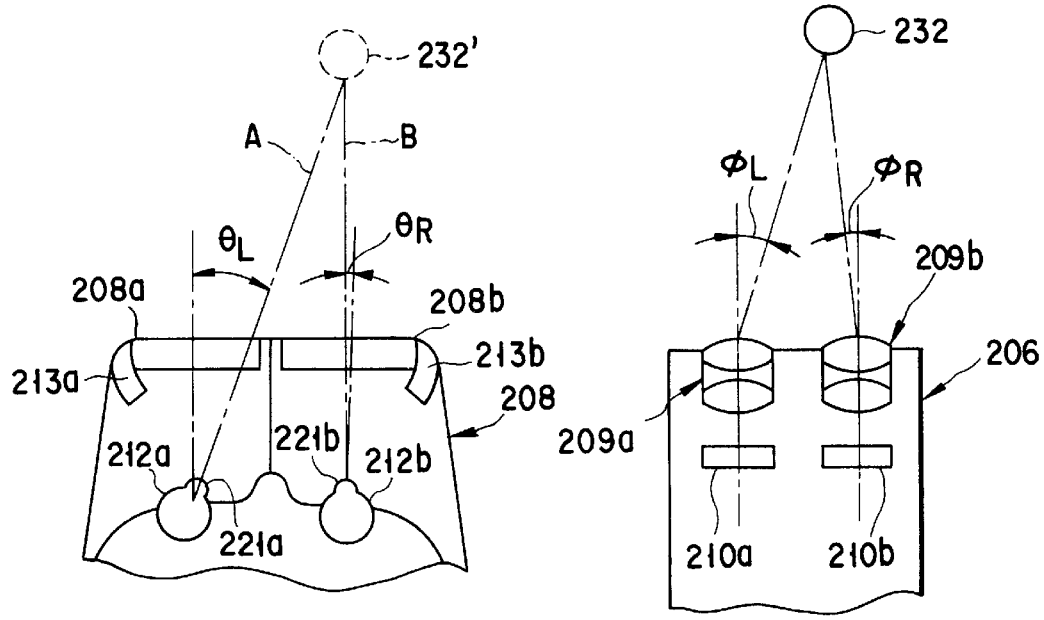
F I G. 29A    F I G. 29B
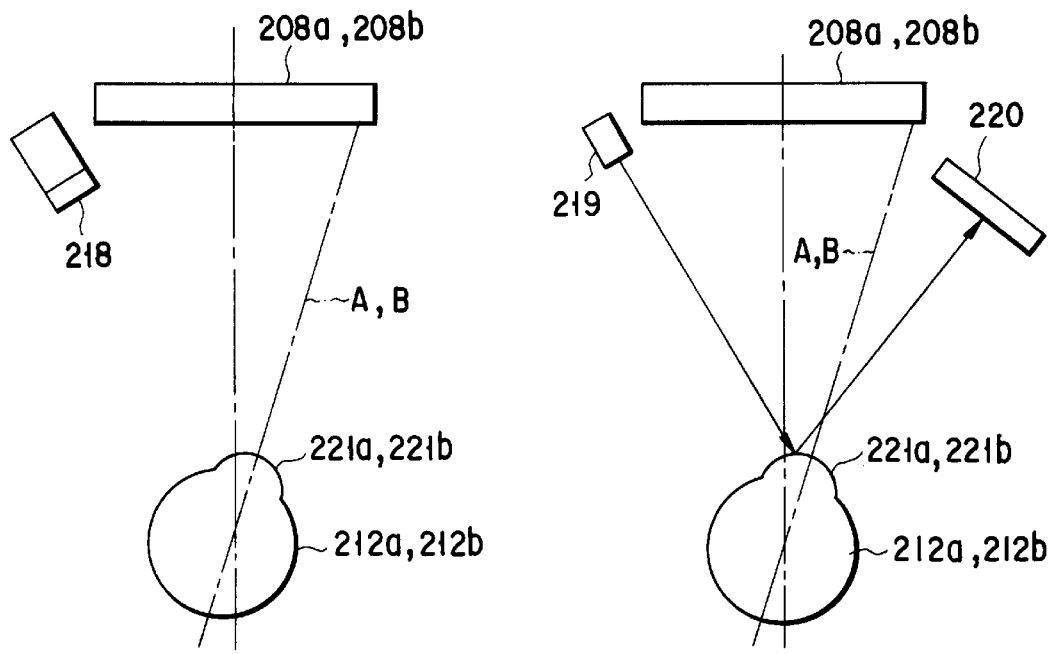
F I G. 30A    F I G. 30B

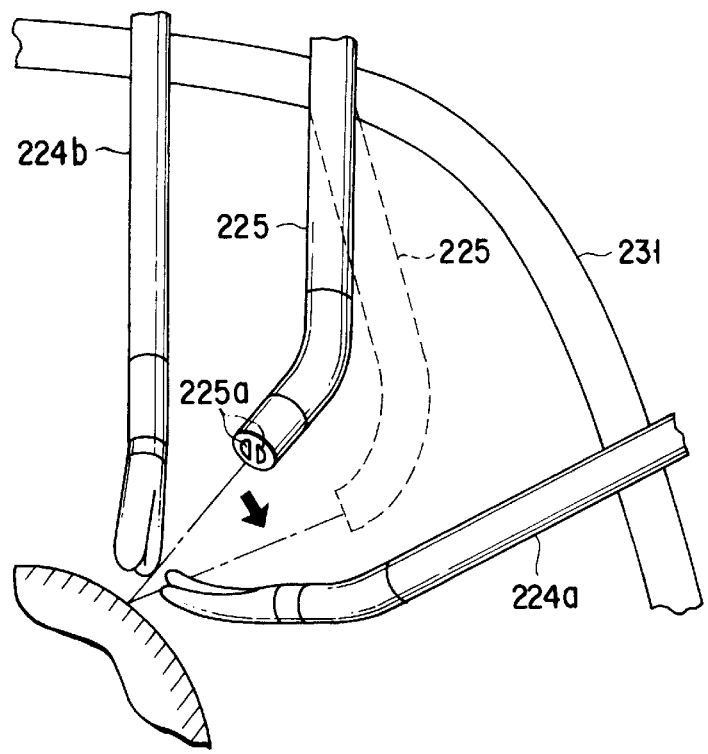
FIG. 36A
FIG. 36B
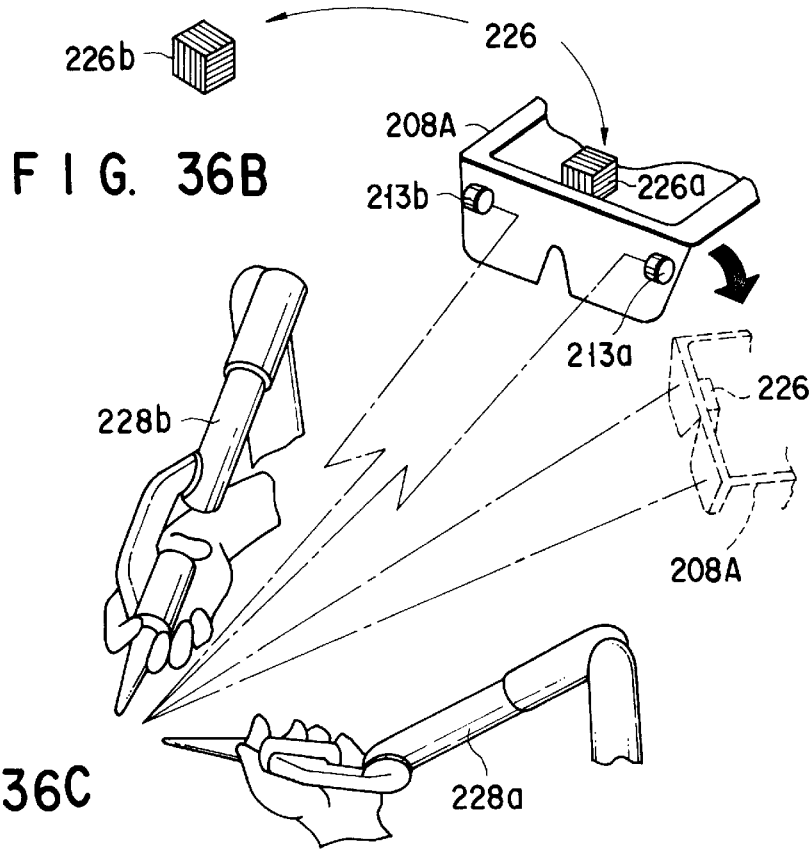
FIG. 36C

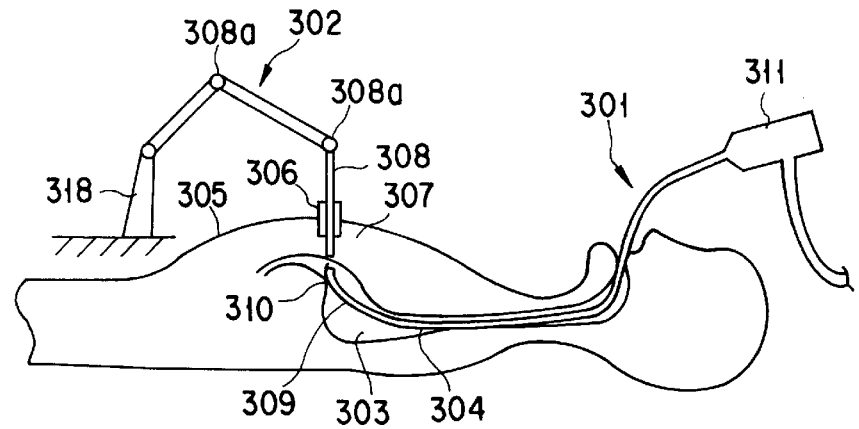
F I G. 38
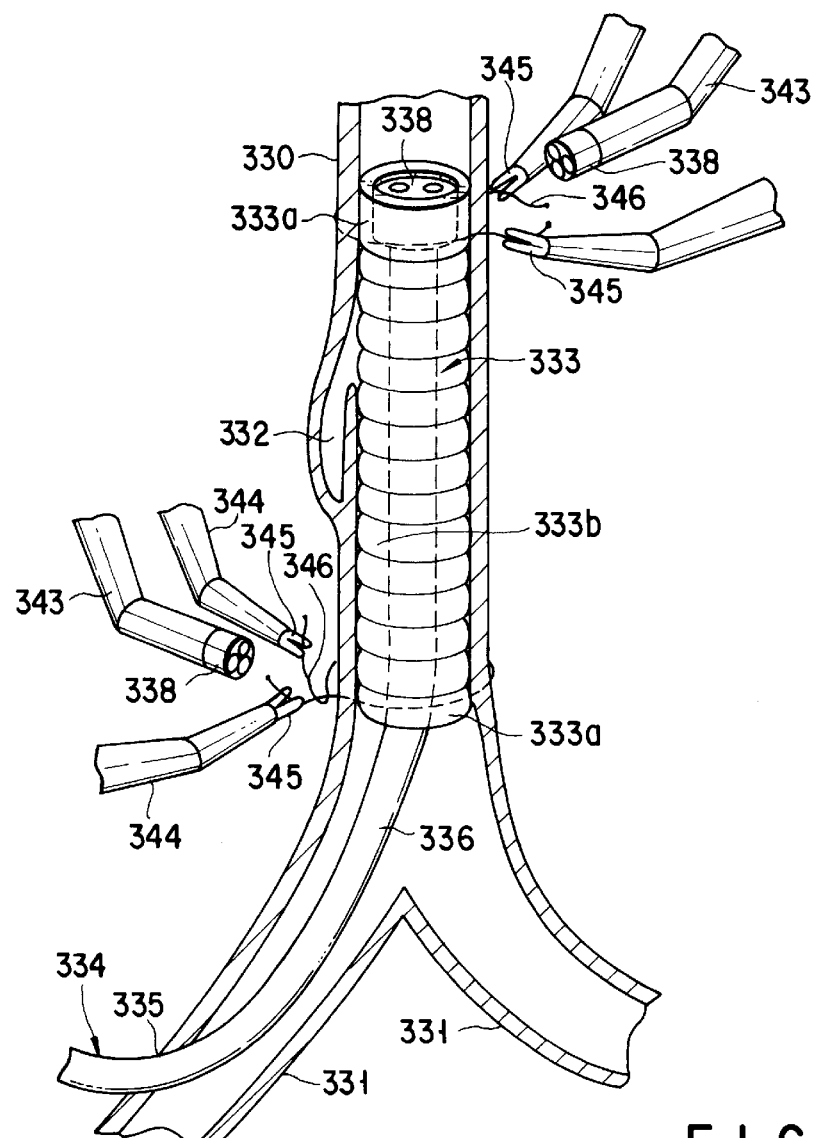
F I G. 39

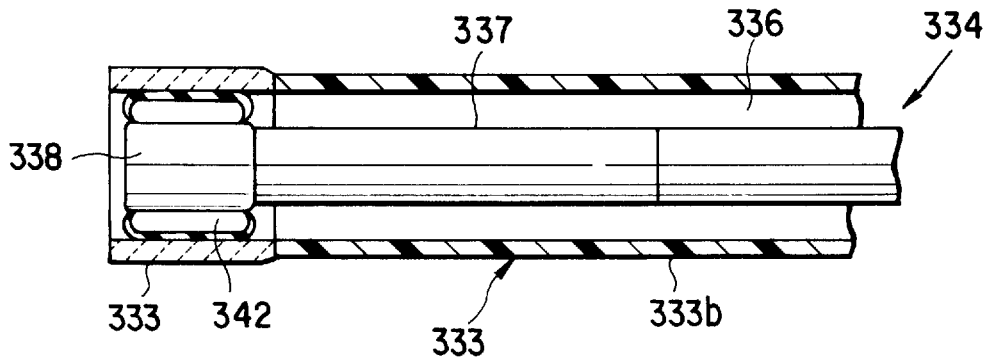
F I G. 40A
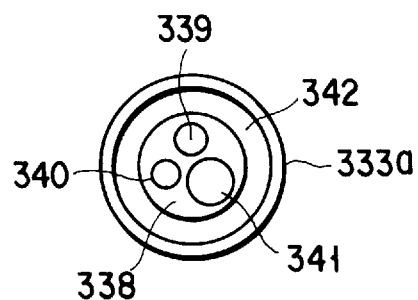
F I G. 40B
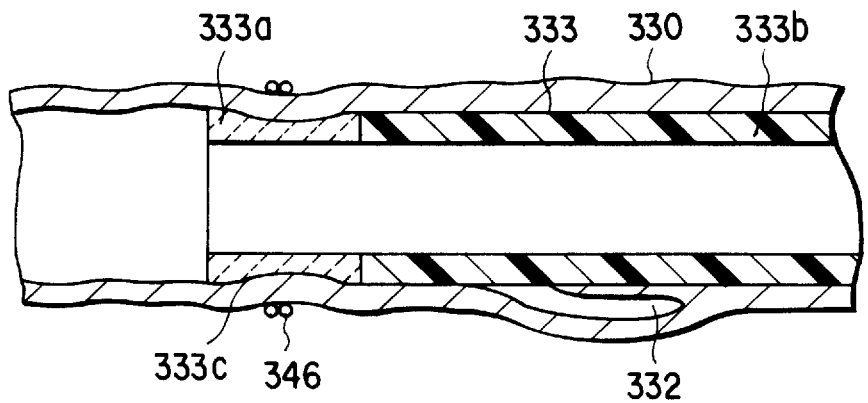
F I G. 41

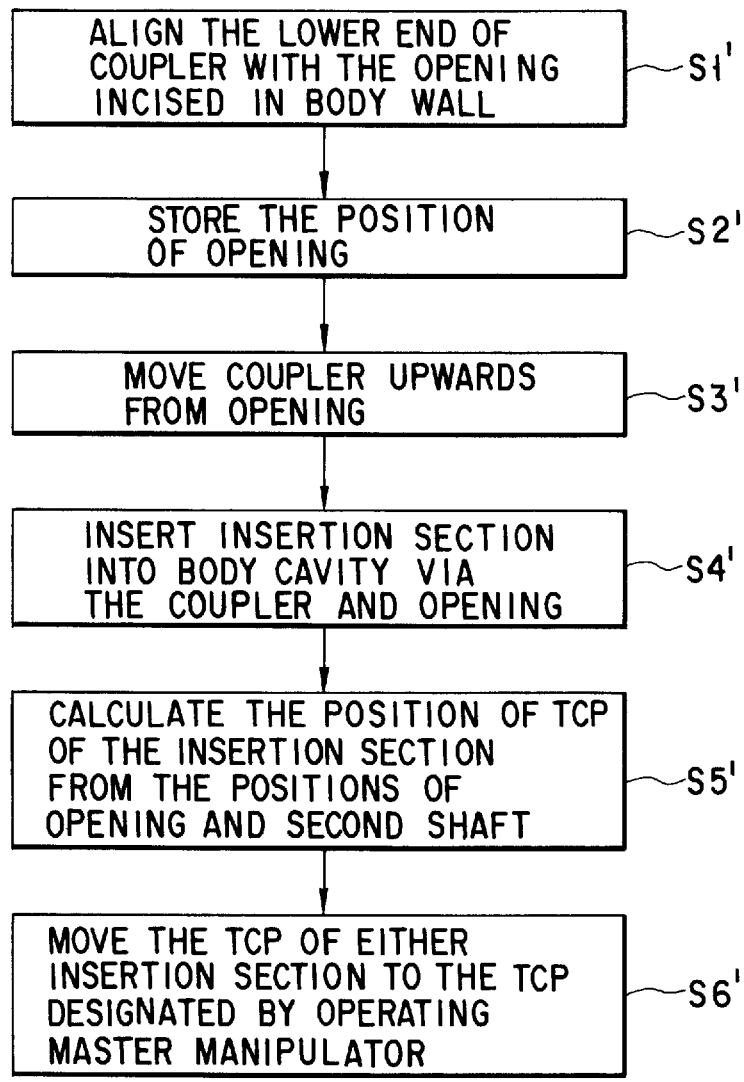
F I G. 45

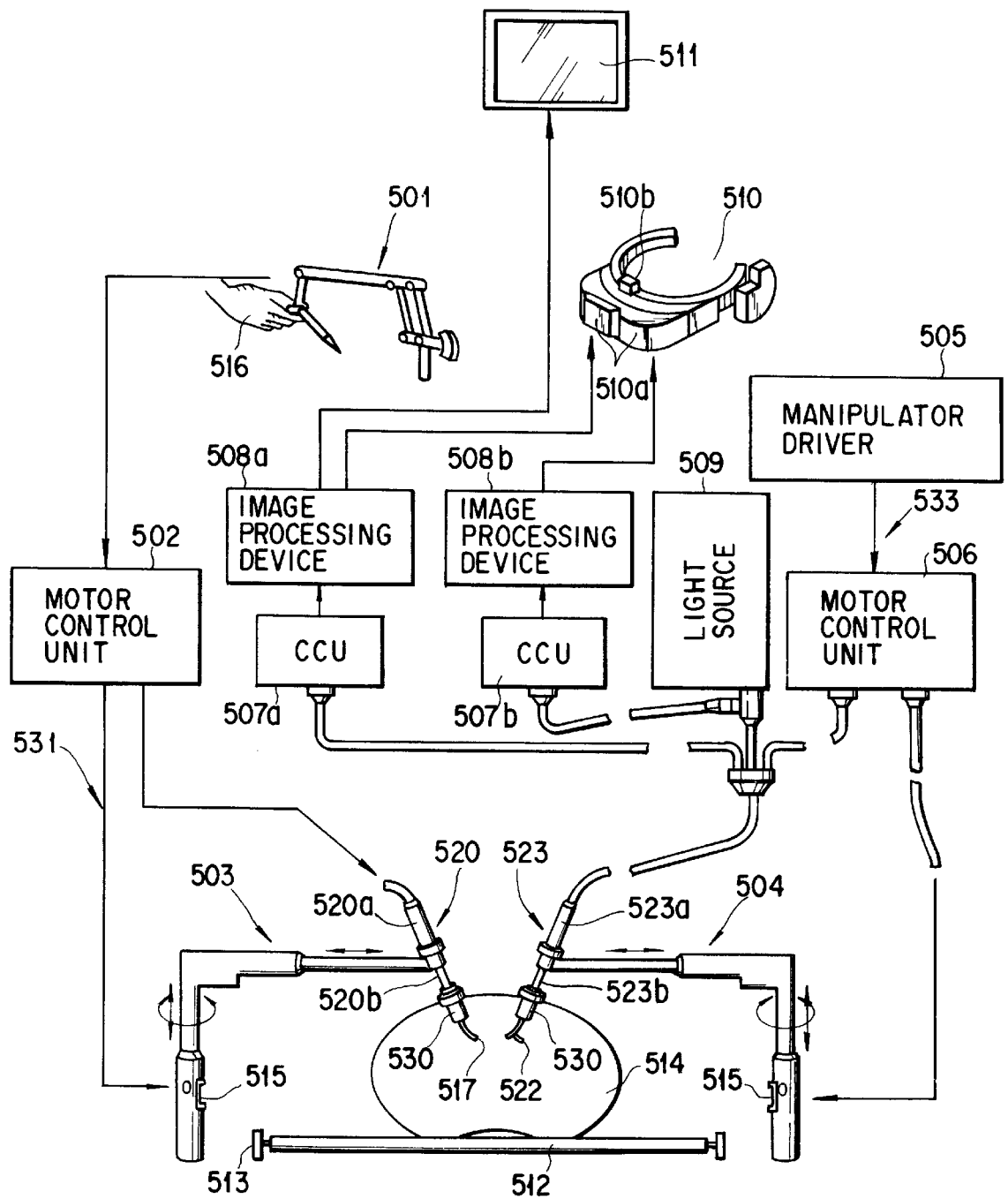
F I G. 50

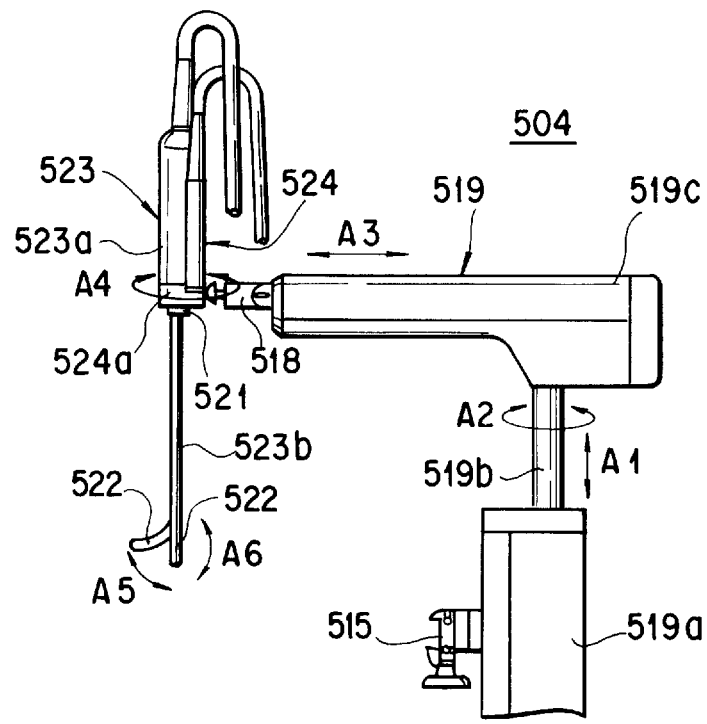
F I G. 53
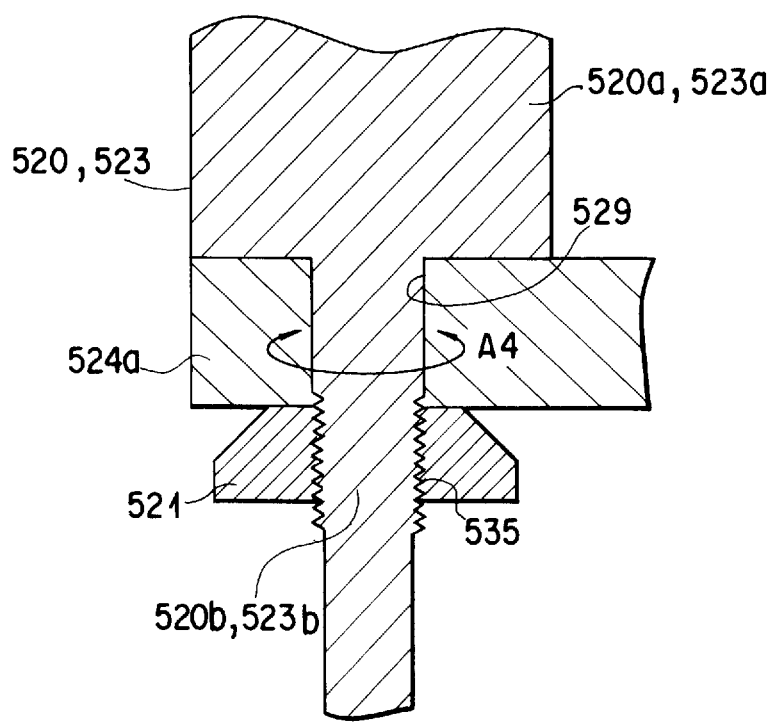
F I G. 54

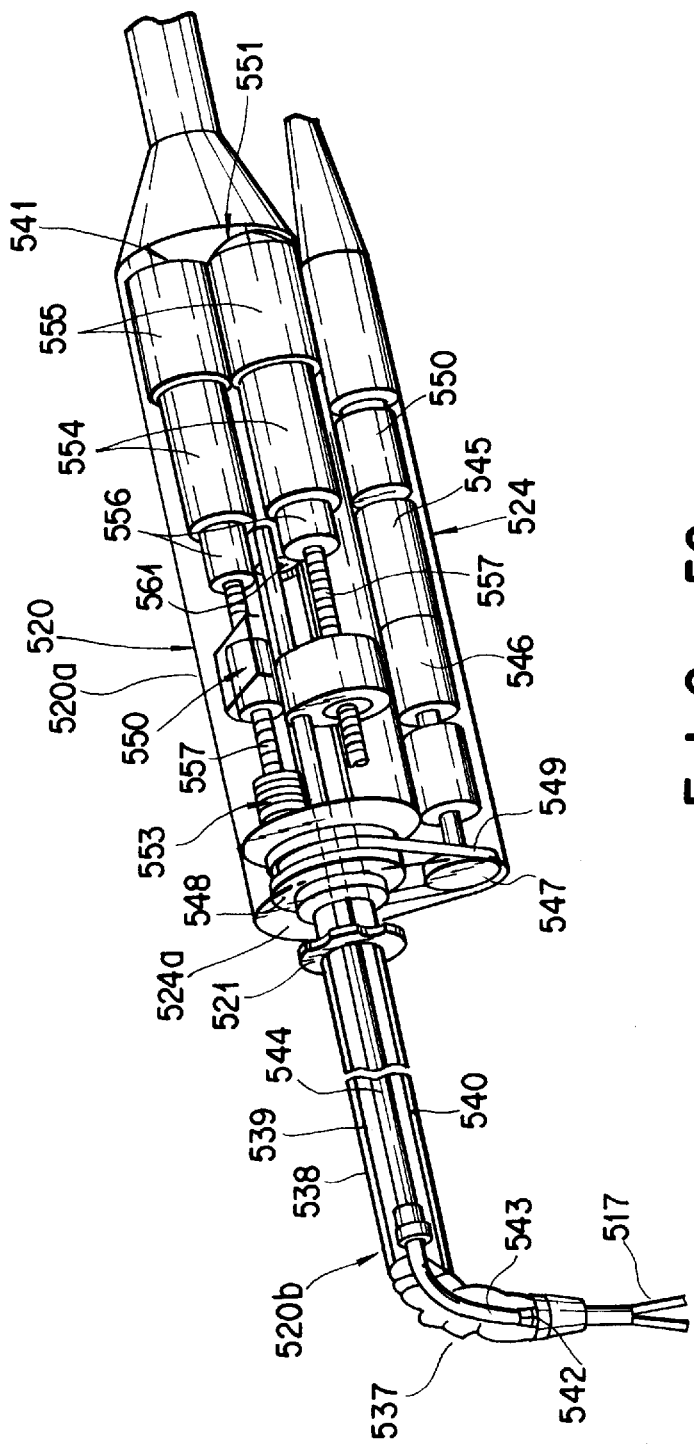
F I G. 56

SURGICAL MANIPULATION SYSTEM

This application is a Continuation of application Ser. No. 08/316,833, filed Sep. 30, 1994.

BACKGROUND OF THE INVENTION

1. Field of the Invention

The present invention relates to a surgical manipulator system, which includes a manipulator to be inserted into a body cavity of a subject and which is designed to remote-control the manipulator to make diagnosis or perform a surgery.

2. Description of the Related Art

In recent years, transcutaneous endoscope surgery has been performed in which an endoscope or a medical instrument is inserted into a body cavity through a hole cut in the body wall (e.g., the abdominal wall) to perform various treatments in the body cavity. This is because transcutaneous endoscope surgery involves no large-scale incision and is therefore scarcely invasive to the patient. This type of surgery is now widely performed to extract the gallbladder or a part of either lung.

To perform a successful transcutaneous endoscope surgery, it is desirable that the endoscope or the instrument inserted in the body cavity be manipulated in as broad a space as possible within the body cavity. An endoscope or an instrument a surgeon can manipulate with one hand is a straight one which has but little freedom of operation. Due to the little freedom of operation, it is difficult for a surgeon to orient the endoscope or instrument in order to observe the target object at a desired angle or to treat the target object, even if he or she has managed to guide the endoscope or instrument to the object in the body cavity. For example, the surgeon can hardly position an instrument holding a needle, so as to drive the needle perpendicular to a suture line in his or her effort to suture an organ located in the body cavity.

This problem with transcutaneous endoscope surgery is solved by the use of a surgical manipulator with a multi-joint insertion section which has great operation freedom. A surgical manipulator system which holds an endoscope or a medical instrument and which is manipulated by a surgeon is disclosed in U.S. Pat. No. 5,217,003. This system comprises a manipulator which has an actuator and a multi-joint insertion section for holding an endoscope or an instrument. The actuator drives the joints of the insertion section independently, whereby the insertion section is easily guided to a target organ located in a body cavity.

When the multi-joint insertion section is operated to orientate the endoscope or instrument at a desired angle to the target organ, some of the joints may contact another organ in the body cavity. Further, when the patient moves while undergoing transcutaneous endoscope surgery, the affected part moves, too, making it difficult for the surgeon to excise that part precisely.

Two types of surgical manipulator systems are available, each comprising a remote-control device, a manipulator and a TV monitor. The TV monitor displays an image of the affected part in a body cavity, which has been obtained through an endoscope inserted in the body cavity. In the system of the first type, the surgeon operates a joy stick used as the remote-control device, while looking at the image of the affected part on the TV monitor, thereby operating the manipulator in the same way in the body cavity. In the system of the second type, generally known as "master-slave system," the surgeon operates a master manipulator used as the remote-control device, while looking at the image on the TV monitor, thereby operating the slave manipulator in the same manner in the body cavity.

In either system, the remote-control device is physically separated from the manipulator. Therefore, the directions in which the remote-control device and the manipulator may move are determined by the positional relation in which the device and the manipulator are arranged. In some cases, the coordinate system for the manipulator may be orientated differently from the coordinate system for the remote-control device.

In the case of a surgical manipulator system which comprises a plurality of master manipulators and a plurality of slave manipulators, the master manipulators are usually located at the bedside close to the surgeon so that he or she can operate them, whereas the slave manipulators are arranged opposite the bedside since no space is available at any other bedside. To state another way, the master manipulators and the slave manipulators cannot be located at the same bedside in most cases. As a consequence, when the surgeon moves the corresponding master manipulator to the right in order to move the slave manipulator in the same direction, a slave manipulator may move to the left. In other words, the coordinate system for the slave manipulators is orientated differently from that for the master manipulators, increasing the possibility that a slave manipulator moves in a direction other than the very direction in which it should move as the surgeon desires.

Even if the slave manipulators are arranged at the same bedside as the master manipulators, they should be spaced away from the master manipulators so as not to interfere with the master manipulators. Hence, the slave manipulators must be orientated differently from the master manipulators. In this case, too, any slave manipulator may move in a direction other than the direction in which it should move as the surgeon desires.

When manipulators each holding an endoscope or an instrument are independently operated by using remote-control devices, to thereby perform surgery, each manipulator is moved in the direction which is determined by the positional relationship between the remote-control devices, the positional relation between the manipulators and the positional relation between each manipulator and the associated remote-control device. That is, the direction in which each manipulator can be moved is restricted. In some case, the manipulator may be moved in an undesirable direction.

In the master-slave manipulator system, so-called "bilateral control" is employed to provide a surgeon a sense of immediacy. Bilateral control consists in transmitting any force on the slave manipulator to the master manipulator and hence to the person operating the master manipulator. To enhance visual sense of immediacy, a 3D (3-dimensional) image of the object being treated is displayed on a TV monitor installed near the master manipulator.

Since the master manipulator is located far from the object, it cannot abut on the object no matter how the surgeon operates the master manipulator. Hence, the surgeon is likely to operate the master manipulator excessively, whereby the slave manipulator collides with the object excessively. If this happens, an excessive force is exerted on either the object or the slave manipulator, possibly damaging the object or the slave manipulator. To prevent such damage, the surgeon may operate the master manipulator to move the master manipulator away from the object as soon as he or she sees that the slave manipulator gets too close to the object. His or her action may be too late. This is because a long time is required to process signals generated by the master manipulator and to supply the signals to the slave manipulator.

The surgeon may manipulate the master manipulator without seeing the 3D image displayed on the TV monitor to give him or her visual sense of immediacy. In this case, the slave manipulator is likely to collide with the object, applying an excessive force on the object or receive an excessive reaction from the object.

Generally, the insertion section of a surgical manipulator is integral with an endoscope or a medical instrument. Neither the endoscope nor the medical instrument can be washed or sterilized, independently of the surgical manipulator. To wash and sterilize the endoscope or instrument, it is necessary to wash and sterilize the manipulator, as well. It would take much labor to wash and sterilize the manipulator which is large and massive.

When a manipulator having a medical instrument and a manipulator having an endoscope are simultaneously operated, they may interfere with each other during the surgical operation. If this takes place, the spaces in which the manipulators can move will be limited, inevitably reducing the operation freedom of both the medical instrument and the endoscope, and ultimately impairing the operability of the surgical manipulator system as a whole. To make matters worse, the instrument and the endoscope cannot be exchanged to assume each other's position since they are integral with the insertion sections of the respective manipulators. To release the manipulators from the mutual interference, it is necessary to remove the insertion sections from the body cavity, then to position the manipulators out of mutual interference, and finally to insert the insertion sections back into the body cavity. This sequence of operations is complex and time-consuming; it not only decreases the efficiency of the surgical operation, but also impose a great burden on the patient receiving the operation.

In the master-slave manipulator system, described above, the surgeon operates the master manipulator at a place remote from the slave manipulator and the patient, and therefore cannot attend the patient immediately in case the patient gets, for example, a heart attack, or falls into a critical condition. Nor can he or she attend the patient at once in case the patient suffers great bleeding which cannot be stopped by remote-controlling the slave manipulator, and the abdominal wall must be immediately incised in order to stop the bleeding. Another surgeon needs to stay by the patient to perform an emergency treatment such as heart massage, incision of the abdominal wall, or the like.

SUMMARY OF THE INVENTION

The first object of the present invention is to provide a surgical manipulator system which comprises a manipulator and a remote-control device for controlling the manipulator and in which the manipulator can be moved in a desired direction, not restricted by the positional relation between it and the remote-control device.

The second object of the invention is to provide a surgical manipulator system which makes a surgeon feel as he or she were in a body cavity, and with which he or she perform a transcutaneous endoscope surgery in the same way as an abdominal operation.

The third object of this invention is to provide a surgical manipulator system which has a master manipulator and a slave manipulator, and in which no excessive force is exerted on an object or the slave manipulator even if the master manipulator is operated in an erroneous manner.

The fourth object of the invention is to provide a surgical manipulator system with which it is possible to locate an object correctly and treat the object within a short time.

The fifth object of this invention is to provide a surgical manipulator system in which an endoscope and a medical instrument can be moved so freely that the interior of an body cavity may be observed and an object in the body cavity may be treated, and are prevented to contact an organ other than the target one to apply an excessive force thereon.

The sixth object of the present invention is to provide a surgical manipulator system, in which only devices (e.g., an endoscope and a medical instrument) to be inserted into a body cavity or used and removed from a body cavity, can be sterilized and washed, and problems restricting the operation of such devices can be solved easily and effectively.

The seventh object of this invention is to provide a surgical manipulator system which has a master manipulator and a slave manipulator and with which a surgeon can perform an emergency treatment immediately after he or she stops remote-controlling the slave manipulator, rendering it unnecessary for another surgeon to perform the emergent treatment and thus reducing the surgical cost.

To attain these objects, the following surgical manipulator systems are provided according to the present invention.

A first surgical manipulator system according to the invention comprises: at least one surgical manipulator having surgical means for performing a desired operation; at least one guide means for guiding the surgical means; detecting means for detecting a position and/or orientation relationship between the surgical means and the guide means, and/or a position and/or orientation relationship between the surgical means and another surgical means; and drive control means for controlling the surgical manipulator such that the surgical means is guided by the guide means.

A second surgical manipulator system according to the invention is designed to achieve the first, second and fourth objects. In this system, the detecting means has a first decision means for determining a position and/or orientation of the guide means by using a specific coordinate system as a reference, a second decision means for determining a position and/or orientation of the surgical manipulator by using a specific coordinate system as a reference, and a coordinate-system switching means for switching the coordinate system of at least one of the guide means and the surgical manipulator, to another, thereby to set the guide means and the surgical manipulator in a specific relationship in terms of position and/or orientation.

A third surgical manipulator system according to the invention is designed to accomplish the fourth object in particular, and characterized in that the detecting means comprises a permanent magnet attached to the first surgical manipulator and a Hall element attached to the second surgical manipulator.

A fourth surgical manipulator system of the invention is designed to readily attain the third object. This system comprises, among other things, two guide means are provided and operation means for calculating tool center points which the two guide means are to assume. The surgical manipulator is controlled, moving the tool center points of the surgical means to positions indicated by the guide means, only when the difference between the position of the tool center point of each surgical means and the position of the tool center point calculated by the operation means falls within a predetermined range.

A fifth surgical manipulator system according to this invention is designed to achieve the fifth object. In the system, the surgical means comprises a straight insertion section and a surgical section which is connected to a distal end of the insertion section and which is able to bend to treat an affected part of a subject and/or provide an image of the affected part of the subject, and the surgical manipulator comprises coupling means for holding the insertion section, while allowing the insertion section to move back and forth, and positioning means for positioning the insertion section.

A sixth surgical manipulator system of the invention is designed to attain the sixth object, and comprises, among other things, a connecting mechanism for removably connecting at least one part of the surgical means to the surgical manipulator.

A seventh surgical manipulator system according to the present invention is designed to accomplish the seventh object, and comprises, among other things, fastening means for removably fastening the surgical manipulator to an operating table.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 19A and 19B are perspective views of the distal end portion of the manipulator incorporated in the fourth embodiment;

FIG. 20 is a perspective view of the manipulator controller incorporated in the surgical manipulator system according to the fifth embodiment of the present invention;

FIG. 21 is a perspective view of the manipulator used in the fifth embodiment;

FIGS. 22A and 22B are perspective views showing some of the components of the surgical manipulator system according to the sixth embodiment of the invention;

FIG. 23 is a perspective view showing the two manipulators incorporated in the seventh embodiment of this invention;

FIG. 24 is a front view of the TV monitor used in the seventh embodiment of the invention;

FIGS. 25A, 25B and 25C are perspective views showing the surgical manipulator system according to the eighth embodiment of the invention;

FIG. 28 is a block diagram illustrating the surgical manipulator system according to the eleventh embodiment of the present invention;

FIG. 29A is a diagram schematically showing the head-mount display used in the eleventh embodiment;

FIG. 29B is a diagram schematically showing the 3D scope used in the eleventh embodiment;

FIGS. 30A and 30B show two types of sensors for detecting the orientation of the optical axis of the eye, which can be used in the eleventh embodiment;

FIGS. 36A to 36C are diagrams explaining the operation of the twelfth embodiment;

FIG. 38 is a diagram showing the entire surgical manipulator system according to the thirteenth embodiment;

FIG. 39 is a perspective view showing the surgical manipulator system according to the fourteenth embodiment of the invention, and explaining how the system is used to implant an artificial blood vessel in the aorta;

FIG. 40A is a longitudinal sectional view of an artificial blood vessel and the endoscope used in the fourteenth embodiment of the invention, the latter inserted in the former;

FIG. 40B is a front view of the endoscope incorporated in the fourteenth embodiment;

FIG. 41 is a longitudinal sectional view of the aorta and the artificial blood vessel, the latter implanted in the former;

FIG. 45 is a flow chart explaining the operation of the fifteenth embodiment;

FIG. 50 is a diagram schematically showing the surgical manipulator system according to the nineteenth embodiment of the present invention;

FIG. 53 is side view of the second manipulator incorporated in the nineteenth embodiment, which is equipped with a 3D scope;

FIG. 54 is a sectional view showing a mechanism for connecting a medical instrument or a 3D scope to the holder section of the surgical manipulator used in the nineteenth embodiment;

FIG. 56 is a perspective view showing the internal structures of the medical instrument and the holder section of the surgical manipulator;

DETAILED DESCRIPTION OF THE PREFERRED EMBODIMENTS

Embodiments of the invention will be described below, with reference to the accompanying drawings.

FIGS. 1 to 10 show a surgical manipulator system according to the first embodiment of the invention. This system is characterized in that a slave manipulator and a master manipulator for remote-controlling the slave manipulator can be set in any desired relation in terms of the direction in which they are moved.

Figure 1:
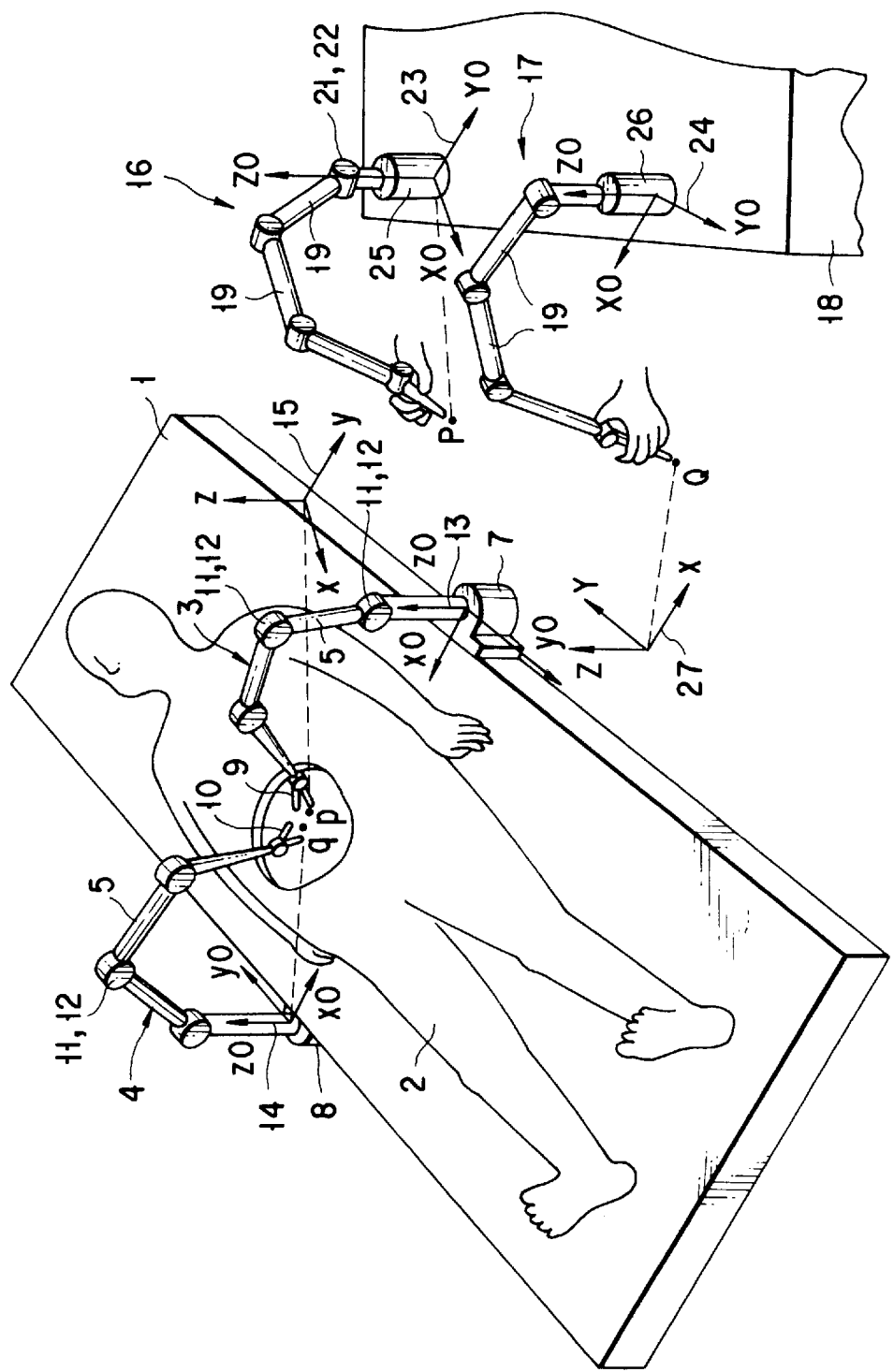
FIG. 1 is a perspective view showing a surgical manipulator system according to the first embodiment of the present invention.

FIG. 1 is a schematic representation of the surgical manipulator system. As shown in FIG. 1, the system comprises an operating table 1, two slave manipulators 3 and 4, two master manipulators 16 and 17, and a console 18. A patient 2 lies on the table 1, on his or her back.

The slave manipulators 3 and 4 are multi-joint ones, each comprising a plurality of arms 5 which are jointed end to end. The slave manipulators 3 and 4 are secured to the left and right sides of the operating table 1, respectively. More precisely, the base 7 of the first slave manipulator 3 is fixed to the right side of the table 1, and the base 8 of the second slave manipulator 4 to the left side of the table 1. The slave manipulators 3 and 4 extend from the respective bedsides toward that part of the patient 2 on which surgery will be or is being performed.

The distal ends of the slave manipulators 3 and 4 hold medical instruments 9 and 10, respectively, each of which is, for example, a forceps, a knife, a suture device, a syringe or the like. Instead, the distal end of each slave manipulator may hold an observation device, such as an endoscope, an ultrasonic echo probe, a surgical microscope or the like. Both slave manipulators 3 and 4 are operated such that their distal end portions are inserted into a body cavity through an opening incised in the abdominal wall. Transcutaneous surgery or transcutaneous endoscope surgery can thereby be accomplished.

An actuator 11 and an encoder 12 are provided at a joint between any two adjacent arms of either slave manipulator. When driven by a controller, the actuator 11 rotates the first of the two adjacent arms with respect to the second arm. The encoder 12 detects the angle by which the first arm has been rotated.

The slave manipulators 3 and 4 have specific base coordinate systems 13 and 14, respectively. As shown in FIG. 1, each base coordinate system is an orthogonal one, having an origin at the base (7 or 8) and three axes $X_0$, $Y_0$ and $Z_0$. Either slave manipulator has a task coordinate system 15, as well. The task coordinate system can be altered whenever necessary, as will be explained later. The controller for both slave manipulators 3 and 4 receives information from the controller for the master manipulators 16 and 17. Then, it sets the positions and orientations of the slave manipulators 3 and 4 with respect to the specific coordinate system in accordance with the information, and controls the slave manipulators 3 and 4.

A surgeon stands at the right side of the operating table 1, hence close to the first slave manipulator 3. The master manipulators 16 and 17 are installed at the right side of the bed 1, too. They are fastened to the console 18. More specifically, the first master manipulator 16 has its base 25 secured to the console 18, whereas the second master manipulator 17 has its base 26 secured to the console 18. The console 18 is spaced away from the operating table 1. Alternatively, the console 18 may be secured directly to the right side of the operating table 1.

The console 18 can be moved to any position desired, so that the surgeon may have easy access to it. In most cases, the console 18 is placed on the floor of the operating room. It may be suspended from the ceiling, instead. In any case, the console 18 is located at one side of the table 1 to enable the surgeon to operate both master manipulators 16 and 17.

The slave manipulators 3 and 4 are multi-joint ones, each comprising a plurality of arms 5 which are jointed end to end. An actuator 21 and an encoder 22 are provided at a joint between any two adjacent arms of either master manipulator. When driven by a controller, the actuator 21 rotates the first of the two adjacent arms with respect to the second arm. The encoder 22 detects the angle by which the first arm has been rotated.

The master manipulators 16 and 17 have specific base coordinate systems 23 and 24, respectively. As shown in FIG. 1, each base coordinate system is an orthogonal one, having an origin at the base (25 or 26) and three axes $X_0$, $Y_0$ and $Z_0$. The master manipulators share a task coordinate system 27. The task coordinate system 27 can be altered whenever necessary, as will be explained later. The controller for both master manipulators 16 and 17 sets the positions and orientations of the master manipulators 16 and 17 with respect to the specific coordinate system, and controls the master manipulators 16 and 17.

Figure 2:
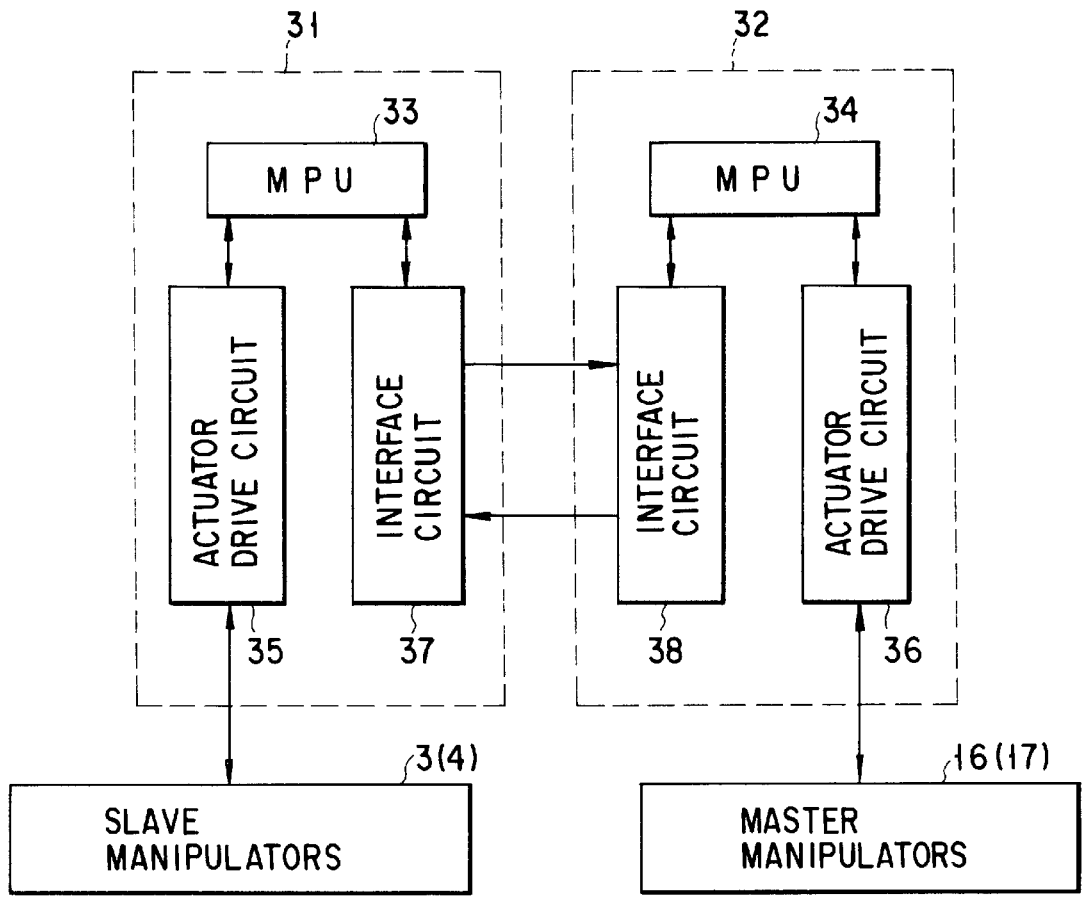
FIG. 2 is a block diagram of the control system for controlling the manipulators of the surgical manipulator system shown in FIG. 1.

FIG. 2 is a block diagram showing the control system for controlling the slave manipulators 3 and 4 and the master manipulators 16 and 17. As shown in FIG. 2, the control system has a first controller 31 for controlling the slave manipulators 3 and 4 and a second controller 32 for controlling the master manipulators. The first controller 31 comprises an MPU (Micro Processor Unit) 33, an actuator drive circuit 35 and an interface circuit 37. Similarly, the second controller 32 comprises an MPU 34, an actuator drive circuit 36 and an interface circuit 38.

The MPU 34 calculates the positions of the distal ends of the master manipulators 16 and 17, i.e., TCPs (Tool Center Points), as coordinate data for the space defined by the base coordinate systems 23 and 24 or by the task coordinate system 27. More precisely, the MPU 34 generates the coordinate data by performing geometrical vector synthesis of the rotation angles of the arms constituting either master manipulator, which have been detected by the encoders 22 provided at the joints among the arms. The coordinate data is transmitted via the interface circuit 38 to the interface circuit 37 of the first controller 31, and hence to the MPU 33 thereof.

The MPU 33 uses the coordinate data supplied from the MPU 34 of the second controller 32 and generates an operation command to the slave manipulators 3 and 4. To be more specific, the MPU 33 calculates the positions of the distal ends of the slave manipulators 3 and 4, i.e., TCPs, as coordinate data for the space defined by the base coordinate systems 13 and 14 or by the task coordinate system 15, and finds a deviation of this coordinate data from the coordinate data supplied from the MPU 34. The deviation, thus found, is the operation command. The operation command is supplied to the actuator drive circuit 35. The circuit 35 drives the slave manipulators 3 and 4 in accordance with the operation command.

The deviation calculated by the MPU 33 of the first controller 31 is transmitted via the interface circuit 37 to the interface circuit 38 of the second controller 32, and hence to the MPU 34 thereof. The MPU 34 generates a force command from the deviation. The force command is supplied to the actuator drive circuit 36. The circuit 36 drives the actuators 21 on both master manipulators 16 and 17. The actuators 21 on each master manipulator generate a force which acts against the force the surgeon is applying on the master manipulator. The surgeon feels the force generated by the actuators 21.

Referring back to FIG. 1, as the surgeon operates the master manipulator 16, the slave manipulator 3 which is associated with the master manipulator 16 is operated in the same way. In operation, the slave manipulator 3 follows the master manipulator 16.

In the first embodiment, the first controller 31 controls the slave manipulator 3 such that the task coordinate system 15 (FIG. 1) is identical in orientation to, but different in position from, the base coordinate system 23 of the master manipulator 16. The TCP of the master manipulator 16, or a point P present in the base coordinate system 23, corresponds to a point p present in the task coordinate system 15 of the slave manipulator 3. Thus, when the master manipulator 16 is moved, the slave manipulator 3 is moved in the same direction as the master manipulator 16.

As shown in FIG. 1, the task coordinate system 27 of the master manipulator 17 is set, as described later, such that it is identical in orientation to, but different in position from, the base coordinate system 14 of the slave manipulator 4. The TCP of the master manipulator 17, or a point Q present in the base coordinate system 27, corresponds to a point q present in the task coordinate system 14 of the slave manipulator 4. Therefore, when the master manipulator 17 is moved, the slave manipulator 4 is moved in the same direction as the master manipulator 17.

The task coordinate system 27 common to the master manipulators 16 and 17 and the task coordinate system 15 common to the slave manipulators 3 and 4 can be altered in various methods, each using vectors or matrices. Of these methods, the following three will be described.

First Method

Figure 3:
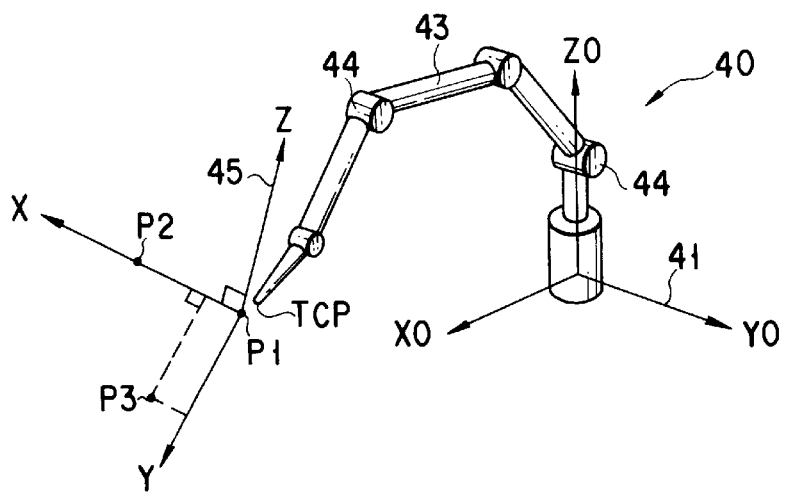
FIG. 3 is a perspective view of a manipulator, for explaining a first method of altering the coordinate system of each of the manipulators incorporated in the system shown in FIG. 1.
Figure 4:
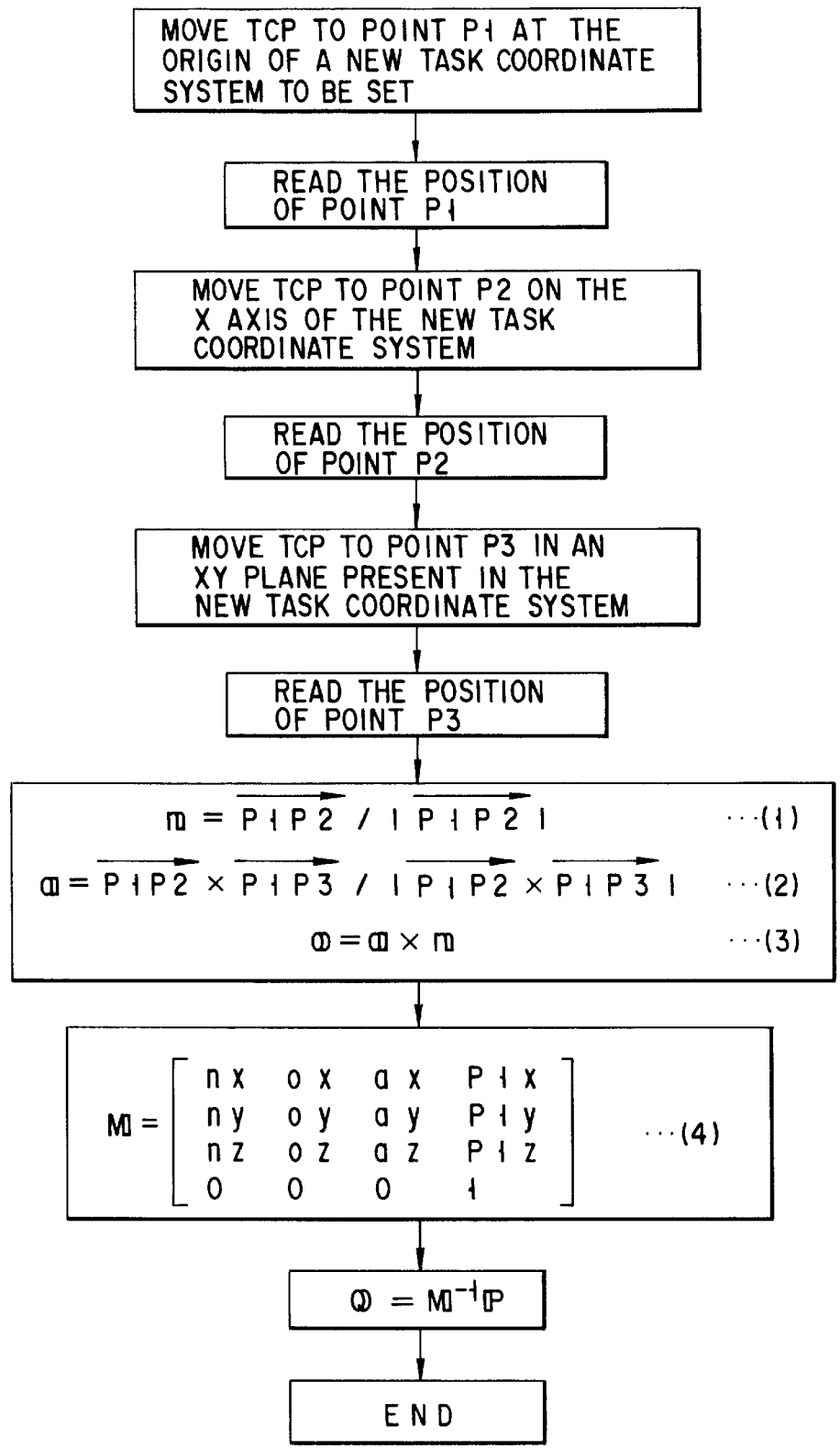
FIG. 4 is a flow chart explaining the first method of altering the coordinate system of the manipulator.

This is called "three-point, touch-up method," which will be explained with reference to FIGS. 3 and 4. FIG. 3 is a perspective view of a manipulator 40 which is any one of the four manipulators 3, 4, 16 and 17 of the surgical manipulator system shown in FIG. 1. FIG. 4 is a flow chart explaining the three-point, touch-up method.

The position data of the TCP of the manipulator 40, which exists in a base coordinate system 41, is obtained from the lengths of the arms 43 constituting the manipulator 40 and the rotation angles detected by the encoders 44 provided at the joints among the arms 43.

To set, in a space, a new task coordinate system 45 desirable for operating the manipulator 40 to perform surgery, an origin P1 is first set for the task coordinate system 45. Then, the manipulator 40 is operated, moving the TCP to the origin P1. The controllers 31 and 32 read and store the position data of the origin P1, so that they can use the position data to define the position of the origin P1 of the task coordinate system 45.

Next, a provisional X axis is orientated in a direction suitable for operating the manipulator 40 to perform surgery. This done, the manipulator 40 is operated, moving the TCP from the origin P1 to a point P2 on the positive part of the provisional X axis. The controllers 31 and 32 read and store the position data of the point P2. At the same time, the first vector (P₁P₂), extending from the origin P1 to the point P2, is obtained, thus defining the X axis of the task coordinate system 45. (Here and hereinafter, no arrow is shown over the symbols of two points to indicate a vector.)

Further, a point P3 whose Y-axis component is on the positive side is set in an XY plane desirable for operating the manipulator 40 to perform surgery. The manipulator 40 is then operated, moving the TCP to the point P3. The controllers 31 and 32 read and store the position data of the point P3.

Then, the second vector (P₁P₃) extending from the origin P1 to the point P3 is obtained. An outer product of the first and second vectors, i.e., {vector (P₁P₂)×vector (P₁P₃)}, is obtained. The direction of the outer product is the direction of the Z axis of the task coordinate system 45. Further, a product, {vector (P₁P₂)×vector (P₁P₃)×vector (P₁P₂)}, is obtained. This product is the direction of the Y axis of the task coordinate system 45.

As a result, the new task coordinate system 45 is defined in a space, by operating the manipulator 40, moving the TCP to three points in that space.

Figure 5:
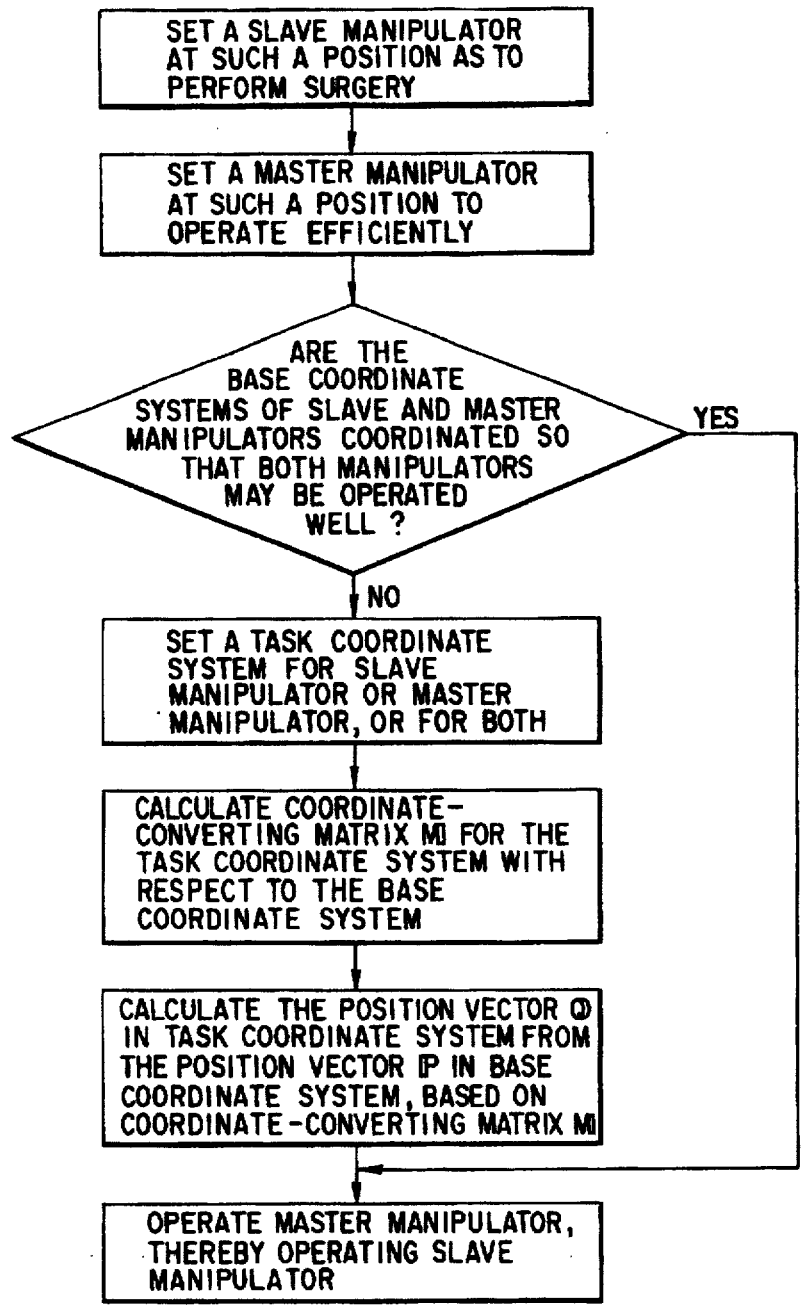
FIG. 5 is a flow chart explaining a modification of the method of altering the coordinate system of the manipulator shown in FIG. 3.

The three-point, touch-up method may be modified. For example, a coordinate matrix M for the new task coordinate system 45 is calculated by applying the formulas (1), (2) and (3) presented in FIG. 4. To find the position vector Q of the TCP in the task coordinate system 45, the position vector P of the TCP in the base coordinate system 41, which is known, is multiplied, from the left, by a coordinate matrix $M^{-1}$. Thus, $Q=M^{-1}P$. FIG. 5 is a flow chart showing the sequence of steps for setting the new task coordinate system 45.

Second Method

Figure 6:
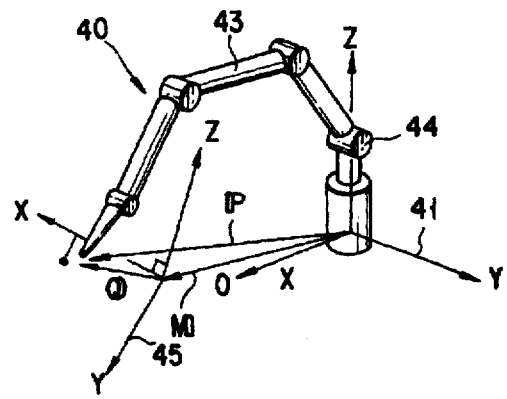
FIG. 6 is a perspective view of a manipulator, for explaining a second method of altering the coordinate system of each of the manipulators incorporated in the system shown in FIG. 1.
Figure 7:
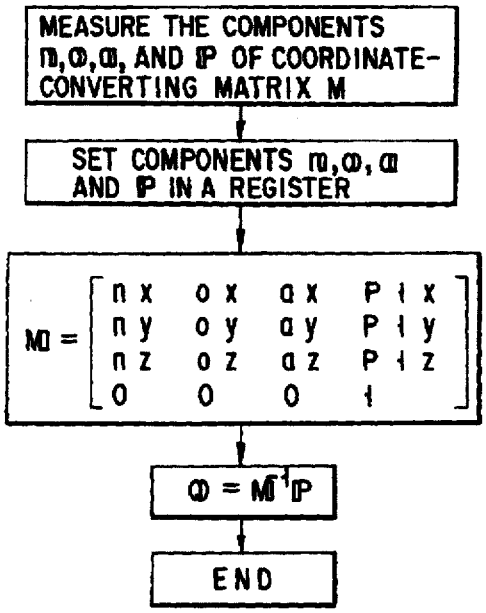
FIG. 7 is a flow chart explaining the second method of altering the coordinate system of the manipulator.
Figure 4:
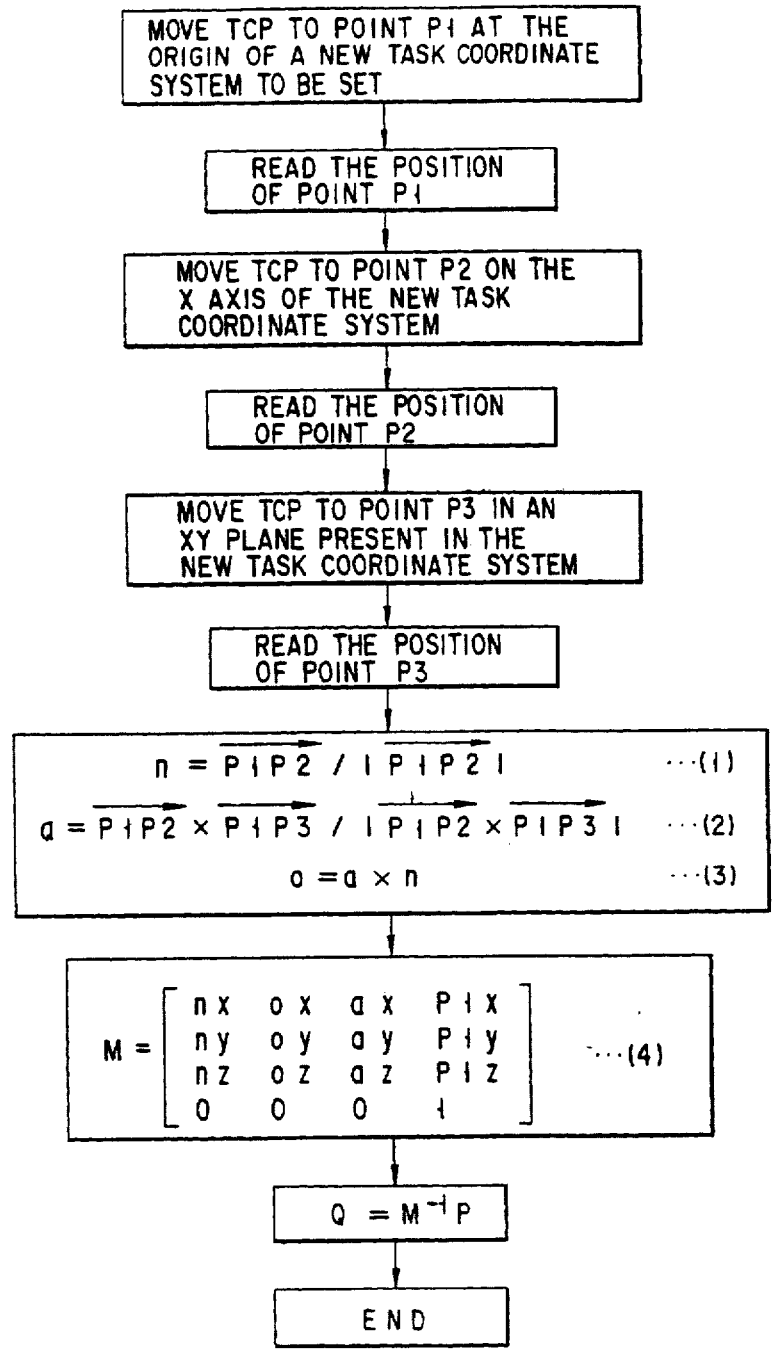
Figure 5:
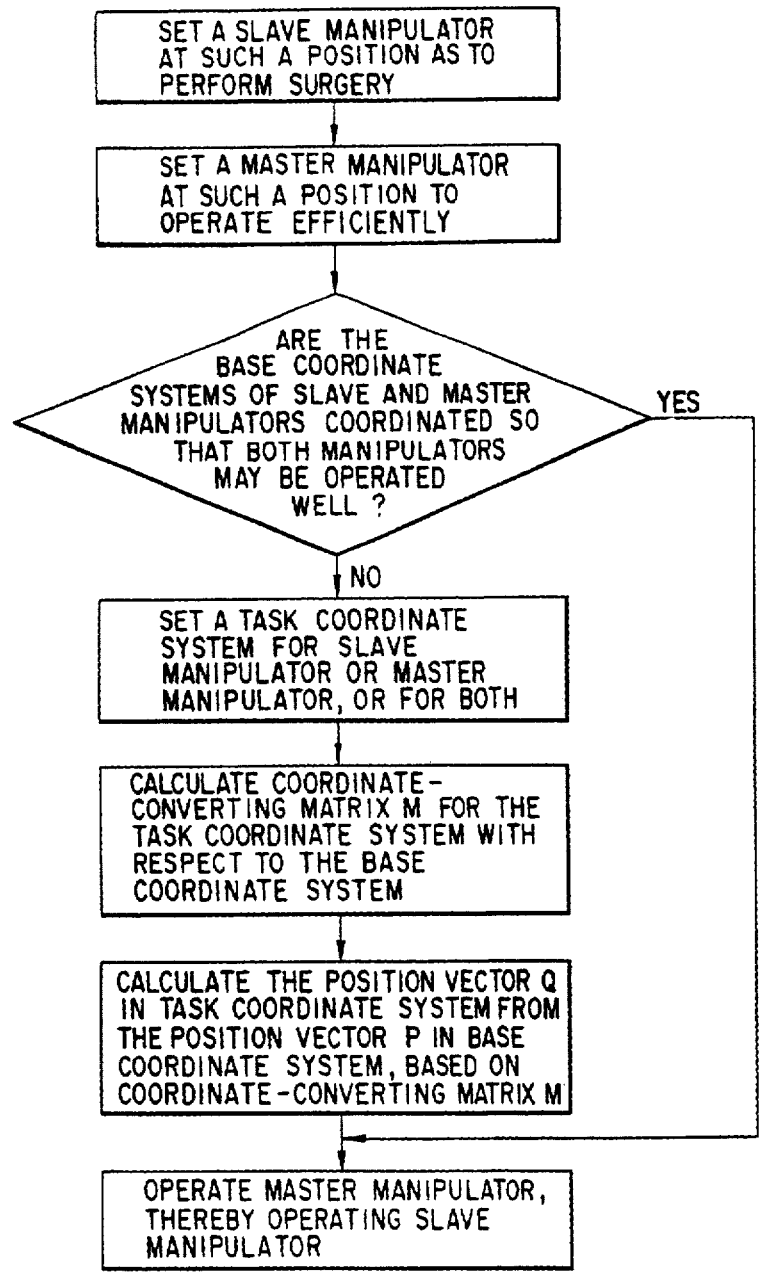
Figure 6:
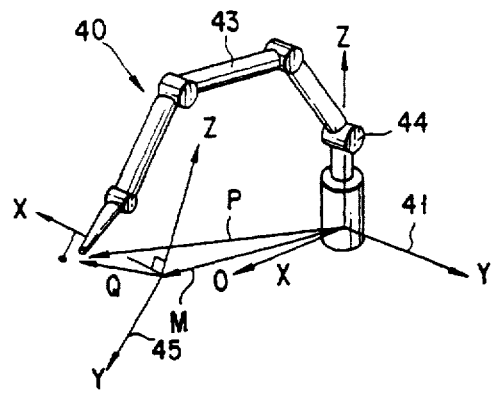
Figure 7:
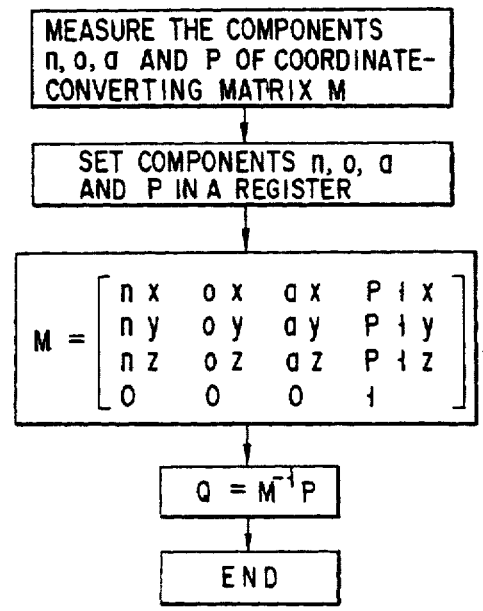
Figure 8:
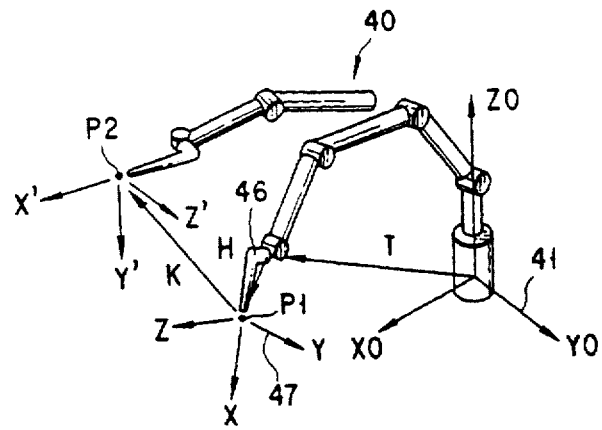
Figure 9:
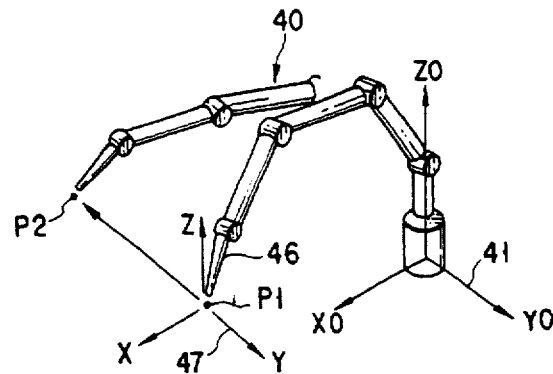
Figure 10:
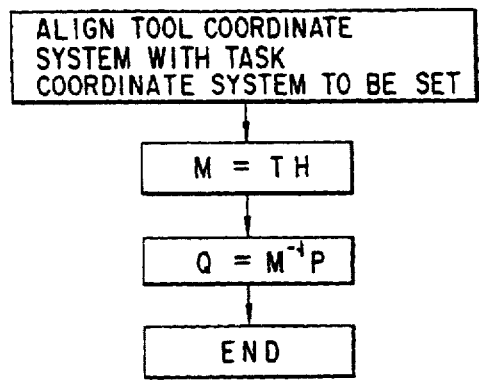
Figure 14:
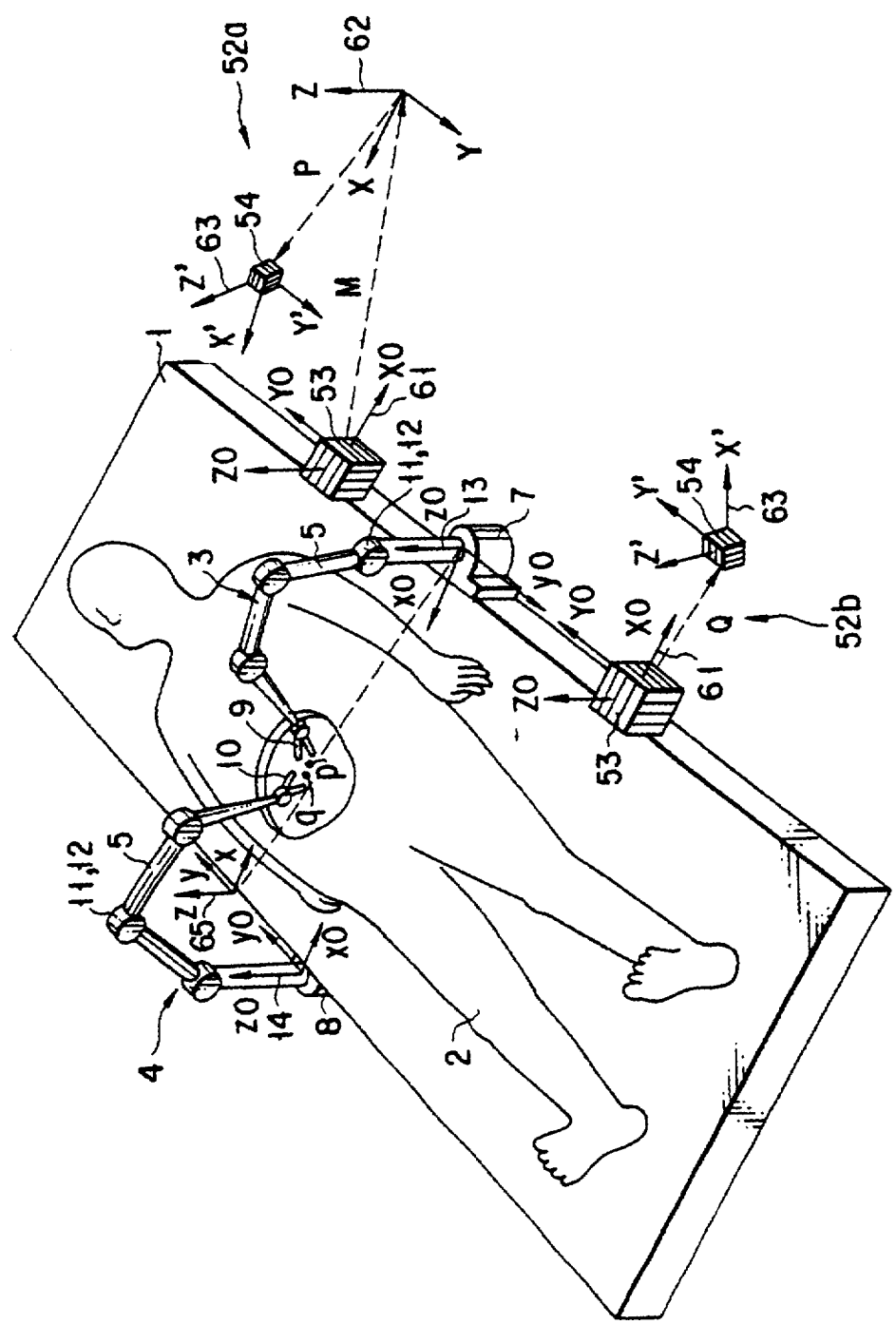
Figure 16:
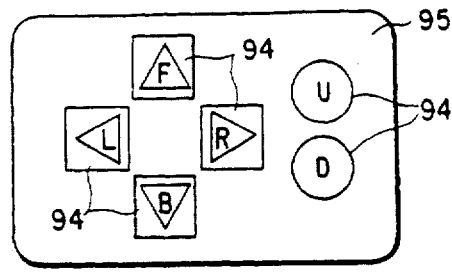
Figure 17:
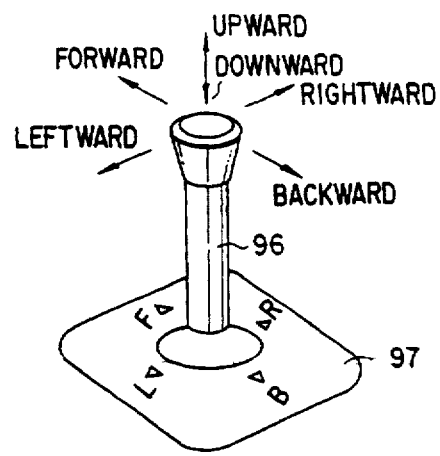
Figure 18A:
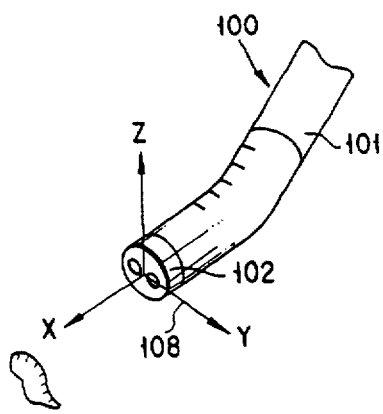
Figure 18B:
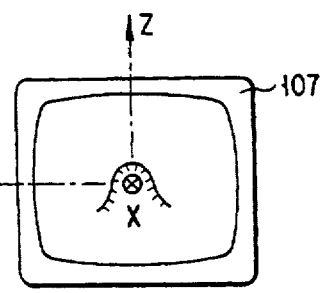
Figure 18C:
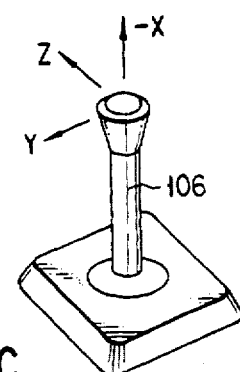
Figure 67A:
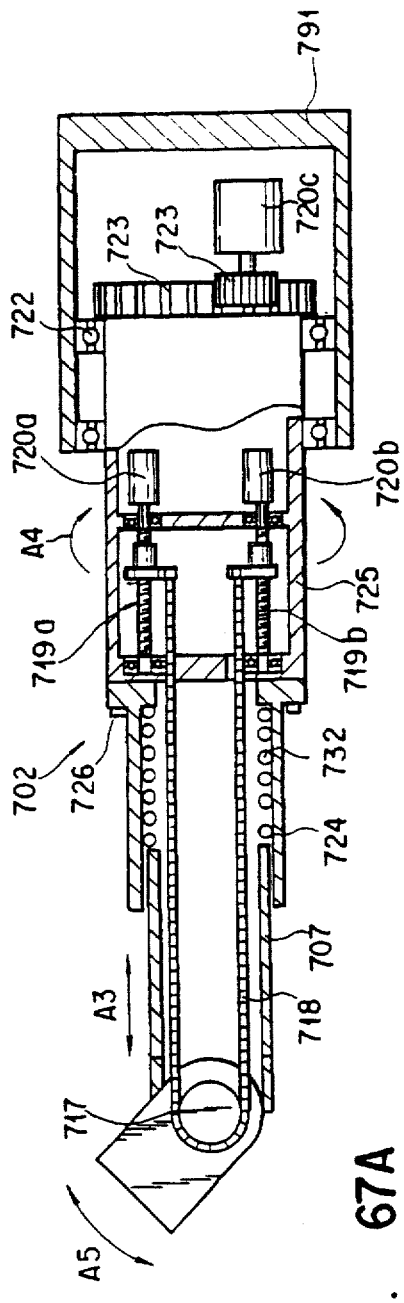
Figure 67B:
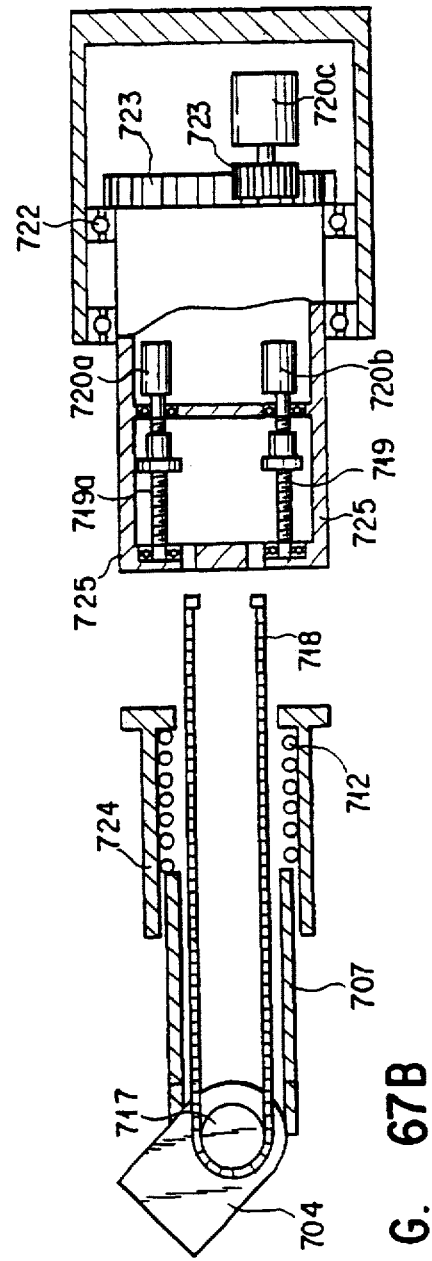

The second method of altering a task coordinate system will be explained, with reference to FIGS. 6 and 7. FIG. 6 is a perspective view of a manipulator 40 which is any one of the four manipulators 3, 4, 16 and 17 of the system shown in FIG. 1. FIG. 7 is a flow chart explaining the second method.

A matrix M for switching the base coordinate system of the manipulator 40 and the new task coordinate system 54 to be set in a space is expressed as:

$$M = \begin{bmatrix} n_x & o_x & a_x & p_x \\ n_y & o_y & a_y & p_y \\ n_z & o_z & a_z & p_z \\ o & o & o & o \end{bmatrix} \quad (A)$$

where $p(p_x,p_y,p_z)$, $o(o_x,o_y,o_z)$, $a(a_x,a_y,a_z)$, and $n(n_x,n_y,n_z)$ are the vector, close vector, directive vector and normal vector of the origin of the coordinate system, respectively.

These variables can easily be calculated from the relation between the actual position of the manipulator 40 and the position the manipulator 40 assumes in the task coordinate system 45. More specifically, the components n, o, a and p of the coordinate-switching matrix M are set in a register of the MPU incorporated in the controller for the manipulator 40. Then, the coordinate-switching matrix M is obtained in accordance with the formula (A). Then, the position vector Q of the TCP in the task coordinate system 45 is obtained by multiplying the position vector P of the TCP in the base coordinate system 41, which is known, from the left, by a coordinate matrix $M^{-1}$. Thus, $Q=M^{-1}P$.

Third Method

Figure 8:
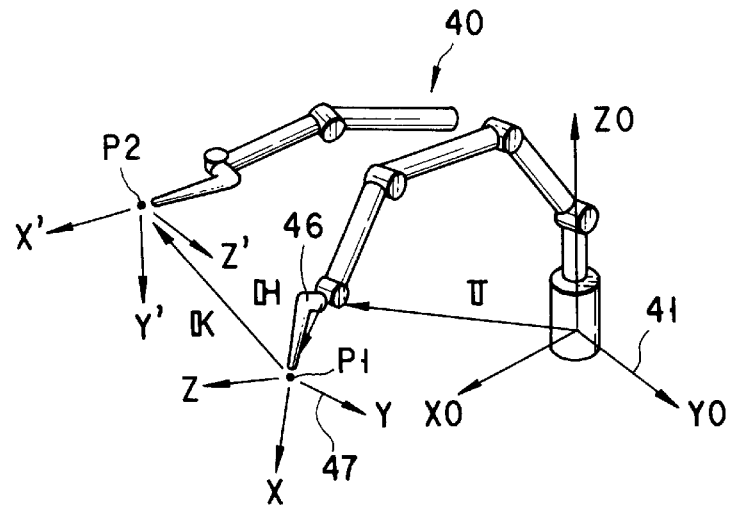
FIG. 8 is a perspective view of a manipulator, for explaining a third method of altering the coordinate system of each of the manipulators incorporated in the system shown in FIG. 1.
Figure 9:
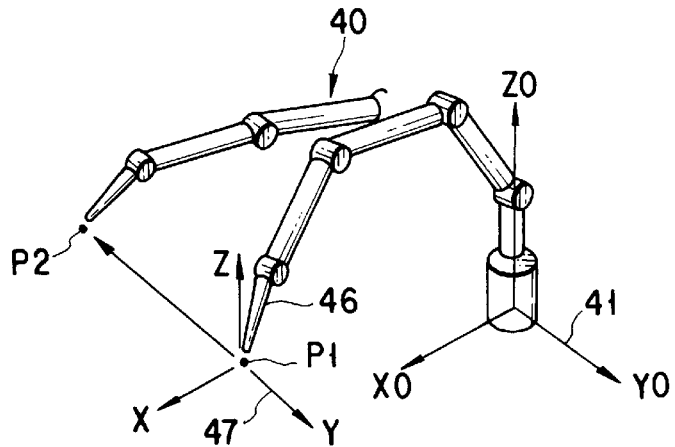
FIG. 9 is another perspective view of the same manipulator that is shown in FIG. 8, for explaining the method of altering the coordinate system of the manipulator.
Figure 10:
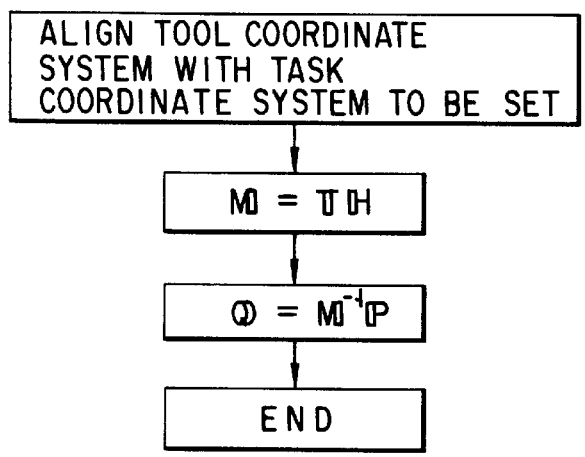
FIG. 10 is a flow chart explaining the third method of altering the coordinate system of the manipulator.

The third method of altering a task coordinate system will be explained, with reference to FIGS. 8, 9 and 10. FIGS. 8 and 9 are perspective views of a manipulator 40 which is any one of the four manipulators 3, 4, 16 and 17 of the system shown in FIG. 1. FIG. 10 is a flow chart explaining the third method.

First, there is defined a tool coordinate system 47. The tool coordinate system 47 is specific to the tool 46 mounted on the manipulator 40; its origin is always the TCP of the manipulator 40. This coordinate system 47 is orientated in a direction suitable for operating the manipulator 40 to perform surgery. Assuming that the tool 46 is an endoscope, the X axis of the tool coordinate system 47 is the axis of the endoscope, the Z axis of the system 47 extends in the offset direction of the endoscope, and the Y axis of the system 47 extend at right angles to the axis and the offset direction of the endoscope, respectively. To move the endoscope along its axis, it suffices to move the manipulator 40 along the x axis of the tool coordinate system 47.

The tool coordinate system 47 is represented by H T (=M), which is a mathematical notation of the matrix M for switching the base coordinate system 41. The notation of H T should be written, by rule, in bold type, but is printed in ordinary type here and hereinafter. T is a matrix for switching the coordinate system of the mechanical interface secured to the end effecter of the manipulator 40. H is a matrix for switching the tool coordinate system 47. The matrix T can be geometrically obtained from the lengths of the arms 43 constituting the manipulator 40 and the rotation angles detected by the encoders 44 provided at the joints among the arms 43. The matrix H is expressed by a formula similar to the formula (A). The variables for the components of the matrix H may be calculated from the shape of the tool used, and the orientation of the tool coordinate system 47. In order to find the position vector Q the TCP takes in the base coordinate system 14 which is known, it suffices to multiply the position vector P of the TCP in the base coordinate system 41, which is known, from the left, by a coordinate matrix $M^{-1}$.

The tool coordinate system 47 defined at a certain time is used as a task coordinate system to accomplish master-slave manipulation. For instance, the tool coordinate system 47 defined when the TCP of the manipulator 40 is located at a point P1 in a space is used as a task coordinate system. The tool coordinate system 47 is stored as the task coordinate system even after the manipulator 40 is operated, having its TCP shifted to a point P2 as shown in FIG. 8.

Next, a matrix Ks for switching the coordinate system of a slave manipulator is defined, and a matrix Km for switching the coordinate system of a master manipulator is defined, too. The slave manipulator is operated such that the coordinate-switching matrix Ks becomes identical to the coordinate-switching matrix Km. As a result, the master manipulator and the slave manipulator are moved, keeping their positional relationship unchanged since their task coordinate systems have been defined.

In other words, the slave manipulator moves in the same direction as the master manipulator. This is an advantage. Unless the slave manipulator is operated such that the coordinate-switching matrix Ks becomes identical to the coordinate-switching matrix Km, it is difficult to maintain the master manipulator in a specific positional relation with the slave manipulator—particularly in a so-called unilateral master-slave manipulator system. In the unilateral master-slave manipulator system, the master manipulator has encoders but no actuators at its joints, and the master manipulator often deviates from the desired positional relation with the slave manipulator. Once it has deviated from that positional relation, the master manipulator will move in a direction the surgeon cannot expect at all.

The second embodiment of the present invention will now be described, with reference to FIGS. 11 to 14. The second embodiment is characterized in that a manipulator is moved in the same direction as a sensor (i.e., a remote-control means) is moved.

Figure 11:
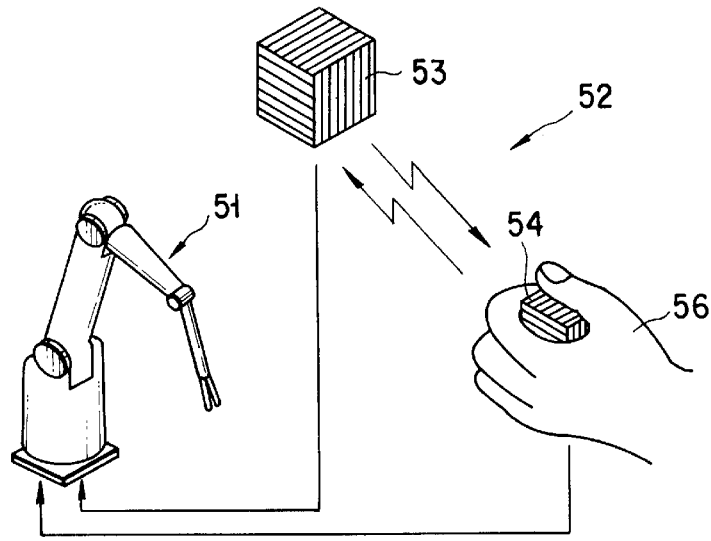
FIG. 11 is a schematic representation of the surgical manipulator system according to the second embodiment of the invention.

FIG. 11 is a schematic representation of the surgical manipulator system. As shown in FIG. 11, the system comprises a surgical manipulator 51 and a 3D position sensor 52. The manipulator 51 has a structure similar to the slave manipulators 3 and 4 incorporated in the first embodiment (FIG. 1). The manipulator 51 is secured to one side of an operating table and is controlled in the same way as either slave manipulator used in the first embodiment.

Figure 13:
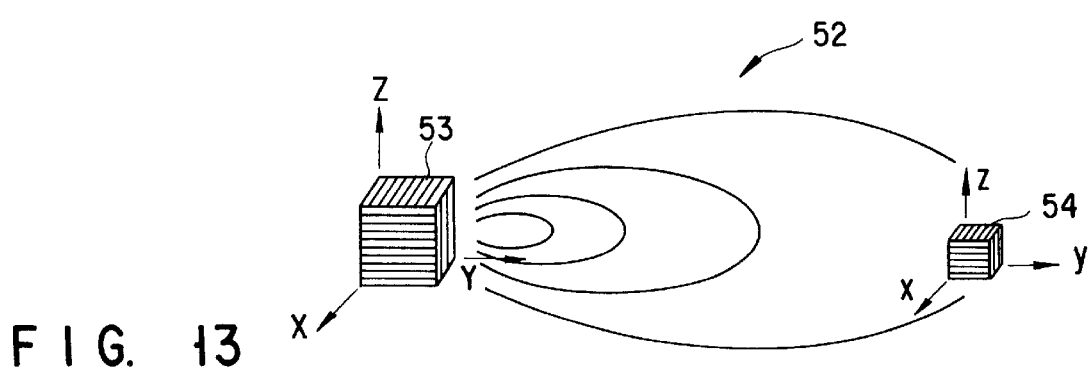
FIG. 13 is a diagram explaining the operation of the surgical manipulator system shown in FIG. 11.

The 3D position sensor 52 is one designed to remote-control a manipulator, and is used to remote-control the surgical manipulator 51. To state more precisely, the sensor 52 comprises a source coil 53 and a sense coil 54. Either coil is substantially a cube and has three coil elements wound around three orthogonal axes, for generating and receiving magnetic fields. A drive circuit (not shown) supplies pulse currents, one after another, to the coil elements of the source coil 53. The three coil elements of the source coil 53 generate three reference magnetic fields in the space occupied by the surgical manipulator system, as shown in FIG. 13. Hence, the coil elements constitute a transmitting section. The sense coil 54 detects the reference magnetic fields generated by the source coil 53 and determines its own position and orientation. Hence, the sense coil 54 functions as a receiving section.

Both coils 53 and 54, or at least the sense coil 54 is small enough to be gripped with the hand 56 as illustrated in FIG. 11. Alternatively, at least the sense coil 54 is small enough to be mounted on a part of a body, for example, the head. The sense coil 54 may be fixed to the HMD (Head Mounted Display) which the surgeon wears, so that the slave manipulator may be operated as the surgeon's head moves.

Figure 12:
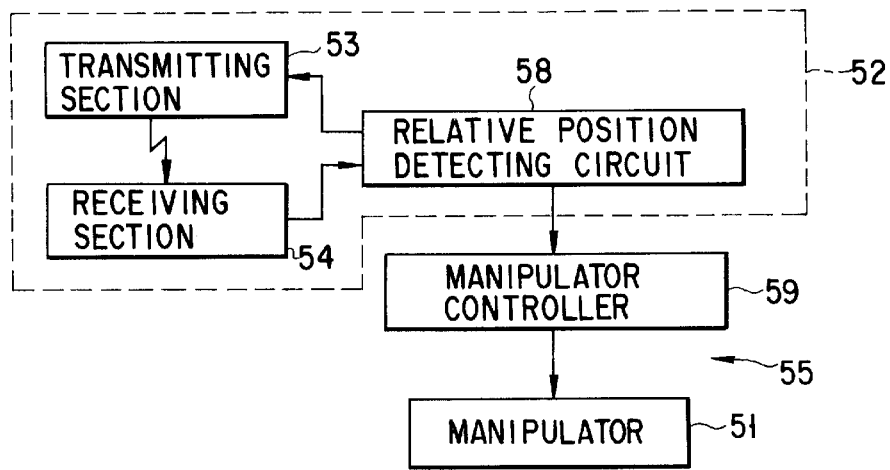
FIG. 12 is a block diagram showing the controller used in the surgical manipulator system of FIG. 11.

As indicated above, the 3D position sensor 52 comprises the source coil 53 operating as a section for transmitting magnetic fields and the sense coil 54 functioning as a section for receiving the magnetic fields generated by the source soil 53. As shown in FIG. 12, the sensor 52 further comprises a relative position detecting circuit 58 for detecting the position and orientation of the sense coil 54, both relative to the source coil 53. Provided outside the sensor 52 is a manipulator controller 59. The controller 59 is designed to remote-control the surgical manipulator 51 in accordance with the relative 3D position detected by the coils 53 and 54 of the 3D position sensor 52. The 3D position sensor 52 and the manipulator controller 59 constitute a remote-control system for controlling the manipulator 51. The 3D position sensor 52 and the manipulator controller 59 constitute a remote-control system 55.

When the sense coil 54 receives the reference magnetic fields emanating from the source coil 53, currents are induced in the coil elements of the sense coil 54, flowing along the axes of the coil elements, as is illustrated in FIG. 13. The relative position detecting circuit 58 detects the vectors of the magnetic fields and calculates the relative 3D positions of the coils 53 and 54 from the vectors of the magnetic fields.

The 3D position sensor 52 transmits data representing the relative 3D positions of the coils 53 and 54 to the manipulator controller 59. The controller 59 remote-controls the manipulator 51 in accordance with the 3D position of the sense coil 54 relative to the source coil 53, which has been detected by the 3D position sensor 52.

Figure 14:
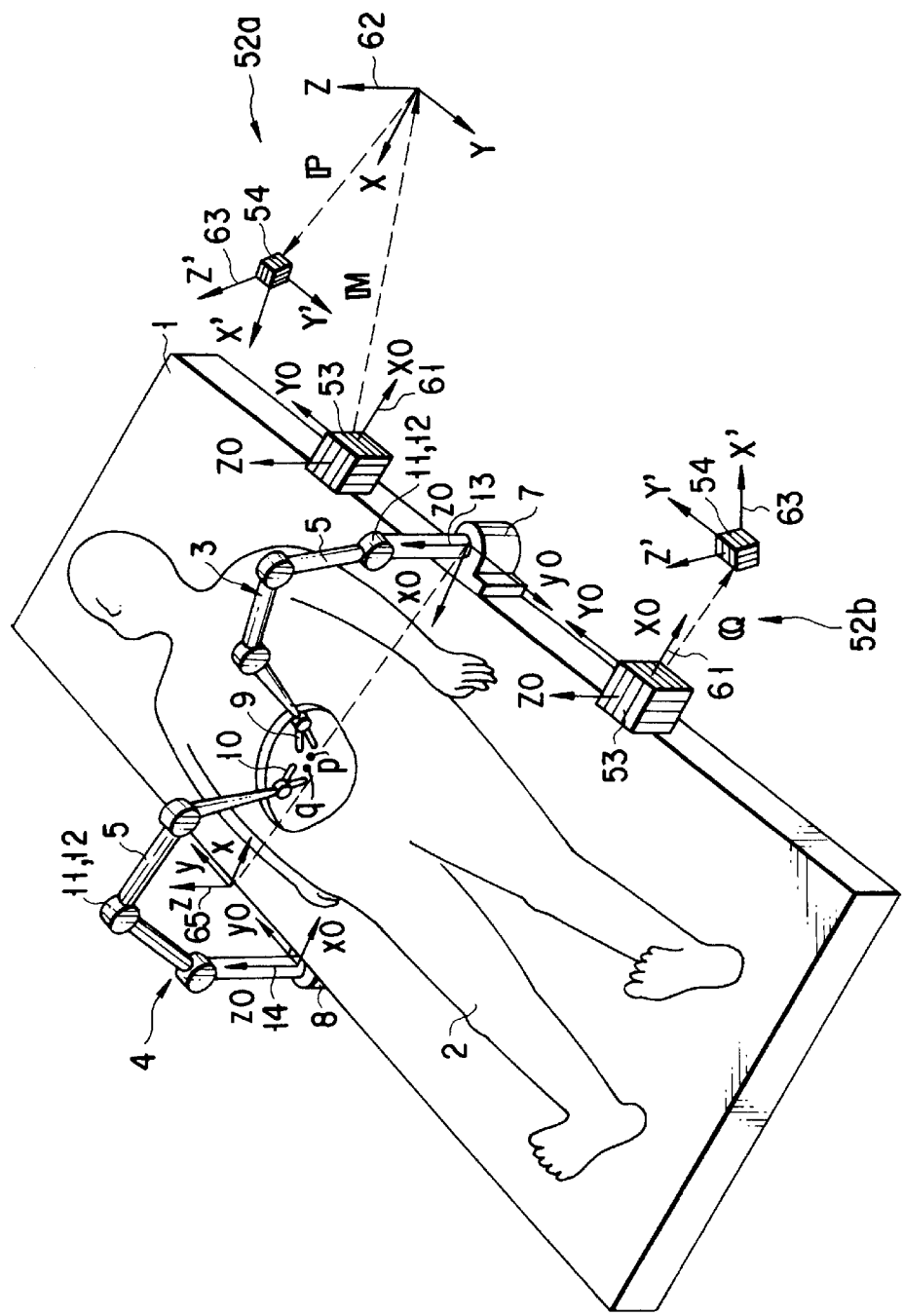
FIG. 14 is a perspective view for explaining how the system of FIG. 11 is used to perform surgery.

The remote-control system 55 can be applied to the first embodiment, i.e., the surgical manipulator system shown in FIG. 1—as illustrated in FIG. 14. As shown in FIG. 14, two slave manipulators 3 and 4 are secured at their bases 7 and 8 to the right and left sides of an operating table 1, respectively. Two source coils 53, each functioning as a transmitting section, are secured to the right side of the operating table 1. Two sense coils 54, each functioning as a receiving section, are held in the hands of a surgeon or attached to the head band the surgeon wears. The first source coil 53 and the first sense coil 54 constitute a first 3D position sensor 52a. The second source coil 53 and the second sense coil 54 constitute a second 3D position sensor 52b.

The first slave manipulator 3 is operated in accordance with the relative 3D positions of the coils 53 and 54 of the first position detector 52a. A task coordinate system 62 is set, in addition to the base coordinate system 61 of the first 3D position sensor 52a. The slave manipulator 3 is operated such that the vector P representing the position which the sensor coordinate system 63 set for the sense coil 54 and assumes in the task coordinate system 62 coincides with the vector p representing the position which the TCP of the first slave manipulator 3 takes in the base coordinate system 13 set for the first slave manipulator 3. The task coordinate system 62 can be freely altered, by using the sensor coordinate system 63 (an orthogonal coordinate system) set for the sense coil 54. For example, a sensor coordinate system 63 set at a time may be used as the task coordinate system 62.

Once the task coordinate system 62 has been set at any desired position, the base coordinate system 13 of the slave manipulator 3 (in which the TCP is present) becomes identical in orientation to the task coordinate system 62 (in which the sensor coordinate system 63 exist). This makes it easy for the surgeon to operate the slave manipulator 3.

The second slave manipulator 4 is operated in accordance with the relative 3D positions of the coils 53 and 54 of the second position detector 52b. The second slave manipulator 4 is operated such that the vector Q representing the position which the sensor coordinate system 63 sets for the sense coil 54 and assumes in the base coordinate system 61 set for the second position detector 52b coincides with the vector q representing the position which the TCP of the second slave manipulator 4 takes in the task coordinate system 65 set freely for the second slave manipulator 4. The task coordinate system 65 can be freely altered, by the first or second method applied in the first embodiment. Once the task coordinate system 65 has been set, the vector Q and the vector q become identical in orientation as shown in FIG. 14. The surgeon can therefore operate the second slave manipulator 4 with ease.

The third embodiment of the invention will be described with reference to FIG. 15. The third embodiment is characterized in that the manipulators are operated in accordance with audio commands made by a surgeon.

Figure 15:
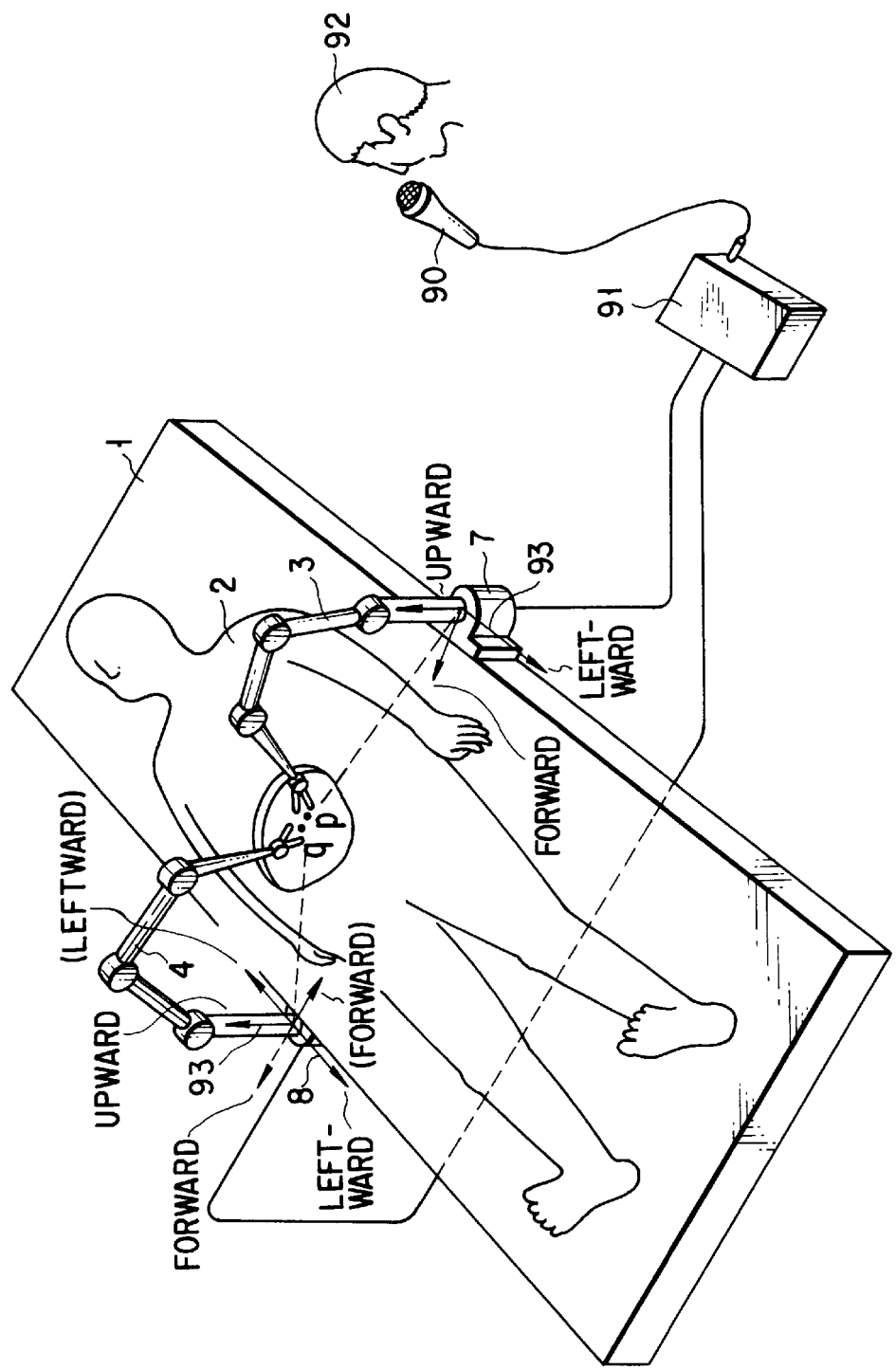
FIG. 15 is a perspective view showing the surgical manipulator system according to the third embodiment.

FIG. 15 is a perspective view showing the surgical manipulator system according to the third embodiment. As shown in FIG. 15, the surgical manipulator system comprises a speech input device 90, and a speech recognition device 91, two slave manipulators 3 and 4. The system further comprises a manipulator controller, which is not shown.

When a surgeon 92 utters an audio command, a word such as "forward," "backward," "upward," "downward," "leftward" or "rightward," to the speech input device 90 (e.g., a microphone), the speech recognition device 91 analyses the audio command and generates command data. The command data is supplied to the manipulator controller (not shown).

The slave manipulators 3 and 4 are secured at their bases 7 and 8 to the right and left sides of an operating table 1. For each slave manipulator there is set a base coordinate system 93 which has an up-down axis, a left-right axis and a forward-backward axis. The base coordinate systems can be altered by any one of the methods described above, such that they are orientated to the direction in which the surgeon 92 looks at the TCPs of the slave manipulators 3 and 4.

Usually, the base coordinate system 93 preset for the first slave manipulator 3 is orientated in such a manner that the three axes indicate the up-down, left-right and forward-backward directions—all exactly the same as the three directions the surgeon 92 perceives with respect to the TCP of the manipulator 3. It is therefore unnecessary to alter the base coordinate system 93 of the first slave manipulator 3.

On the other hand, the base coordinate system 93 preset for the second slave manipulator 4 is orientated such that the left-right axis and the forward-back axis indicate the left-right and forward-backward directions opposite to those the surgeon 92 perceives with respect to the TCP of the manipulator 4, though the up-down axis indicates the same up-down direction as the surgeon 92 perceives with respect to that TCP. This is inevitably because the second slave manipulator 4 is secured to the left side of the operating table 1 and located opposite to the first slave manipulator 3. Consequently, the audio commands of "leftward," "rightward," "forward" and "backward" made by the surgeon 92 cannot be applied to the operation of the second slave manipulator 4.

In order to operate the second slave manipulator 4 correctly in accordance with any audio command the surgeon 92 issues, the base coordinate system 93 of the manipulator 4 is altered to orient the left-right and the forward-backward axes as indicated by broken-line arrows in FIG. 15. To accomplish this alteration it suffices to rotate the horizontal plane of the base coordinate system 93 by 180°. Once the base coordinate system 93 of the manipulator 4 has been so altered, it is quite easy for the surgeon 92 to operate the second slave manipulator 4, as well as the first slave manipulator 3.

Figure 16:
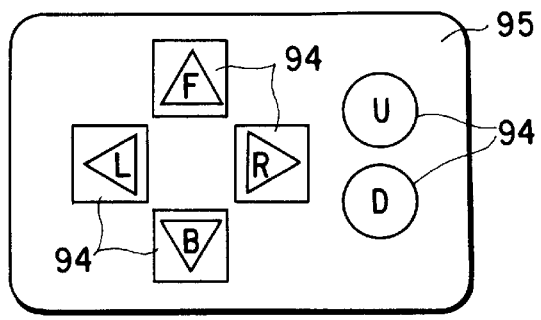
FIG. 16 is a plan view of a console used as a command input device.
Figure 17:
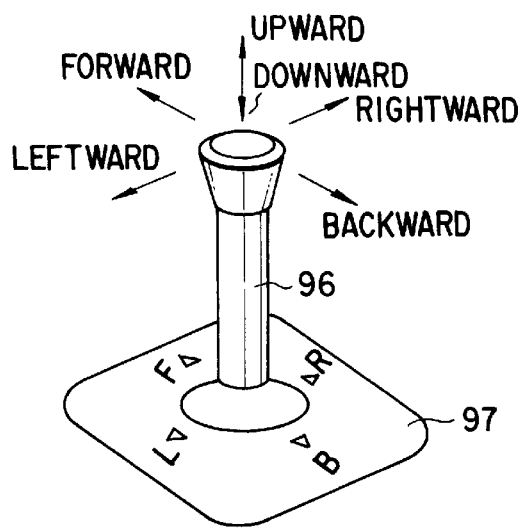
FIG. 17 is a perspective view of a console having a joystick, used as a command input device.

In the third embodiment, the slave manipulators 3 and 4 are moved in various directions in the base coordinate systems 93 in accordance with the corresponding audio commands the surgeon 92 makes. Instead, commands may be generated by operating a console 96 shown in FIG. 16, which has six switches 94, i.e., an "upward" switch, a "downward" switch, a "leftward" switch, a "rightward" switch, a "forward" switch and a "backward" switch. Alternatively, commands may be generated by operating a console 97 shown in FIG. 17, which has a joystick 96.

The fourth embodiment of this invention will be described with reference to FIGS. 18A, 18B and 18C and FIGS. 19A and 19B.

Figure 18A:
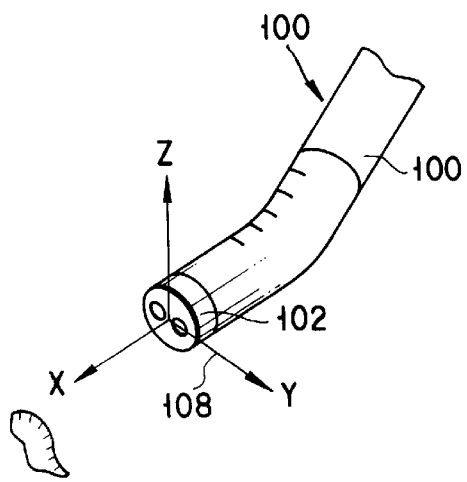
FIGS. 18A, 18B and 18C show three major components of the surgical manipulator system according to the fourth embodiment of the present invention.

The fourth embodiment comprises a manipulator 100 shown in FIG. 18A. The manipulator 100 has an insertion section 101 which is to be inserted into a body cavity. The insertion section 101 has an observation device 102 in its distal end. The observation device 102 is used to generate signals representing an image of the interior of the body cavity. The device 102 is, for example, a 3D scope 103 shown in FIG. 19A or an ultrasonic probe 105 shown in FIG. 19B which contains an ultrasonic transducer 104.

Figure 18B:
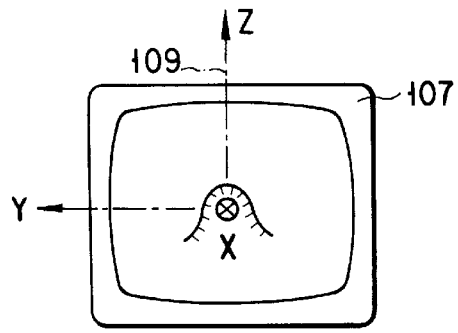
Figure 18C:
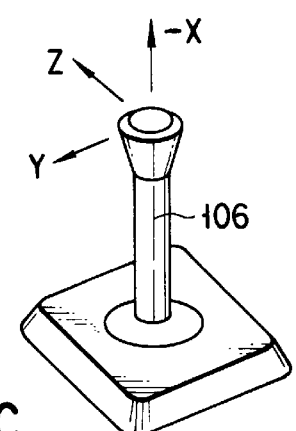

The fourth embodiment further comprises a joystick 106 and a TV monitor (display) 107 which are shown in FIGS. 18C and 18B, respectively. The joystick 106 is used to remote-control the manipulator 100. The TV monitor 107 is provided to display the image obtained by the observation device 102.

A fixed tool coordinate system 108 is set at the distal end of the observation device 102. In this tool coordinate system 108, the distal end of the insertion section 101 of the manipulator 100 is moved as the joystick 106 is operated along the X axis, Y axis and Z axis. The tool coordinate system set for the joystick 106 can be altered by any one of the methods described above.

The tool coordinate systems of the joystick 106 and the TV monitor 107 are adjusted to become identical in orientation. Hence, as the joystick 106 is operated in any direction, thus moving the distal end of the insertion section 101, an object displayed on the TV monitor 107 moves in the same direction. This enhances the operability of the surgical manipulator system.

The fifth embodiment of the invention, which is a surgical manipulator system, will be described with reference to FIGS. 20 and 21.

This surgical manipulator system comprises a manipulator 110, an HMD 115 and a source coil 118. As shown in FIG. 21, the manipulator 110 has an insertion section 111 and an observation device 112 contained in the distal end of the insertion section 111. Like its counterpart of the fourth embodiment, the observation device 112 is, for example, a 3D scope 103 shown in FIG. 19A or an ultrasonic probe 105 shown in FIG. 19B which contains an ultrasonic transducer 104.

As shown in FIG. 20, the HMD 115 is worn by a surgeon 116 who operates the surgical manipulator system. The HMD 115 comprises a head band and a sense coil 117 attached to the head band. The position of the surgeon's head is detected from the positional relation which the sense coil 117 assumes with the source coil 118. Thus, the sense coil 117 and the source coil 118 constitute a device for detecting the motion of the head of the surgeon 116. In accordance with the motion of the head, the manipulator 110 is moved in the same manner. The coordinate system of the head can be altered to have the same orientation as the coordinate system of the manipulator 110, or vice versa, so that the surgeon 116 may perform successful surgery.

A fixed tool coordinate system 119 is set for the observation device 112 contained in the distal end of the insertion section 111. Sensor coordinate systems 121 and 122 are set for the sense coil 117 and the source coil 118, respectively. The 3D position relation between the sense coordinate systems 121 and 122 is calculated in the form of a matrix M for switching a sensor coordinate system, from the sensor coordinate system 121 to the sensor coordinate system 122.

It is inconvenient if the manipulator 110 is operated in the same way as the surgeon 116 moves his or her head, as in the case where the surgeon 116 puts on or takes off the HMD 115 or where the manipulator 110 must be kept in the same position. To cope with such cases, the system may be equipped with a changeover switch for enabling the manipulator 110 to move or prohibiting the manipulator 110 from moving, as the surgeon 116 moves his or her head, thus moving the HMD 115.

Assume that the changeover switch has been operated, enabling the manipulator 110 to move as the head moves. In this case, the manipulator 110 can be moved such that the matrix P for switching the sensor coordinate system 121 set the moment the changeover switch has been so operated, to the present sensor coordinate system 121', coincides with the matrix Q for switching the tool coordinate system 119 set the moment the changeover switch has been so operated, to the present tool coordinate system 119'. No discrepancy therefore exists between the directions in which the head and the HMD 115 move at the time of operating the changeover switch.

The sixth embodiment of the present invention will be described with reference to FIGS. 22A and 22B.

The sixth embodiment comprises a surgical manipulator 110 shown in FIG. 22A, an HMD 115 shown in FIG. 22B and a manipulator 127 shown in FIG. 22B. The surgical manipulator 110 is identical to the manipulator (FIG. 21) incorporated in the fifth embodiment. The HMD 115 is of the same type as the HMD (FIG. 20) used in the fifth embodiment; it is provided to display an image obtained by the observation device 112 which is contained in the distal end of the insertion section 111 of the manipulator 110.

The manipulator 127 is secured at an upper end to the ceiling of an operating room. The HMD 115 is connected to the lower end of the manipulator 127. The manipulator 127 is a multi-joint one, comprising a plurality of arms 126 and encoders 128 provided at the joints among the arms 126. As the surgeon 116 moves his or her head, the arms 126 of the manipulator 127 are rotated. The encoders 128 detect the rotation angles of the arms 126. The position the HMD 115 takes in space is calculated from the rotation angles detected by the encoders 128. In accordance with the position of the HMD 115, the surgical manipulator 110 is operated in the same manner as the surgeon 116 moves his or her head. A fixed tool coordinate system 119 is set at the distal end of the observation device 112, and a fixed sensor coordinate system 121 is set for the HMD 115.

It is inconvenient if the manipulator 110 is operated in the same way as the surgeon 116 moves his or her head, as in the case where the surgeon 116 puts on or takes off the HMD 115 or where the manipulator 110 must be kept in the same position. To cope with such cases, the sixth embodiment is equipped with a changeover switch for enabling the manipulator 110 to move or prohibiting the manipulator 110 from moving, as the surgeon 116 moves his or her head, thus operating the manipulator 127.

Assume that the changeover switch has been operated, enabling the manipulator 110 to move as the head moves. In this case, the manipulator 110 can be moved such that the matrix P for switching the sensor coordinate system 121 set the moment the changeover switch has been so operated, to the present sensor coordinate system 121', coincides with the matrix Q for switching the tool coordinate system 119 set the moment the changeover switch has been so operated, to the present tool coordinate system 119'. There is no discrepancy between the directions in which the head and the HMD 115 move at the time of operating the changeover switch.

The seventh embodiment of this invention will be described with reference to FIGS. 23 and 24. The seventh embodiment is characterized in that an observation manipulator 133 and a TV monitor 135 are used to enhance the operability of a surgical manipulator 130.

As shown in FIG. 23, a tool coordinate system 131 is set at the distal end of the surgical manipulator 130, such that its x axis aligns with the longitudinal axis of the surgical manipulator 130. An observation device 134 is provided in the distal end of the observation manipulator 133. The device 134 which scans the surgical manipulator 130 system according to the seventh embodiment comprises a surgical manipulator 130 and generates a signal representing the image of the manipulator 130. The signals are supplied to the TV monitor 135 shown in FIG. 24, whereby the image of the surgical manipulator 130 is displayed on the screen of the TV monitor 135. The TV monitor 135 displays the tool coordinate system 131, too, superimposed on the image of the surgical manipulator 130.

The seventh embodiment comprises a controller for moving the surgical manipulator 130 along the three axes of the tool coordinate system 131. As the manipulator 130 is moved, its image on the screen of the TV monitor 135 moves in the same way. Hence, a surgeon can operate the controller, thus moving the manipulator 130 in various manners, while looking at the image of the surgical manipulator 13 moving on the screen of the TV monitor 135.

The eighth embodiment of the invention will be described with reference to FIGS. 25A, 25B and 25C. This embodiment is a surgical manipulator system having a slave manipulator 151 and a master manipulator 161.

As shown in FIG. 25B, the slave manipulator 151 comprises a surgical unit 153 and a robot 154. The unit 153 has an insertion section 152, the distal end portion of which is to be inserted into a body cavity. The robot 154 has a plurality of axes and can rotate the insertion section 152 and extends the section 151 back and forth. As illustrated in FIG. 25C, the slave manipulator 151 further comprises a 3D scope 155 and a pair of instruments 156 and 157. The 3D scope 155 is provided in the distal end of the insertion section 152. Both instruments 156 and 157 extend through the insertion section 152 and protrude forward from the distal end thereof. The instruments 156 and 157 can be bent in two or more degrees of freedom.

The master manipulator 161 is a multi-joint one and serves as controller for remote-controlling the slave manipulator 151. It is secured at its upper end to the ceiling of an operating room. Connected to its lower end are a HMD 162 and a pair of operation arms 163 and 164. The operation arms 163 and 164 are associated with the instruments 157 and 156 which protrude from the distal end of the insertion section 152. A coordinate system is set for either arm, so that the surgeon may operate the arm to remote-control the instrument (157 or 156) associated with the arm.

More specifically, five coordinate systems are set for the 3D scope 155, the instruments 156 and 157 and the operation arms 163 and 164, respectively. When the surgeon operates the master manipulator 161 in the tool coordinate system 165 set for the master manipulator 161, the insertion section 152 of the slave manipulator 151 is operated in the same way in the tool coordinate system 166 set for the slave manipulator 161. The slave manipulator 151 is operated, such that the sensor coordinate system 167 set for the HMD 162 with respect to the tool coordinate system 165 corresponds to the scope coordinate system 170 set for the 3D scope 155 with respect to the tool coordinate system 166. The control coordinate systems 168 and 169 are set for the operation arms 163 and 164 with respect to the tool coordinate system 165, so that they correspond to the instrument coordinate systems 171 and 172 set for the instruments 156 and 157 with respect to the tool coordinate system 166. Therefore, the 3D scope 155 and the instruments 156 and 157 can be operated in good coordination, though they are controlled independently.

Figure 26:
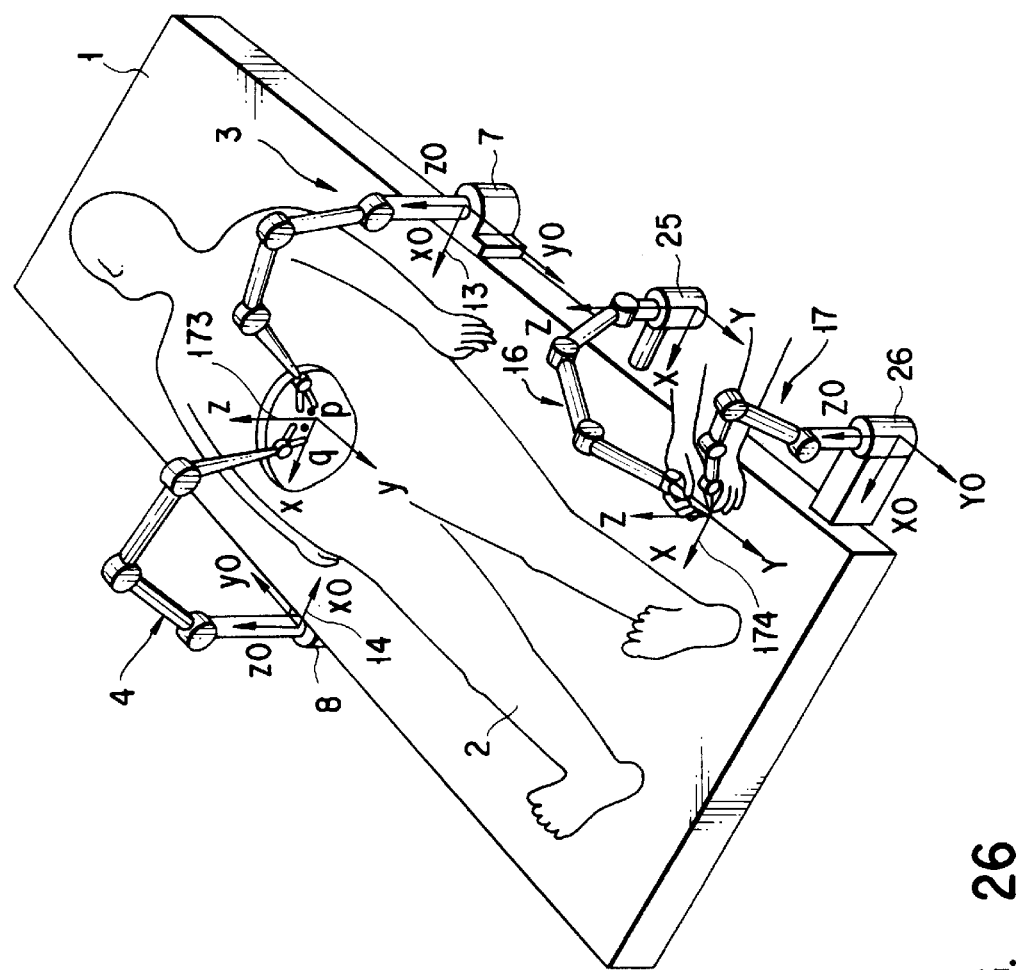
FIG. 26 is a perspective view showing the surgical manipulator system according to the ninth embodiment of this invention.

The ninth embodiment of the present invention will be described with reference to FIG. 26. The ninth embodiment is a modification of the first embodiment. The ninth embodiment comprises two slave manipulators 3 and 4 and two master manipulators 16 and 17. The slave manipulators 3 and 4 are secured to the right and left sides of an operating table 1. The master manipulators 16 and 17, which remote-control the slave manipulators 3 and 4, respectively, are secured to the same side (i.e., right side) of the operating table 1, not to a console as in the first embodiment (FIG. 1). Hence, the first slave manipulator 3 and the first master manipulator 16, which are associated, are located at the same side of the operating table 1, whereas the second slave manipulator 4 and the second master manipulator 17, which are associated, are located at the opposite sides of the operating table 1.

Since the second slave manipulator 4 opposes the second master manipulator 17, across the operating table 1, its base coordinate system differs in orientation from the base coordinate system of the second master manipulator 17. Consequently, when a surgeon moves the second master manipulator 17, the second slave manipulator 4 is moved in a different direction, as has been explained in conjunction with the first embodiment.

To operate the slave manipulators 3 and 4 in the same way as the second master manipulators 16 and 17, respectively, one task coordinate system 173 is set for both slave manipulators 3 and 4, and one task coordinate system 174 is set for both master manipulators 16 and 17. This measure taken, the operability of the surgical manipulator system can be improved, no matter how many master-slave sets of manipulators are provided and no matter where the slave manipulators are arranged with respect to the associated master manipulators. Namely, the ninth embodiment solves the problem which arises in the case where, as in most surgical manipulator systems, the master and slave manipulators are so arranged with respect to the patient that they cannot have identical base coordinate systems.

As in the ninth embodiment, master manipulators may be provided in the same number as the slave manipulators used. Instead, less master manipulators may be provided than slave manipulators. If this is the case, one master manipulator is associated with a plurality of slave manipulators. For instance, the ninth embodiment may have only one master manipulator 16 for remote-controlling both slave manipulator 3 and 4. In this case, a slave-switching device is operated to select the slave manipulator 3 or the slave manipulators 4 so that the selected slave manipulator may be remote-controlled when the master manipulator 16 is operated.

Figure 27:
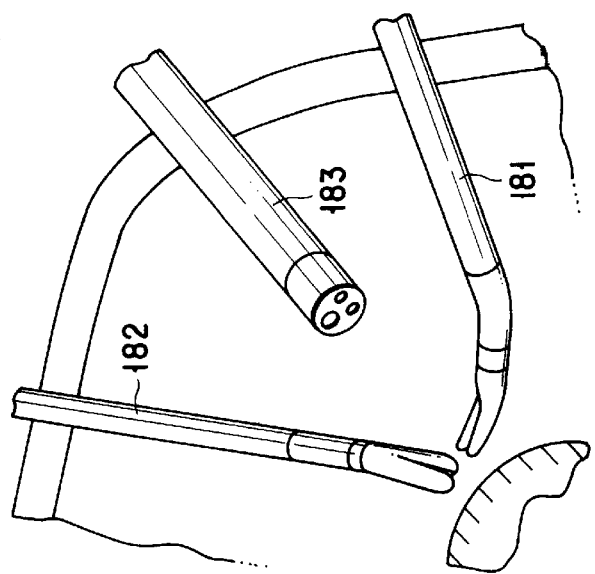
FIG. 27 is a perspective view, explaining how the surgical manipulator system according to the tenth embodiment of the invention is operated to perform a transcutaneous surgery.

The tenth embodiment of this invention will be described with reference to FIG. 27. This embodiment comprises two slave manipulators 181 and 182 and an endoscope 183. A surgeon inserts the manipulators 181 and 182 and the endoscope 183 into a body cavity through an incision made in the body wall. He or she then performs a transcutaneous surgery, by operating two master manipulators (not shown) of the same type as used in the first embodiment (FIG. 1), thereby remote-controlling both slave manipulators 181 and 182, while watching the interior of the body cavity through the endoscope 183.

In the first to tenth embodiments described above, the coordinate systems set for the surgical manipulators or the coordinate system set for the means for remote-controlling the surgical manipulators, or all these coordinate systems, can be altered to align in terms of orientation. As a result, the surgical manipulators are moved in the same direction as a surgeon moves the remote-control means, overcoming the restriction imposed in the case where the coordinate systems of the surgical manipulators differ in orientation from the coordinate system of the remote-control means. In other words, the surgical manipulators can be operated in the same manner as the surgeon operates the remote-control means, whichever positions the surgical manipulator take with respect to the remote-control means.

The eleventh embodiment of this invention will be described, with reference to FIG. 28, FIGS. 29A and 29B, FIGS. 30A and 30B, FIGS. 31A and 31B, FIG. 32, FIG. 33 and FIGS. 34A to 34C.

As shown in FIG. 28, the eleventh embodiment, or a surgical manipulator system 230, comprises a slave manipulator 201, an HMD 208, a master arm 209 and a controller 207.

The slave manipulator 201 is designed to be inserted into a body cavity to perform a physical action on an object of surgery which exists in the body cavity. The slave manipulator 201 comprises a multi-joint arm 202, a gripper 203, a touch sensor 204, a drive section 205 and a 3D scope 206. As shown in FIG. 31B, the gripper 203 is attached to the distal end of the multi-joint arm 202. As shown in FIG. 28, the sensor 204 is attached to the gripper 203. The drive section 205 is provided to drive the multi-joint arm 202, rotating the joints of the arm 202 by various angles so that the arm 202 is bent in a desired fashion. As is shown in FIG. 31B, the 3D scope 206 is located near the multi-joint arm 202, for providing a 3D image of the interior of the body cavity.

The controller 207 is provided to control the slave manipulator 201 and to process the left-eye image signal and the right-eye image signal generated by the 3D scope 206. The HMD 208 is designed to receive the image signals processed by the controller 270 and display the left-eye image and right-eye image of the interior of the body cavity. The master arm 209 functions as remote-control means for causing the controller 207 to drive the slave manipulator 201.

Figure 31A:
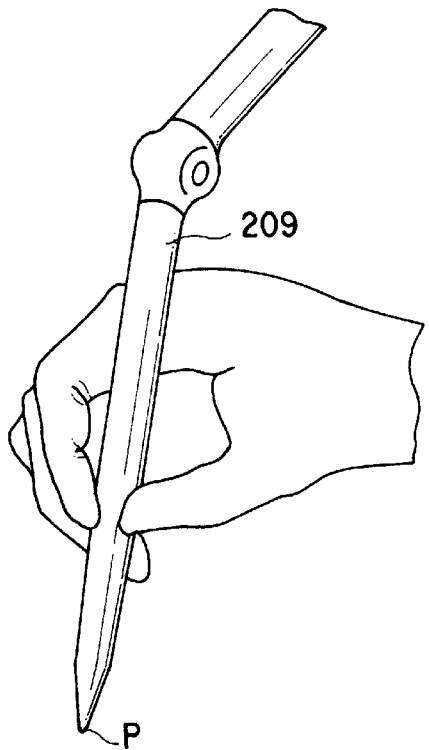
FIG. 31A is a perspective view of the master arm incorporated in the eleventh embodiment.
Figure 31B:
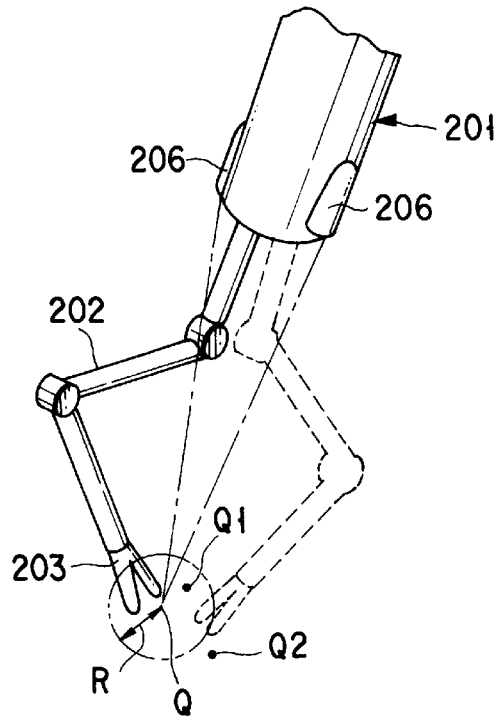
FIG. 31B is a perspective view of the slave manipulator used in the eleventh embodiment.

The master arm 209 is operated by a surgeon as illustrated in FIG. 31A. As the surgeon operates the master arm 209, the controller 207 calculates the position which the multi-joint arm 202 should take to perform surgery in the body cavity.

Figure 32:
FIG. 32 is a diagram explaining how to operate two master arms.

The surgical manipulator system 230 may have two or more slave manipulators, instead of only one, and the system 230 has as many master arms. For example, in the case where the system 230 has two slave manipulators, the system 230 has two master arms 209 as shown in FIG. 32. In this instance, the surgeon 210 operates both master arms 209 as shown in FIG. 32, while looking at a 3D image of the interior of a body cavity which is displayed by the HMD 208 he or she wears.

As illustrated in FIG. 29B, the 3D scope 206 has, in its distal end, two objective optical systems 209a and 209b and two CCDs 210a and 210b. The optical systems 209a and 209b are arranged, each having a convergence angle with respect to the object present in the body cavity. The first CCD 210a receives a left-eye optical image which the first objective optical system 209a has formed, and converts the left-eye optical image into a left-eye image signal. The second CCD 210b receives a right-eye optical image which the second objective optical system 209b has formed, and converts the right-eye optical image into a right-eye image signal. The two image signals are supplied to the controller 207.

The objective optical systems 209a and 209b have one variable focal-point unit (not shown) each. The unit may be a combination lens unit which has one optical axis and which focuses an optical image onto a CCD by means of pupil division. The variable focal-point unit adjusts the focal distance under the control of the controller 207.

As shown in FIG. 28, the controller 207 comprises a signal processing circuit 211, an arithmetic processing unit 214 and a control circuit 217.

The signal processing circuit 211 receives the left-eye image signal and the right-eye image signal from the CCDs 210a and 210b, and processes these signals into video signals of standard type. The video signals are supplied to the HMD 208. As shown in FIG. 29A, the HMD 208 has two display sections 208a and 208b, which display the left-eye image and the right-eye image, respectively. The surgeon 210 sees these images with his or her left eye 212a and 212b, thereby perceiving a 3D image of the object 232 present in the body cavity. That is, the objective optical systems 209a and 209b receive the real image of the object 232 with parallax as shown in FIG. 29B, and the display sections 208a and 208b of the HMD 208 display the left-eye and right-eye images of the object 232, respectively, with parallax. Seeing these images with the left and right eyes, the surgeon 210 perceives a 3D virtual image 232' of the object 232.

As illustrated in FIG. 29A, the HMD 208 has sensors 213a and 213b for detecting the orientations of the optical axes of the surgeon's eyes 212a and 212b, respectively. These sensors 213a and 213b are connected to the arithmetic processing unit 214 of the controller 207. The arithmetic processing unit 214 comprises a position calculating circuit 215 and a displacement calculating circuit 216. The circuit 215 receives the signals output from the sensors 213a and 213b and representing the orientations of the optical axes of the eyes 212a and 212b, and calculates the position of the object 232 from these signals. The circuit 216 compares the position of the object 232, calculated by the circuit 215, with the position thereof, indicated by the master arm 209, thereby finding a deviation between the position of the object 232 and that of the TCP which the surgeon 210 has indicated by operating the gripper 203. The circuit 215 generates a signal representing the deviation.

The position calculating circuit 215 generates a signal representing the position of the object 232 it has detected. This signal is supplied to the 3D scope 206 of the slave manipulator 201, controlling both variable focal-point units of the 3D scope 206. Namely, the circuit 215 achieves so-called automatic focusing.

The displacement calculating circuit 216 supplies the displacement signal to the control circuit 217. In accordance with the deviation signal the circuit 217 controls the drive section 205 of the slave manipulator 201. Thus controlled, the drive section 205 drives the multi-joint arm 202, whereby the TCP of the gripper 203 is moved to the TCP which the surgeon 210 has indicated by operating the master arm 209. The control circuit 217 is designed to stop the slave manipulator 201 when the pressure which the gripper 203 applies to the object 232 and which the touch sensor 204 detects increases above a preset value. As soon as the slave manipulator 201 is stopped, the gripper 203 is opened to release the object 232, for safety.

There are two types of sensors which can be used as the sensors 213a and 213b. The first type, shown in FIG. 30A, includes a CCD camera 218 for determining the position of the eye (212a or 212b) and the center of the pupil (221a or 221b) and subsequently detecting the orientation of the optical axis of the eye from the positional relation between the eye and the center of the pupil. The second type, shown in FIG. 30B, has a light-emitting diode 219 and a PSD (Position Sensing Device) 220. The light-emitting diode 219 emits an infrared beam to the eye (212a or 212b), and the PSD receives the beam reflected from the eye, to detect the orientation of the optical axis of the eye. Both types of sensors are known. "Photograph Industry," Shashin Kogyo, January 1993, pp. 63 and 64 and pp. 104 and 105 discloses a system wherein a microcomputer calculates the rotation angle of the eye from the positional relation between the pupil and an image formed by an infrared beam reflected from the cornea, thereby to determine the orientation of the optical axis of the eye.

While the surgeon 210 is observing the virtual image 232' of the object 232, the optical axes of his or her eyes 212a and 212 intersect with each other at the virtual image 232', as is illustrated in FIG. 29A. Hence, the position of the virtual image 232' can be determined from the orientations of the optical axes which the sensors 213a and 213b have detected. The position the object 232 assumes with respect to the 3D scope 206 is determined from the position of the virtual image 232' formed by the HMD 208, since the optical features of the HMD 208 and those of the 3D scope 206 are known. The optical features of the HMD 208 are the positional relation between the eye 212a and the display section 208a and the positional relation between the eye 212b and the display section 208b. The optical features of the 3D scope 206 are the positional relation between the objective optical system 209a and the CCD 210a, the positional relation between the objective optical system 209b and the CCD 210b, and the magnifications of the optical systems 209a and 209b.

It is desirable that the eye 212a and the display section 208a have a positional relation similar to the positional relation between the objective optical system 209a and the CCD 210a, and that the eye 212b and the display section 208b have a positional relation similar to the positional relation between the objective optical system 209b and the CCD 210b. Is so, then: $\theta L = \phi L$ and $\theta R = \phi R$, where $\theta L$ and $\phi R$ are angles at which the optical axes of the eyes 212a and 212b incline to the optical axes of the object optical systems 209a and 209b when both optical systems 209a and 209b have their focal points at the object 232, $\theta L$ is an angle between the axis A of the cornea 221a of the left eye 212a and the optical axis of the display section 208a, and $\theta R$ is an angle between the axis A of the cornea 221a of the left eye 212b and the optical axis of the display section 208b.

The operation of the controller 207 will now be explained with reference to FIG. 33 and FIGS. 34A, 34B and 34C.

Figure 34A:
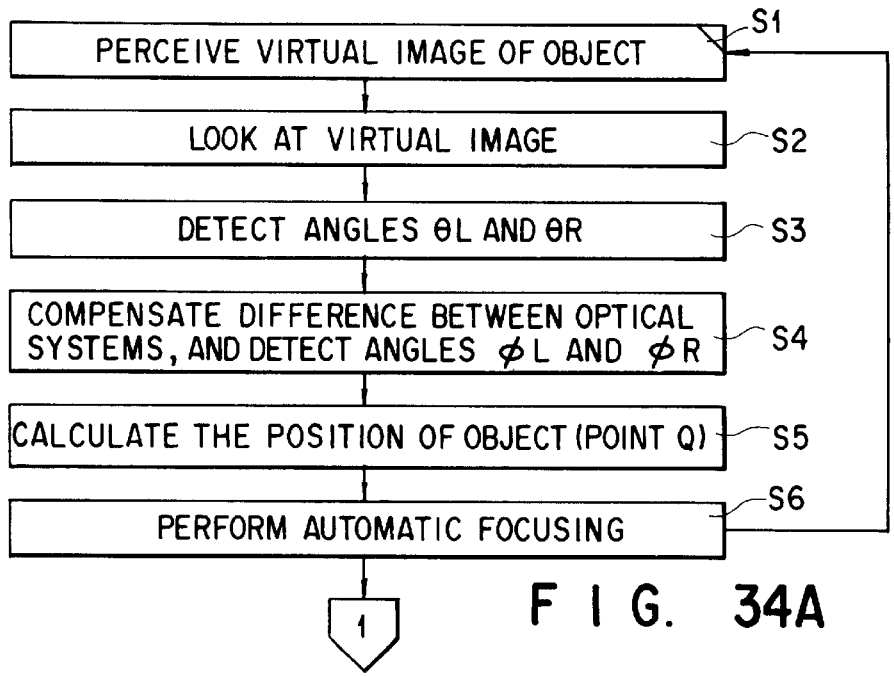
FIGS. 34A, 34B and 34C are flow charts explaining how the controller controls the slave manipulator in the eleventh embodiment.
Figure 34B:
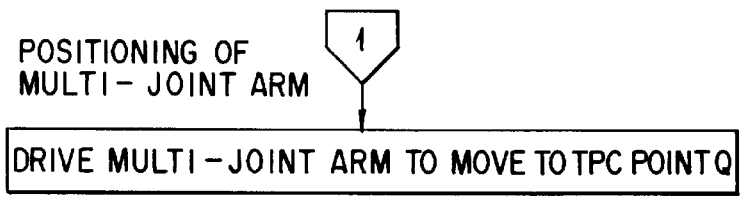
Figure 34C:
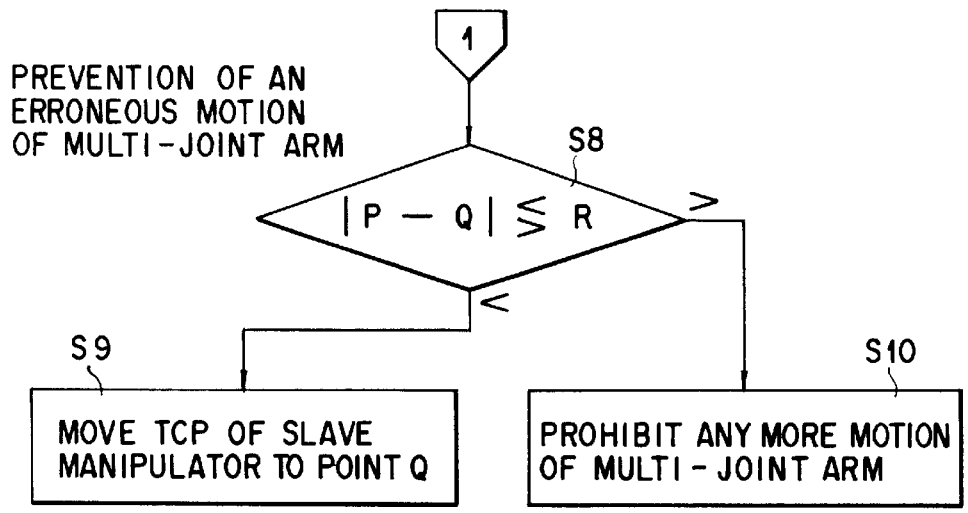

FIG. 34A is a flow chart explaining how the orientations of the optical axes of the surgeon's eyes are detected to determine the position an object assumes in a body cavity, and how the automatic focusing is performed in the 3D scope 206 in accordance with the position of the object. FIG. 34B is a flow chart showing how the slave manipulator 201 is operated and moved toward the position of the object which has been determined from the orientations of the optical axes of the eyes. FIG. 34C is a flow chart explaining how the position of the object, determined from the orientations of the optical axes of the eyes, is applied to prevent the slave manipulator 201 from being remote-controlled erroneously. In the remote-control method of FIG. 34C which differs from the method of FIG. 34B, the slave manipulator 201 can be remote-controlled as the surgeon 210 operates the master arm 209 if the TCP of the slave manipulator 201 is present within a predetermined radius from the point which corresponds to the TCP of the master arm 209.

Figure 33:
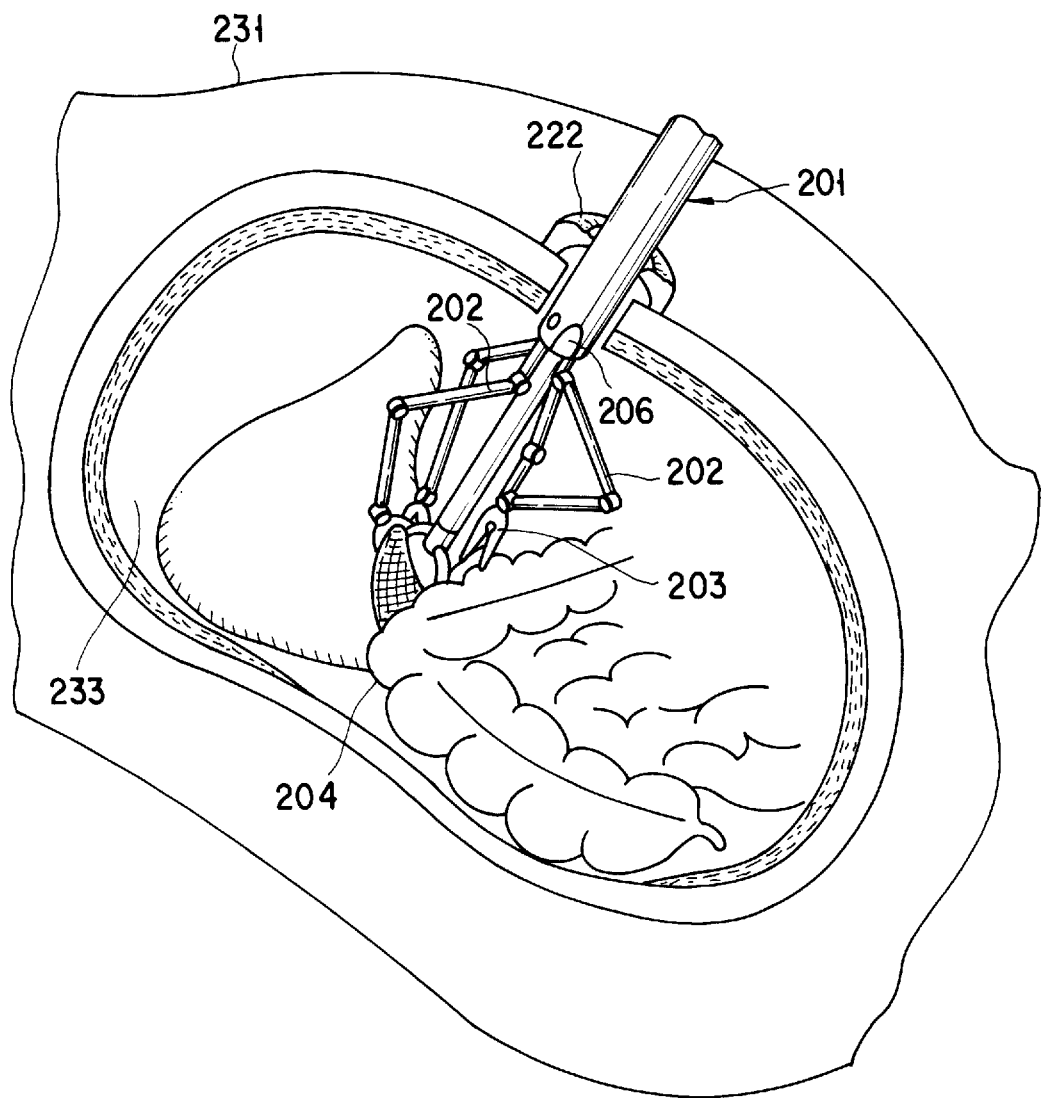
FIG. 33 is a diagram for explaining how the slave manipulator incorporated in the eleventh embodiment is operated to perform a transcutaneous endoscope surgery.

FIG. 33 is a diagram illustrating how the surgeon 210 remote-controls the slave manipulator 201, thereby performing a transcutaneous endoscope surgery on a patient 231. As shown in FIG. 33, the distal end portion of the slave manipulator 201 is inserted into the body cavity 233, guided through a trocar 222 fitted in an opening incised in the abdominal wall of the patient 231. The 3D scope 206 provided in the distal end of the slave manipulator 201 scans the interior of the body cavity 233 and generates a left-eye image signal and a right-eye image signal. The two image signals are supplied to the controller 207, which processes the signals into video signals of standard type. The video signals are supplied to the HMD 208, which forms a 3D image. Looking at the 3D image, the surgeon 210 operates the master arm 209. The distal end portion of the slave manipulator 201 is operated in the body cavity 233—in the same way as the master arm 209. Surgery is thereby performed in the body cavity 233.

With reference to the flow chart of FIG. 34A, it will be explained how the orientations of the optical axes of the surgeon's eyes are detected to determine the position an object assumes in a body cavity, and how the automatic focusing is performed in the 3D scope 206 in accordance with the position of the object.

First, in Step S1, the surgeon 210 recognizes a virtual image 232' displayed by the HMD 208. Then, he or she looks at the virtual image 232' in Step S2. In Step S3, the sensors 213a and 213b incorporated in the HMD 208 detect the angles θL and θR, both defined and described above, thus detecting the orientations of the optical axes of the surgeon's eyes 212a and 212b, respectively. From the orientations of the optical axes of the eyes, the position calculating circuit 215 calculates the position of the position of the object. More precisely, in Step S4, the circuit 215 compensates for the geometrical difference between the optical system of the 3D scope 206 and that of the HMD 208, in accordance with the angles θL and θR, both defined and described above. The angles φL and φR, at which the optical axes of the eyes 212a and 212b incline to the optical axes of the object optical systems 209a and 209b, are thereby obtained in Step S4. Based on the φL and φR, the position of the object is determined in Step S5 by the same method as employed in trigonometrical survey. Then, in Step S6, the position calculating circuit 215 controls the 3D scope 206 such that automatic focusing is accomplished in the 3D scope 206.

For simplicity of explanation, how to detect the position of the object has been described, with reference to FIGS. 29A and 29B and FIGS. 34A which show and describe as if the optical axes of the surgeon's eyes, the axes of the optical units incorporated in the 3D scope 208 and the HMD 208 were present in a plane, not in a space. Nonetheless, it may be understood from the above that the position the object assumes in a space can be detected in the eleventh embodiment.

With reference to the flow chart of FIG. 34B, a method of remote-controlling the slave manipulator 201 will be explained. When controlled by the controller 207, the drive section 205 drives the multi-joint arm 202, whereby the TCP of the gripper 203 is moved to a point Q which is the position of the object determined by the position calculating circuit 215.

With reference to the flow chart of FIG. 34C, another method which the controller 207 effects to remote-control the slave manipulator 201 will be explained.

In this method shown in FIG. 34C, it is determined in Step S8 whether or not $|P-Q|<R$, where P is the position of the TCP of the master arm 209 (FIG. 31A), Q is that position of the object which has been determined from the orientations of the optical axes of the surgeon's eyes, and R is a radius within which the TCP of the gripper 203 can be moved without damaging the object or the multi-joint arm 202, or both. In the case shown in FIG. 31B, the point Q coincides with the TCP of the gripper 203.

The control circuit 217 can remote-control the drive circuit 205 of the slave manipulator 201 only while the surgeon 210 looks at a point which exists within a radius of R from the TCP of the multi-joint arm 202. Stated in another way, the multi-joint arm 202 can be driven by the control circuit to have its TCP move toward the point Q corresponding to the point P (i.e., the TCP of the master arm 209), provided that $|P-Q|<R$.

Assume that the TCP of the slave manipulator 201 is located at the point Q which corresponds to the point P where the TCP of the master arm 209 is located. When the surgeon 210 shifts his or her eyes to a point Q1 shown in FIG. 31B, it is determined in Step S8 that $|P-Q|<R$. That is, YES in Step S8. The flow goes to Step S9, in which the control circuit 217 can further control the drive section 205. When the surgeon 210 operates the master arm 209, moving the TCP of the arm 209 to the point P, the control circuit 217 controls the drive section 205, which drives the multi-joint arm 202. The TCP of the slave manipulator 201 is thereby moved to the point Q which corresponds to the point P. On the other hand, when the surgeon 210 shifts the eyes to a point Q2 shown in FIG. 31B, it is determined in Step S8 that $|P-Q|>R$. Namely, NO in Step S8. The flow goes to Step S10, in which the multi-joint arm 202 can no longer be driven.

Thus, in the eleventh embodiment, unless the surgeon 210 looks at a point present within a radius of R from the TCP of the slave manipulator 201, the slave manipulator 201 cannot be operated even if an operation command is issued from the master arm 209. Neither the object nor the multi-joint arm 202 is damaged. This helps increase the safety of transcutaneous endoscope surgery.

When tired, the surgeon 210 can hardly keep his or her attention to the object. His or her attention may leave the object, though momentarily, and his or her eyes shift from the virtual image of the object. If this happens, the slave manipulator 201 can no longer be operated, and the object and the multi-joint arm can therefore be protected from damage. In view of this, the eleventh embodiment is advantageous.

The twelfth embodiment of the present invention will now be described, with reference to FIG. 35 and FIGS. 36A, 36B and 36C. The components of this embodiment which are identical to those of the eleventh embodiment, are designated by the same reference numerals in FIGS. 35–36C, and will now be described in detail.

Figure 35:
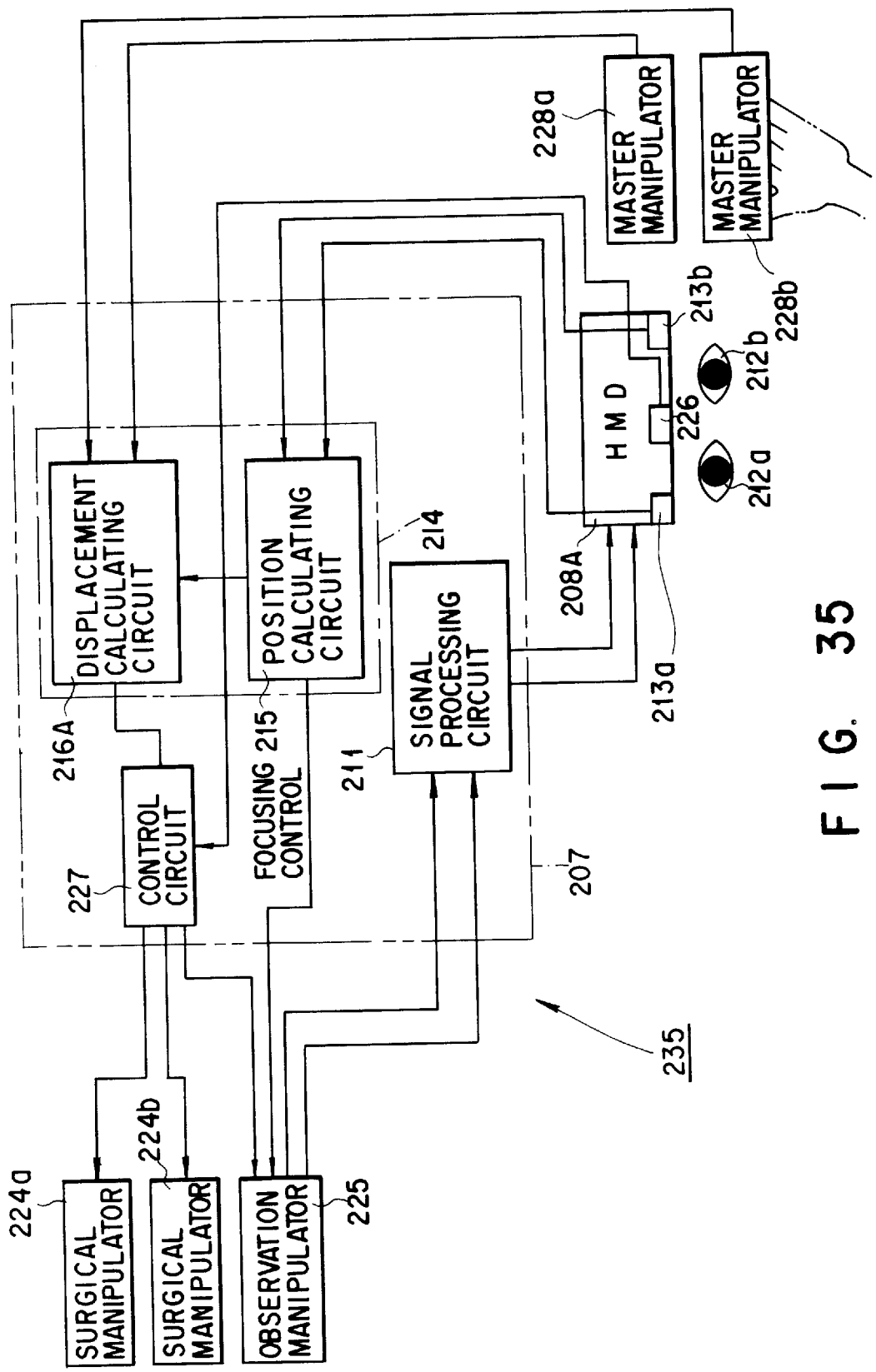
FIG. 35 is a block diagram illustrating the surgical manipulator system according to the twelfth embodiment of this invention.

As shown in FIG. 35, the twelfth embodiment, or a surgical manipulator system 235, comprises a controller 207, a HMD 208A, two surgical manipulators 224a and 224b, an observation manipulator 225, and two master manipulators 228a and 228b. The controller 207 remote-controls the surgical manipulators 224a and 224b in accordance with the operation of the master manipulators 228a and 228b. The controller 207 controls the observation manipulator 225, as well, in accordance with the motion of the HMD 208A.

As shown in FIG. 36A, the distal end portions of the surgical manipulators 224a and 224b, and the distal end portion of the inserted on manipulator 225 are inserted into a body cavity, so that surgery may be performed on an object which exists in the body cavity. A 3D scope 225a is provided in the distal end of the observation manipulator 225.

As shown in FIG. 35, the controller 207 comprises a signal processing circuit 211, an arithmetic processing unit 214 and a control circuit 227. The arithmetic processing unit 214 comprises a position calculating circuit 215 and a displacement calculating circuit 216A.

The HMD 208A is identical to the HMD 208 shown in FIG. 28, except that it has an additional component, i.e., a position sensor 226 for acquiring information on six degrees of freedom which pertain to the position and inclination of the HMD 208A. The position sensor 226 comprises a sense coil 226a and a source coil 226b. As shown in FIG. 36B, the sense coil 226a is wound around three axes which extend at right angles to one another. The source coil 226b is fixed steadfastly. The sense coil 226a detects the intensity of the magnetic field emanating from the source coil 226b, thereby acquiring the information on the six degrees of freedom pertaining to the position and inclination of the HMD 208A. The displacement of the HMD 208A, detected by the position sensor 226, is supplied to the control circuit 227 incorporated in the controller 227. The control circuit 227 changes the orientation of the 3D scope 225 in accordance with the displacement which the position sensor 227 has detected.

The master manipulators 228a and 228b are connected to the displacement calculating circuit 216A of the controller 207. The control circuit 227 controls the surgical manipulator 224a in accordance with the displacement of the manipulator 224a, which the circuit 216A has calculated from the position designated by the master manipulator 228a, and the position of the object, which the circuit 216 has calculated. Similarly, the control circuit 227 controls the surgical manipulator 224b in accordance with the displacement of the manipulator 224b, which the circuit 216A has calculated from the position designated by the master manipulator 228b, and the position of the object, which the circuit 216 has calculated.

While wearing the HMD 208A and looking at the virtual image of the object displayed by the HMD 208A, a surgeon 210 operates the master manipulators 228a and 228b, whereby the controller 207 remote-controls the surgical manipulators 224a and 224b. To be more specific, the control circuit 227 receives the information which the sense coil 226a has acquired by detecting the intensity of the magnetic field emanating from the source coil 226b and which represents the six degrees of freedom pertaining to the position and inclination of the HMD 208A. From this information the control circuit 227 determines the TCP of the observation manipulator 225. Further, the control circuit 227 controls the surgical manipulators 224a and 224b as the surgeon 210 operates the master manipulators 228a and 228b, provided that the position of the object, which has been obtained from the orientations of the optical axes of the surgeon's eyes 212a and 212b by the sensors 213a and 213b of the HMD 208A by the same method used in the eleventh embodiment, is within a predetermined distance from the TCPs of the surgical manipulators 224a and 224b.

With the twelfth embodiment it is possible for the surgeon 210 to remote-control both surgical manipulators 224a and 224b, while looking at the 3D virtual image of the object located in a body cavity and maintaining the observation manipulator 225 at a desired position in the body cavity. The surgeon 210 therefore has a good sense of immediacy. Like the eleventh embodiment, the twelfth embodiment enables the surgeon 210 to perform a transcutaneous endoscope surgery in high safety.

As described above, in the eleventh and twelfth embodiments of the invention, any surgical manipulator is not operated when the surgeon's eyes shift too far from the virtual image of the object, even if an operation command is issued from a master manipulator. No excessive force is therefore exerted on the object or any surgical manipulator even if the surgeon unintentionally operates a master manipulator in an erroneous way. In view of this, both the eleventh embodiment and the twelfth embodiment enable the surgeon 210 to perform a transcutaneous endoscope surgery in safety.

The thirteenth embodiment of the invention will be described with reference to FIGS. 37A and 37B and FIG. 38.

As shown in FIG. 38, the thirteenth embodiment comprises an endoscope 301 and a surgical manipulator 302. The endoscope 301 has an insertion section 304 which can be inserted into the abdominal cavity. The surgical manipulator 302 has an insertion section 308 which can be inserted into the cavity 307. In the instance shown in FIG. 38, the insertion section 304 of the endoscope 301 is inserted into the stomach 303 through the mouth and the food passage, and the insertion section 308 of the surgical manipulator 302 is inserted into the stomach 303 through a trocar 306 set in an opening incised in, for example, the abdominal wall 305.

A bending tube 309 is connected to the distal end of the insertion section 304 of the endoscope 301, and a distal-end unit 310 is attached to the bending tube 309. An operation section 311 is connected to the proximal end of the endoscope 301. The operation section 311 contains an actuator (not shown) for driving the ending tube 309 and the distal-end unit 310 under the control of a controller (not shown).

Figure 37A:
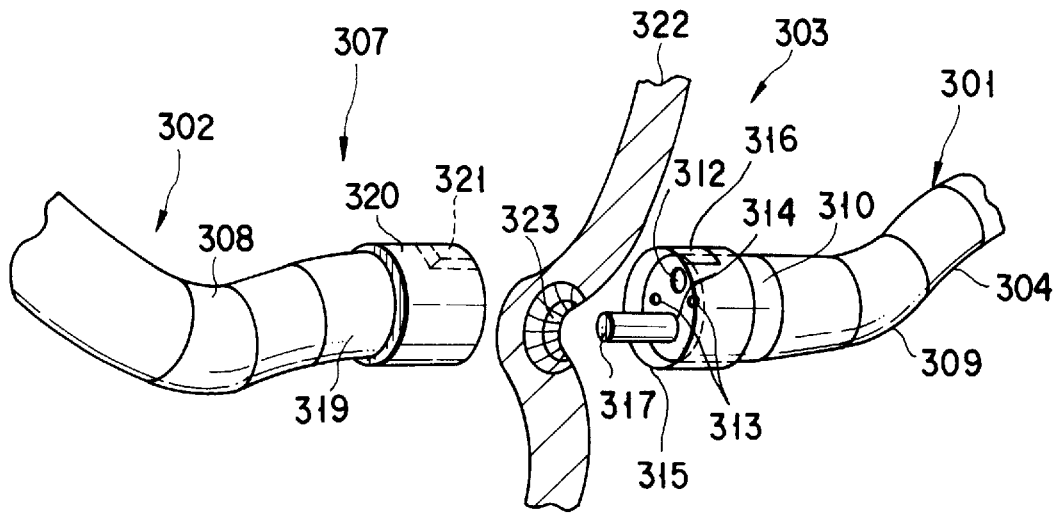
FIGS. 37A and 37B are perspective views of the endoscope and the surgical manipulator, both incorporated in the thirteenth embodiment of the present invention.
Figure 37B:
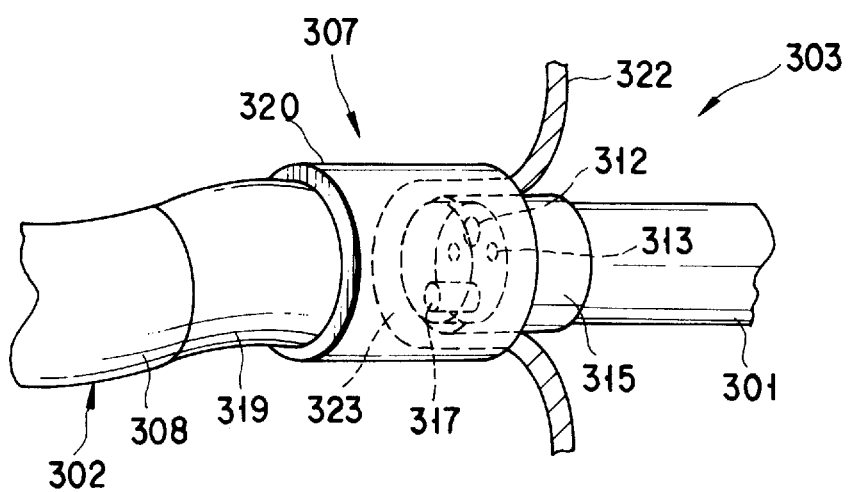

As shown in FIG. 37A, the distal-end unit 310 has an observation window 312, an illumination window 313 and an instrument channel 314. A hollow cylindrical hood 315 is mounted on the circumferential surface of the distal-end unit 310. A permanent magnet 316 is fastened to the inner circumferential surface of the hood 315. A laser probe 317 extends through the instrument channel 314, with its distal end portion protruding outward from the distal-end unit 310. Instead of the laser probe 317, an instrument such as a cautery knife, a forceps or a medicine-applying tube may be inserted through the instrument channel 314. The insertion section 304 of the endoscope 301 may be inserted into the stomach 303 by using a manipulator.

The surgical manipulator 302 comprises a manipulator body 308 and a hollow cylindrical cap 320. The manipulator body 308 has joints 308a and connected at its proximal end to a base 318 which is secured to the floor. The cap 320 is fastened to the distal end of the manipulator body 308. The cap 320 has an inner diameter slightly larger than the outer diameter of the hood 315 of the endoscope 301, and can therefore be slidably mounted on the outer circumferential surface of the hood 315.

Attached to the cap 320 is a Hall element 321 for detecting the magnetic field emanating from the permanent magnet 316. The Hall element 321 can therefore detect the position of the distal-end unit 310 of the endoscope 301, the unit 310 and the distal end portion 319 of the manipulator 302, both inserted in the abdominal cavity 307, and which are partitioned by the stomach wall 322 and cannot be seen from outside. The permanent magnet 316 and the Hall element 321 constitute a unit for detecting the position of the distal-end unit 310.

The surgical manipulator 302 further comprises an actuator (not shown) for driving the manipulator body 318. The actuator is controlled by a controller (not shown).

As described above, the cap 320 is slidably mounted on the outer circumferential surface of the hood 315. The hood 315 and the cap 320 can therefore be moved toward each other, to clamp the stomach wall 322. In other words, the hood 315 and the cap 320 constitute a unit for clamping the stomach wall 322. This unit can clamp a diseased part 323 (e.g., a malignant tumor) of the stomach wall 322 or a portion of the wall 322 ambient to the diseased part 323. While clamped between the hood 315 and the cap 320 and held firmly, the diseased part 323 can be irradiated with a laser beam emitted from the laser probe 317 inserted in the instrument channel 314 of the endoscope 301. Alternatively, while the diseased part 323 is held firmly, a cautery knife may be manipulated to incise the diseased part 323, a forceps may be used to extract a tissue from the part 323, or a medicine-applying tube may be directed to the part 232 to apply a medicine thereto.

The fourteenth embodiment of this invention, which is a surgical manipulator system, will be described with reference to FIGS. 39, 40A, 40B and 41.

FIG. 39 is a perspective view showing the aorta 330, explaining how the surgical manipulator system is operated to implant an artificial blood vessel 333 in the dissecting part 332 of the aorta 330, thereby to remedy dissecting aneurysm.

As shown in FIG. 39, the surgical manipulator system comprises, among other things, an endoscope 334, two other endoscopes 343, and two two-arm micro-manipulators 344.

The endoscope 334 has an insertion section 336, a bending section 337, a distal-end unit 338 and a balloon 342. The insertion section 336 is inserted into the aorta 330, passing through an incised part 335 of one of the two femoral arteries 331 which are continuous to the aorta 330. The bending section 337 is connected to the distal end of the insertion section 336. The distal-end unit 338 is attached to the distal end of the bending section 337. The unit 338 has an observation window 339, an illumination window 340, an instrument channel 341, and a permanent magnet (not shown). The balloon 342 is mounted on the distal-end unit 338 as illustrated in FIGS. 40A and 40B.

The insertion section 336 of the endoscope 334 is inserted in the artificial blood vessel 333. The balloon 342 is inflated, pressing the distal end portion of the blood vessel 333 from within. The artificial blood vessel 333 is thereby held steadfastly. The artificial blood vessel 333 consists of two rigid end portions 333a and a soft intermediate portion 333b. The end portions 333a are made of bioceramics such as hydroxy apatite, β-TCP or the like. The intermediate portion 333b is made of Goatex, Duclon or the like. Either end portion 333a has an annular groove 333c in its outer circumferential surface, as is best shown in FIG. 41.

The endoscopes 343 are inserted via trocars (not shown) into the body cavity in which the aorta 330 and the femoral arteries 331 are located. Similarly, the two-arm micro-manipulators 344 are inserted into the body cavity through trocars (not shown). The endoscopes 343 are essentially identical in structure to the endoscope inserted in the aorta 330. They have a Hall element (not shown) each in the distal-end unit 338. Each two-arm micro-manipulator 344 comprises two arms and two holders 345 connected to the distal ends of the arms, respectively. The holders 345 have a visual sensor (not shown) each.

It will be explained how a surgeon operates the fourteenth embodiment in order to implant the artificial blood vessel 333 in the aorta 330.

First, the surgeon mounts the artificial blood vessel 333 on the insertion section 336 of the endoscope 334. The balloon 342 is inflated, pushing the distal end portion 333a of the blood vessel 333 outwards from within. The artificial blood vessel 333 is thereby held steadfastly.

Next, the surgeon inserts the insertion section 336 into the left femoral artery 331 through the incised part 335 of the left femoral artery 331. He or she further inserts the section 336 through the dissecting part 332 of the aorta 330 until the distal-end unit 338 reaches a position a little above the dissecting part 332 of the aorta 330. As a result of this, the artificial blood vessel 333 seals the dissecting part 332.

Further, the surgeon inserts the endoscopes 343 and the two-arm micro-manipulators 344 into the body cavity through the trocars (not shown). The surgeon moves the endoscopes 343 toward the end portions 333a of the artificial blood vessel 333, respectively. While observing the aorta 330 through the endoscopes 343, the surgeon operates the two-arm micro-manipulators 344, wrapping sutures 346 around those portions of the aorta 330 which are mounted on the end portions 333a of the artificial blood vessel 333 and tying the sutures 346. The artificial blood vessel 333 is thereby fixed in the aorta 330.

More precisely, either two-arm micro-manipulator 344 winds a suture 346 around the aorta 330 and ties it, fastening the artificial blood vessel 333 to the dissecting part 332 of the aorta 330. The two-arm micro-manipulator 344 automatically performs this sequence of complicated operations in accordance with a computer program. Either portion of the aorta 330 which has been tied with the suture 346 is fit into the annular 333c formed in the end portion 333a of the artificial blood vessel 333. The blood vessel 333 is prevented from slipping down in the aorta 330.

Once the artificial blood vessel 333 has been implanted in the aorta 330, its outer circumferential surface is covered with the inner surface of the aorta 330. Its end portions 333a, if made of β-TCP, will be gradually absorbed into the inner surface of the aorta 330, and will cease to exist. There will leave in the aorta 330 only the soft intermediate part 333b which is as flexible as the aorta 330.

The implantation of the artificial blood vessel 333 described above, which is performed by using endoscopes, is totally transcutaneous. This surgery is little invasive and ensures fast recovery of the patient.

In the thirteenth and fourteenth embodiments, as indicated above, two medical instruments are located in and outside a body tube, respectively, in order to observe the interior and exterior of the body tube and to achieve treatment on the body tube. The second medical instrument is moved by means of an actuator toward the target part of the body tube. Then, both medical instruments are manipulated, treating the target part of the body tube within a short time.

The fifteenth embodiment of this invention will be described with reference to FIGS. 42, 43, 44A to 44C and 45.

Figure 42:
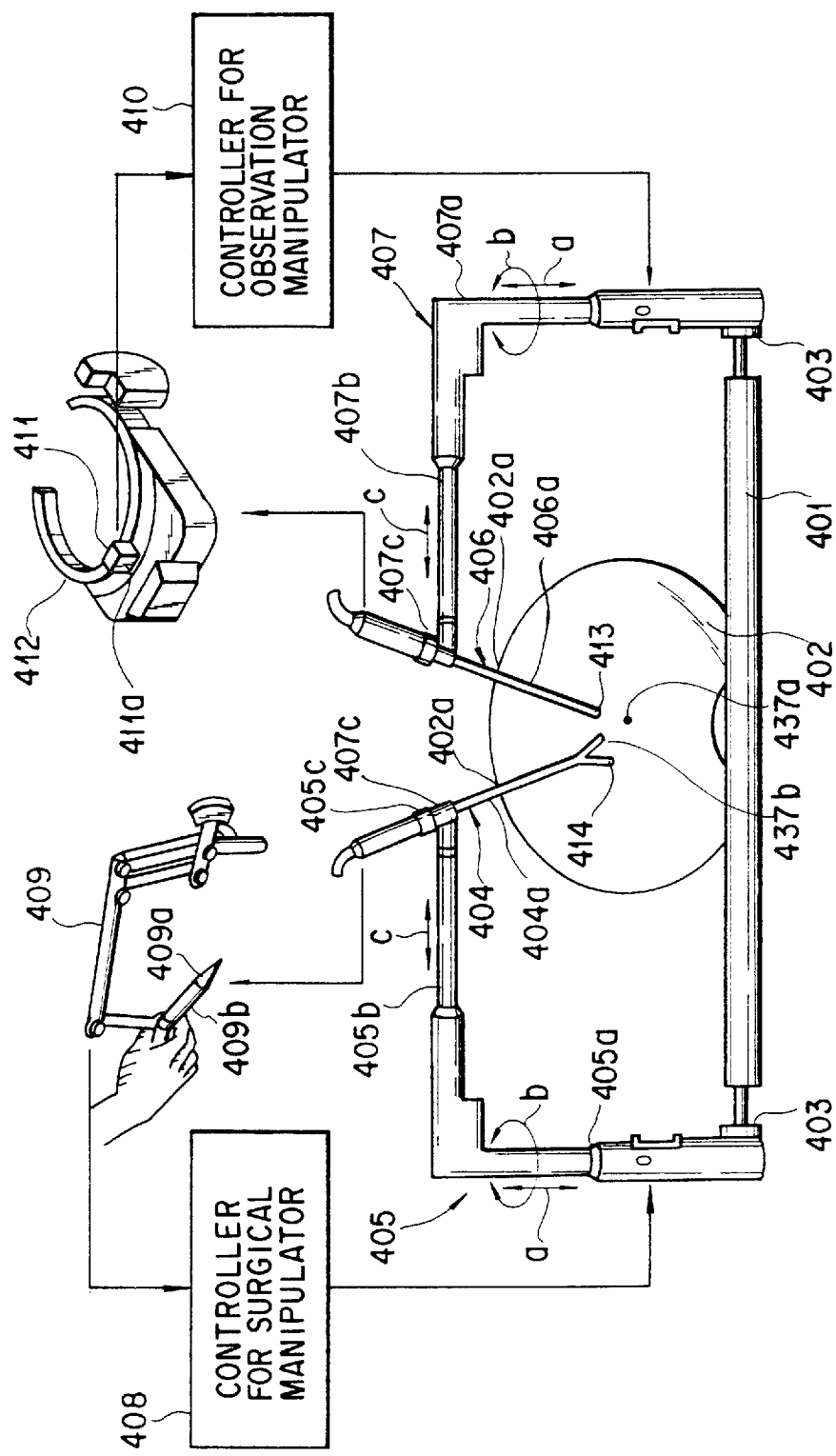
FIG. 42 is a schematic representation of the surgical manipulator system according to the fifteenth embodiment of the invention.

FIG. 42 schematically illustrates the surgical manipulator system according to the fifteenth embodiment. Shown in FIG. 42 are an operating table 401 and the patient 402 lying on the back on the table 401. Parallel bedside rails 403 are laid on the sides of the operating table 401. The surgical manipulator system comprises a first slave manipulator (hereinafter called "surgical manipulator 405"), a second slave manipulator (hereinafter called "observation manipulator 407). The surgical manipulator 405 is slidably mounted on the left bedside rail 403, and the observation manipulator 407 is slidably mounted on the right bedside rail 403.

The surgical manipulator 405 has a first shaft 405a which can rotate and move vertically, a second shaft 405b which is connected to the upper end of the first shaft 405a and can move horizontally, and a coupler 405c secured to the distal end of the second shaft 45b. Similarly, the observation manipulator 407 has a first shaft 407a which can rotate and move vertically, a second shaft 407b which is connected to the upper end of the first shaft 407a and can move horizontally, and a coupler 407c secured to the distal end of the second shaft 407b. The connector 405c holds a medical instrument 404, whereas the connector 407c holds a 3D endoscope 406.

As shown in FIG. 42, the surgical manipulator system further comprises a first controller 408, a second controller 410, a master manipulator (operating means) 409, a HMD 412, and a 3D digitizer 411. The surgical manipulator 405 is connected to the first controller 408, which in turn is connected to the master manipulator 409. The observation manipulator 407 is connected to the second controller 410, which in turn is connected to the digitizer 411. The 3D digitizer 411, which is a position sensor, is mounted on the HMD 412. Alternatively, it may be directly put on a surgeon's head. Furthermore, the digitizer 411 may be replaced by a joystick or a key switch.

The first shaft 405a of the surgical manipulator 405 can be driven vertically and rotated by actuators (not shown) such as electromagnetic motors. The second shaft 405b of the manipulator 405 can be driven horizontally and rotated by actuators (not shown, either) such as electromagnetic motors. Hence, the shafts 405a and 405b and the electromagnetic motors constitute a drive mechanism for driving a so-called cylindrical coordinate type manipulator which has a vertical axis $\underline{a}$, a rotation axis $\underline{b}$ and a horizontal axis $\underline{c}$. Similarly, the second shaft 407a of the observation manipulator 407 can be driven vertically and rotated by actuators (not shown) such as electromagnetic motors. The second shaft 407b of the manipulator 407 can be driven horizontally and rotated by actuators (not shown, either) such as electromagnetic motors. Hence, the shafts 407a and 407b and the electromagnetic motors constitute a drive mechanism for driving a so-called cylindrical coordinate type manipulator which has a vertical axis $\underline{a}$, a rotation axis $\underline{b}$ and a horizontal axis $\underline{c}$. These drive mechanisms may be replaced by multi-joint manipulators.

The 3D endoscope 406 has an insertion section 406a. A CCD camera 413 is attached to the distal end of the insertion section 406a. An image provided by the CCD camera 413 is displayed by the HMD 412. Instead, the image may be displayed by means of a TV monitor. Further, the CCD camera 413 may be replaced by a unit comprised of a camera secured to the proximal end of the insertion section 406a and an optical image-transmitting device a relay lens, or may be replaced by a stereoscopic unit comprised of two cameras secured to the proximal end of the insertion section 406a and two optical image-transmitting devices such as relay lenses.

The medical instrument 404 has an insertion section 404a. Attached to the distal end of the insertion section 404a is a forceps 414 for holding a tissue or an organ. Instead of the forceps 414, a tool such as a knife, a suture applicator or the like, may be attached the distal end of the insertion section 404a. Connected to the proximal end of the insertion section 404a is an actuator (not shown) for opening and closing the forceps 414.

The couplers 405c and 407c are identical in structure. Only the coupler 407c of the observation manipulator 407 will be described with reference to FIG. 43.

Figure 43:
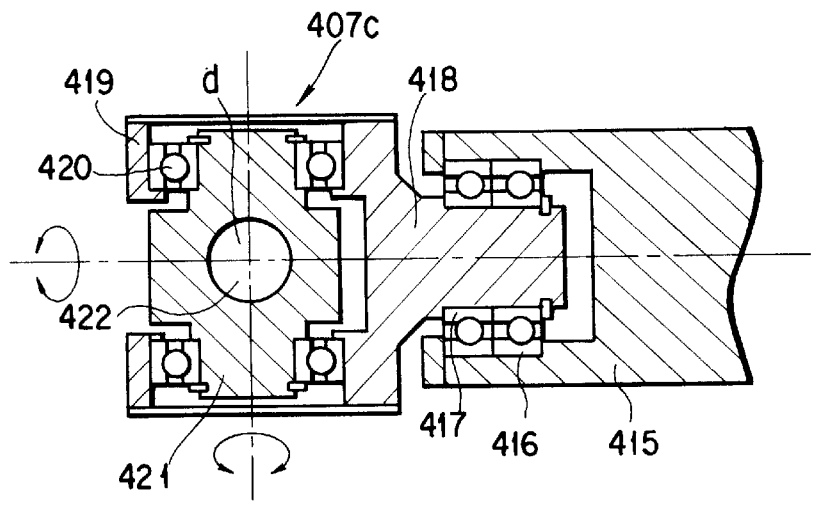
FIG. 43 is a sectional view of the coupler used in the fifteenth embodiment, said view taken along a horizontal plane.

As shown in FIG. 43, the distal end portion 415 of the second shaft 407b of the manipulator 407 has an axial hole 416. In this hole 416, a shaft 418 on a bearing 417 is rotatably supported. Formed integral with the shaft 418 is a forked bearing holder 419. The holder 419 has a bearing 420 having an axis which crosses the axis of the bearing 417 at right angles. The bearing holder 419 supports a joint shaft 421, allowing the shaft 421 to rotate freely. Thus, the joint shaft 421 can rotate with two degrees of freedom at point d where it intersects with the axis of the insertion section 406a of the 3D endoscope 406. The joint shaft 421 has an axial hole 422, in which the insertion section 406a is fitted and secured by a nut (not shown).

The operation of the surgical manipulator system according to the fourteenth embodiment will now be explained, with reference to FIGS. 44A to 44C and the flow chart of FIG. 45.

Figures 44A, 44B:
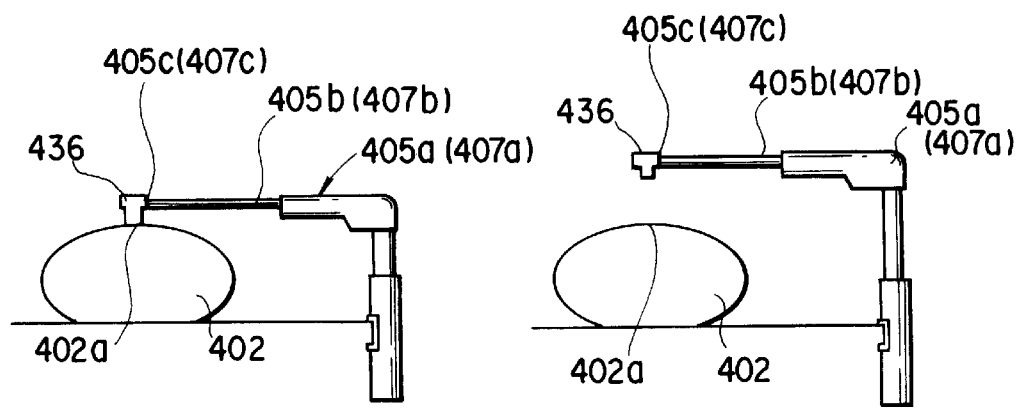
FIGS. 44A, 44B and 44C are diagrams for explaining the operation of the fifteenth embodiment.
Figure 44C:
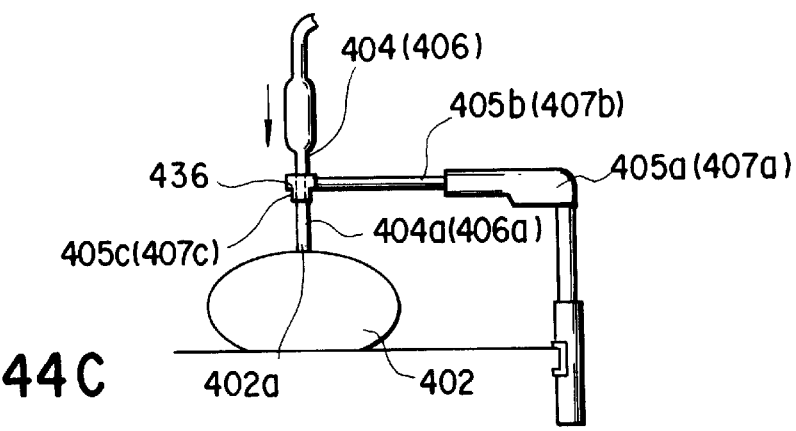

As can be understood from FIGS. 44A to 44C, the position of the lower end 436 of the coupler 405c of the surgical manipulator 405 is known from the positions of TCPs on the axes a, b and c and the sizes of the second shaft 405b. The same is true of the observation manipulator 407.

First, the coupler 405c is moved, setting its lower end 436 into alignment with an opening 402a incised in the body wall, in Step S1' (FIG. 45), as shown in FIG. 44A. Then, in Step S2' (FIG. 45), the data representing the position of the lower end 436, thus aligned with the opening 402a, is stored as data showing the position of the opening 402a, in a memory incorporated in the controller 408.

Next, in Step S3', the surgical manipulator 405 is operated, moving the coupler 405c upwards, away from the opening 402a, as illustrated in FIG. 44B. In Step S4', the medical instrument 404 is attached to the coupler 405c, and the insertion section 404a of the instrument 404 is inserted into a body cavity, first through the axial hole 422 of the joint shaft 421 and then through the opening 402a—as illustrated in FIG. 44C. Then, the insertion section 404a is held in the axial hole 422 by means of a nut (not shown).

Although not shown in FIGS. 44A to 44C, the 3D endoscope 406 is attached to the coupler 407c in the same way as the medical instrument 404, and the insertion section 406a of the 3D endoscope 406 is inserted into the body cavity in the same way as the insertion section 404a of the instrument 404.

In Step S5' (FIG. 45), the position of a TCP 437a, such as the focal point of an objective lens located at the distal end of the insertion section 406a of the endoscope 406, is determined from the positions of the shafts 407a and 407b, the position and size of the opening 402a and the distance between the TCP 437a and the opening 402a. In Step S5', too, the position of an TCP 437B, such as the forceps 414 attached to the distal end of the insertion section 404a of the medical instrument 404, can be determined from the positions of the shafts 405a and 405b, the position and size of the opening 402a and the distance between the TCP 437b and the opening 402a.

The position of the TCP 409a of the master manipulator 409, for example, the center 411a of the digitizer 411 or the distal end 409b of the master manipulator 409 is calculated by the controller 408. In Step S6' (FIG. 45), the surgeon operates the master manipulator 409 such that the TCP 437a of the insertion section 404a and the TCP 437b of the insertion section 407b move to the TCP 409a of the master manipulator 409.

Since the insertion section 404a is connected to the shaft 405b by the coupler 405c having two degrees of freedom, and the insertion section 406a is connected to the shaft 407b by the coupler 407c having two degrees of freedom, neither the medical instrument 404 nor the 3D endoscope 406 exerts any excessive force at the opening 402a even if the patient moves.

In the conventional surgical manipulator system, each manipulator needs to have at least five degrees of freedom to move its TCP to a desired point in a body cavity. In the fifteenth embodiment, each manipulator needs only three degrees of freedom to accomplish the same thing. The fifteenth embodiment can be simple in structure. Furthermore, since both manipulators used are hollow cylindrical ones having a cylindrical coordinate system, the second shafts 405b and 407b of the manipulators protrude horizontally from the sides of the operating table 1, but for only a short distance. In addition, since neither first shaft 405a of the surgical manipulator 405 nor the first shaft 407a of the observation manipulator 407 inclines sideways, there is no obstacle to the surgeon or the nurses assisting the surgeon.

The sixteenth embodiment of the present invention will be described with reference to FIG. 46.

Figure 46:
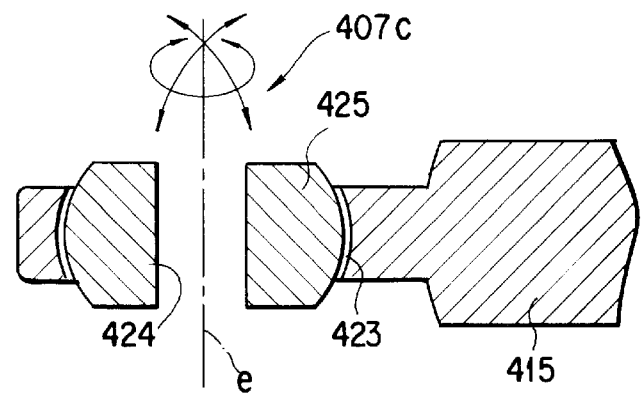
FIG. 46 is a sectional front view of one of the couplers incorporated in the surgical manipulator system according to the sixteenth embodiment of the invention.

FIG. 46 shows a modification of the couplers 405c and 407c. The modified coupler comprises a bearing 423 and a movable member 425. The bearing 423 has a hole whose inner surface is concave. The member 425 is fitted in the hole of the bearing 423 and has three degrees of freedom, capable of rotating around point e. The movable member 425 has a hole 424. As in the fifteenth embodiment, the insertion section 404a of a medical instrument 404 or the insertion section 406a of a 3D endoscope 406 is guided through the hole 424 and held firmly at the hole 424 by means of a nut (not shown).

The seventeenth embodiment of this invention will be described with reference to FIG. 47.

Figure 47:
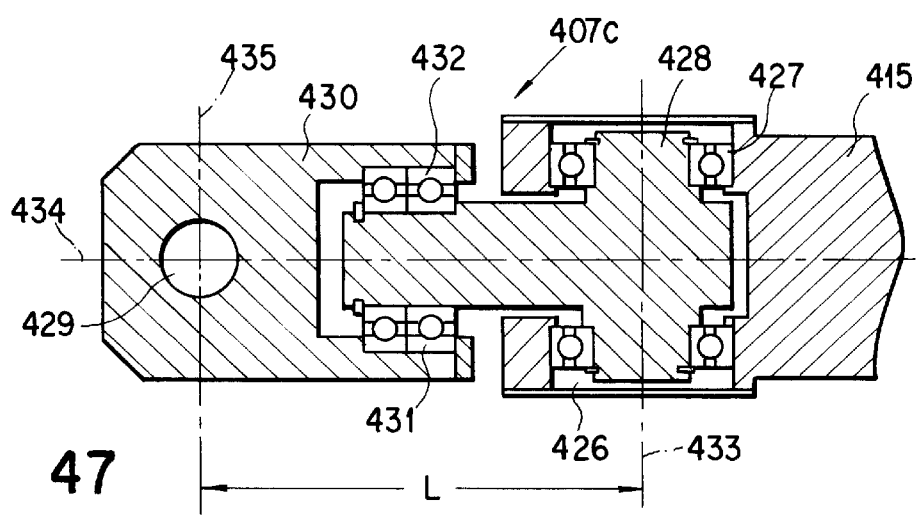
FIG. 47 is a sectional plan view of one of the couplers incorporated in the surgical manipulator system according to the seventeenth embodiment of the invention.

FIG. 47 shows a modification of the couplers 405c and 407c. As shown in FIG. 47, the distal end portion 415 of a shaft has a hole 426 extending at right angles to the axis of the shaft. A bearing 427 is provided on the inner surface of the hole 426. A shaft 428 is rotatably supported by the bearing 427. A holder 430 has two holes 431 and 429 which extend at right angles to each other. A bearing 432 is mounted on the inner surface of the hole 431. A shaft made integral with the shaft 428 and extending at right angles thereto is inserted in the hole 431 of the holder 430 and supported by the bearing 432. The axis 433 of the shaft 428 intersects with the axis 434 of the holder 430 at right angles, but does not intersect with the axis 435 of the insertion section of a medical instrument or a 3D endoscope.

As in the fifteenth embodiment, the insertion section of the medical instrument or the 3D endoscope is guided through the hole 429 and held firmly at the hole 429 by means of a nut (not shown).

Since the distance L between the axes 433 and 435 is long, the distal end of the insertion section of the medical instrument or the 3D endoscope and the distal end of the shaft of the surgical or observation manipulator hardly interfere with each other. As a result, the TCP of the shaft 428 can move in a large space, and ultimately the TCP of the insertion section of the medical instrument or the 3D endoscope can move in a large space. As the surgeon turns his or her head, while looking at the 3DS image of the interior of a body cavity, displayed by the HMD he or she wears, the distal end of the 3D endoscope is moved. While performing a transcutaneous endoscope surgery, the surgeon has such sense of immediacy that he feels as if he or she were in the body cavity.

Figure 48:
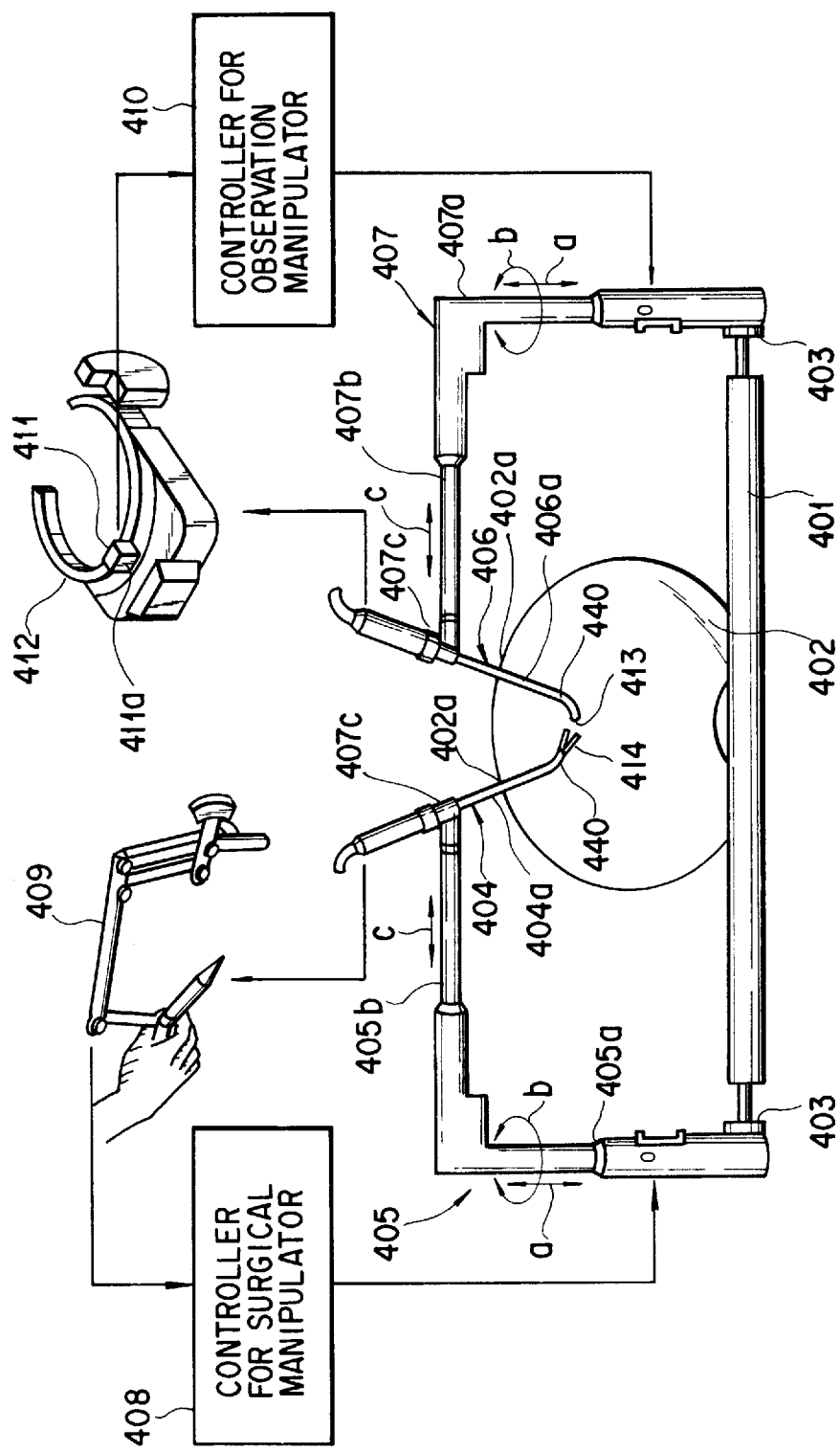
FIG. 48 is a diagram schematically illustrating the surgical manipulator system according to the eighteenth embodiment of the invention.

The eighteenth embodiment of the invention will be described with reference to FIG. 48 and FIGS. 49A and 49B.

The eighteenth embodiment is a surgical manipulator system enables a surgeon to observe an object in a body cavity and treat the object, without exerting an excessive force at the openings incised in the body wall, through which an observation manipulator and a surgical manipulator are inserted into the body cavity. Any component similar or identical to that the fifteenth embodiment is designated by the same reference numeral and will not described in detail.

Figure 49A:
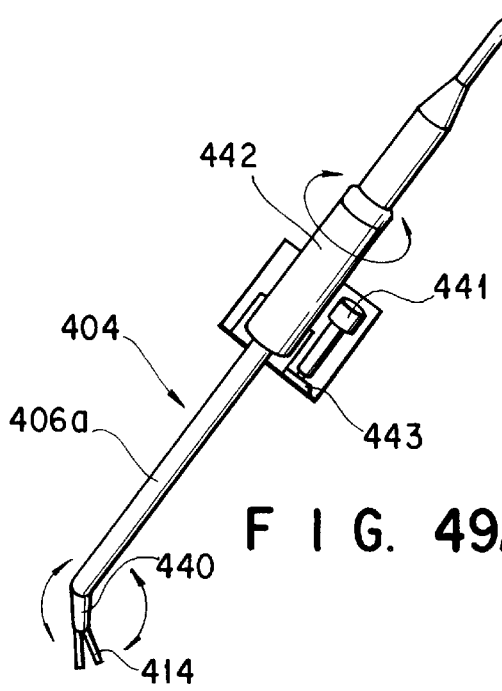
FIGS. 49A and 49B are diagrams explaining the operation of the eighteenth embodiment.
Figure 49B:
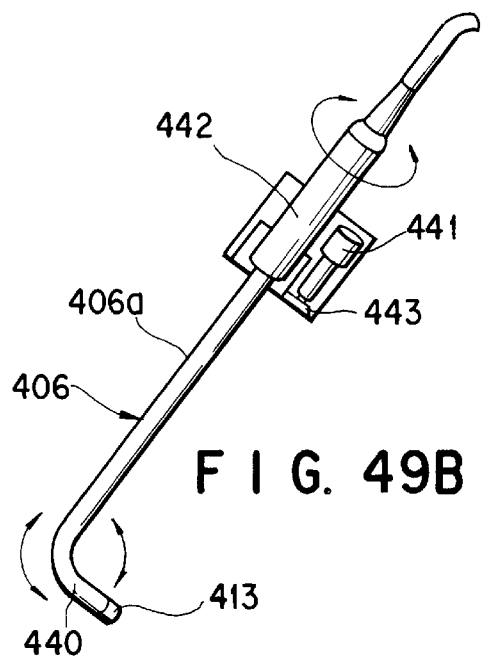

As shown in FIG. 49A, a bending section 440 is connected to the distal end of the insertion section 404a of a medical instrument 404. As shown in FIG. 49B, a bending section 440 is connected to the distal end of the insertion section 406a of a 3D endoscope 406. Either bending section 440 has a bending mechanism (not shown). The bending mechanism has two degrees of freedom and can be driven by an actuator 441 contained in the proximal end of the insertion section (404a, 406a). Wires are used to transmit a force from the actuator 441 to the bending mechanism. The insertion sections 404 and 406a have a shaft 442 each. The shaft 442 is rotated around its axis by a force transmitted from the actuator 441 by a transmitting means 443 such as gears, a timing belt or the like.

In the conventional surgical manipulator system, each manipulator needs to have at least eight degrees of freedom to move the TCP of an insertion section to a desired point in a body cavity. In the eighteenth embodiment, each manipulator needs only six degrees of freedom to accomplish the same thing. The eighteenth embodiment can be simple in structure.

Furthermore, since both manipulators used are hollow cylindrical ones, the second shafts 405b and 407b of the manipulators protrude horizontally from the sides of an operating table 401, but for only a short distance. In addition, since neither first shaft 405a of the surgical manipulator 405 nor the first shaft 407a of the observation manipulator 407 inclines sideways, there is no obstacle to the surgeon or the nurses assisting the surgeon.

As described above, in the fifteenth to eighteenth embodiments, as the surgeon operates the master manipulator, the slave manipulators are operated in the same manner, moving the TCPs of the surgical devices to desired points in a body cavity. Moreover, as the surgeon turns his or her head, while looking at the 3D image of the interior of a body cavity, displayed by the HMD he or she wears, the distal end of the 3D endoscope is moved. While performing a transcutaneous endoscope surgery, the surgeon has such sense of immediacy that he or she feels as if he or she were in the body cavity.

The nineteenth embodiment of the present invention will be described with reference to FIGS. 50 to 57, FIGS. 58A and 58B, and FIG. 59. This embodiment is a surgical manipulator system which comprises two manipulators 503 and 504, a surgical section 531 and an observation section 533.

Figure 51:
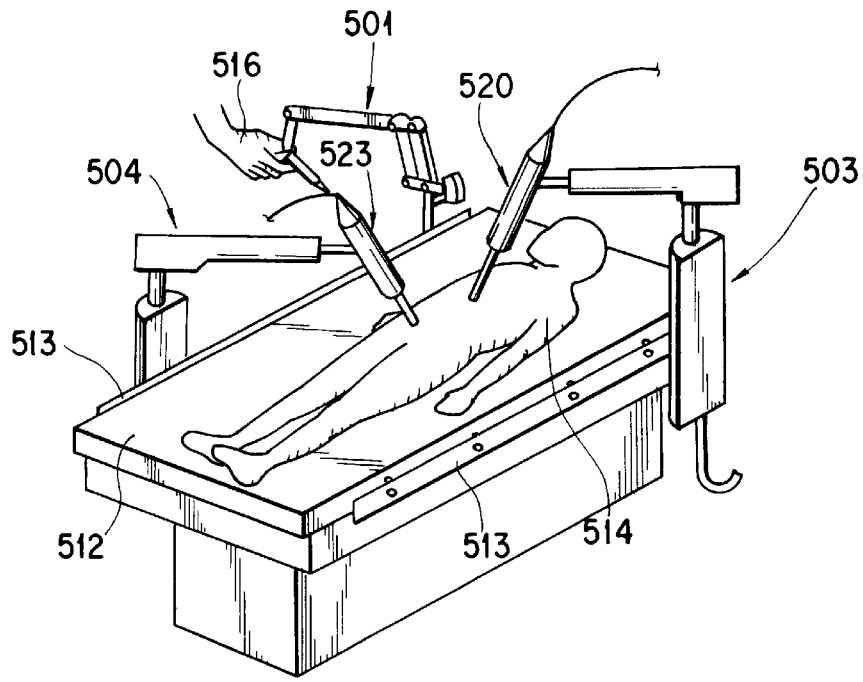
FIG. 51 is a perspective view showing the nineteenth embodiment and explaining the operation thereof.

As shown in FIG. 50, the surgical section 531 comprises a master manipulator 501, a motor control unit 502 and a surgical manipulator 503. The master manipulator 501 is operated by a surgeon 516. The motor control unit 502 remote-controls the surgical manipulator 503 in accordance with information output from the master manipulator 501 and representing the position and orientation of the surgeon's hand. A medical instrument 520 is attached to the distal end of the surgical manipulator 503. The instrument 520 can be bent and has an insertion section 520b. The insertion section 520b is inserted into an abdominal cavity 514 of the patient laying on the back on an operating table 512—through a trocar 530 set in an opening incised in the abdominal wall of the patient. As shown in FIG. 51, the operating table 512 has two parallel bedside rails 513. The master manipulator 501 and the surgical manipulator 503 are removably connected to two supports 515 secured to the bedside rails 513.

The observation section 533 comprises an observation manipulator 504, a manipulator driver 505 and a motor control unit 506. The motor control unit 506 remote-controls the observation manipulator 504 in accordance with control signals supplied from the manipulator driver 505. A 3D scope 523 which can be bent is connected to the distal end of the observation manipulator 504. The 3D scope 523 has an insertion section 523b. The insertion section 523b is inserted into an abdominal cavity 514 of the patient via a trocar 530 set in an opening incised in the abdominal wall of the patient. As shown in FIG. 53, the observation manipulator 504 is removably connected to a supports 515 secured to the bedside rail 513. The manipulator driver 505 may be a joystick, a 3D mouse, a 3D digitizer, a manipulator or the like.

The 3D scope 523 has a pair of imaging elements (not shown) which can generate image signals representing the image of the interior of the abdominal cavity 514. The image signals generated by the imaging elements are supplied via two CCUs 507a and 507b to image processing devices 508a and 508b, respectively. The signal output from the device 508a is supplied to a TV monitor 511, which displays an image of the interior of the body cavity. The signals output from the devices 508a and 508b are supplied to a TV monitor 511 and two displays 510a incorporated in a HMD 510. The displays 510a cooperate to provide a 3D image, which the surgeon 516 who wears the HMD 510 can see. A light source 509 is connected to the observation manipulator 504, whereby light can be supplied into the abdominal cavity 514 through the manipulator 504.

Figure 52:
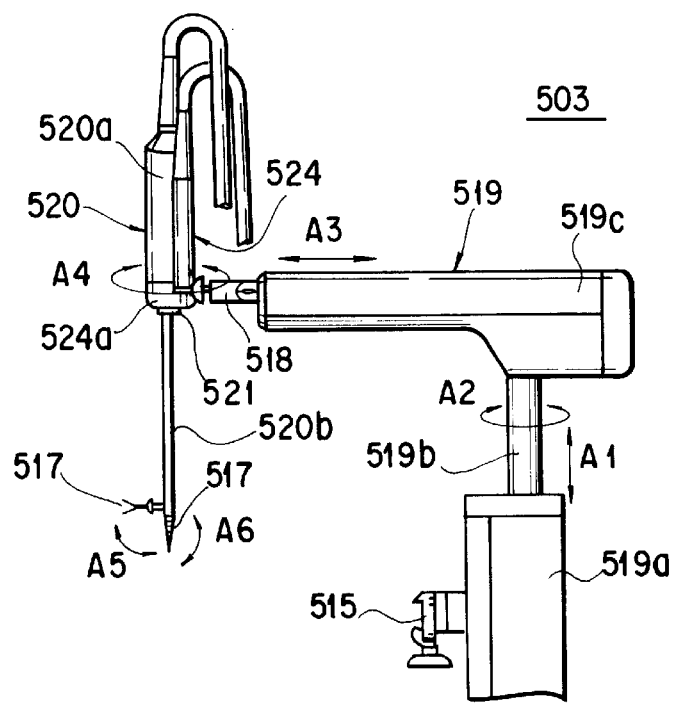
FIG. 52 is side view of the first manipulator incorporated in the nineteenth embodiment, which is equipped with a surgical instrument.

As shown in FIG. 52, the surgical manipulator 503 comprises an arm section (main body) 519, a holder section 524, and the medical instrument 520. The arm section 519 comprises a fixed shaft 519a, a first drive shaft 519b and a second drive shaft 519c. The fixed shaft 519a has a fastener 515 secured to the bedside rail 513. The first drive shaft 519b can move vertically (in the direction of arrow A1) and rotate around its axis (in the direction of arrow A2). The second drive shaft 519c can move horizontally (in the direction of arrow A3). The medical instrument 520 is removably attached to the holder section 524.

The holder section 524 is removably attached to the second drive shaft 519c of the arm section 519 by means of a universal joint 518 which is connected to the distal end of the second drive shaft 519c and which has some degrees of freedom. The holder section 524 contains a rotary mechanism for rotating the medical instrument 520 in the direction of arrow A4.

The medical instrument 520 comprises a grip 520a, an insertion section 520b and a holding forceps 517. The grip 520a is connected to the proximal end of the insertion section 520b and contains a drive mechanism. The insertion section 520b can be inserted into a body cavity and bent by operating the drive mechanism contained in the grip 520a. The holding forceps 517 is connected to the distal end of the insertion section 520b and can be opened and closed by operating the drive mechanism.

As shown in FIG. 53, the observation manipulator 504 comprises an arm section 519, the 3D scope 523 and a holder section 524. The arm section 519 and the holder section 524 are identical to those of the surgical manipulator 503. The 3D scope 523 is removably attached to the distal end of the holder section 524.

The 3D scope 523 comprises a grip 523a, an insertion section 523b and an imaging unit 522. The grip 523a is connected to the proximal end of the insertion section 523b and contains a drive mechanism. The insertion section 523b can be inserted into a body cavity and bent by operating the drive mechanism contained in the grip 523a. The imaging unit 522 is attached to the distal end of the insertion section 523b.

FIG. 54 illustrates a mechanism for connecting a medical instrument 520 or the 3D scope 523 to the holder section 524. As shown in FIG. 54, the holder section 524 has a first member 524a which is shaped like a flange and which extends in the lengthwise direction of the holder section 524. The first member 524a has a hole 529, through which the insertion section 520b of the medical instrument 520 or the insertion section 523b of the 3D scope 523 can pass. A screw 535 is formed on the proximal end portion of the insertion section 520b, and a screw 535 is formed on the proximal end portion of the insertion section 523b. Hence, when the insertion portion 520b or 523b is guide through the hole 529 of the first member 524a and a connecting nut 521 is set in screw engagement with the proximal end portion of the insertion section 520b or 523b, the instrument 520 or the 3D scope 524 is fastened to the holder 524. When the connecting nut 521 is released from the screw engagement with the proximal end portion of the insertion section 520b or 523b, the instrument 520 or the 3D scope 523 is easily disconnected from the holder 524.

Figure 55:
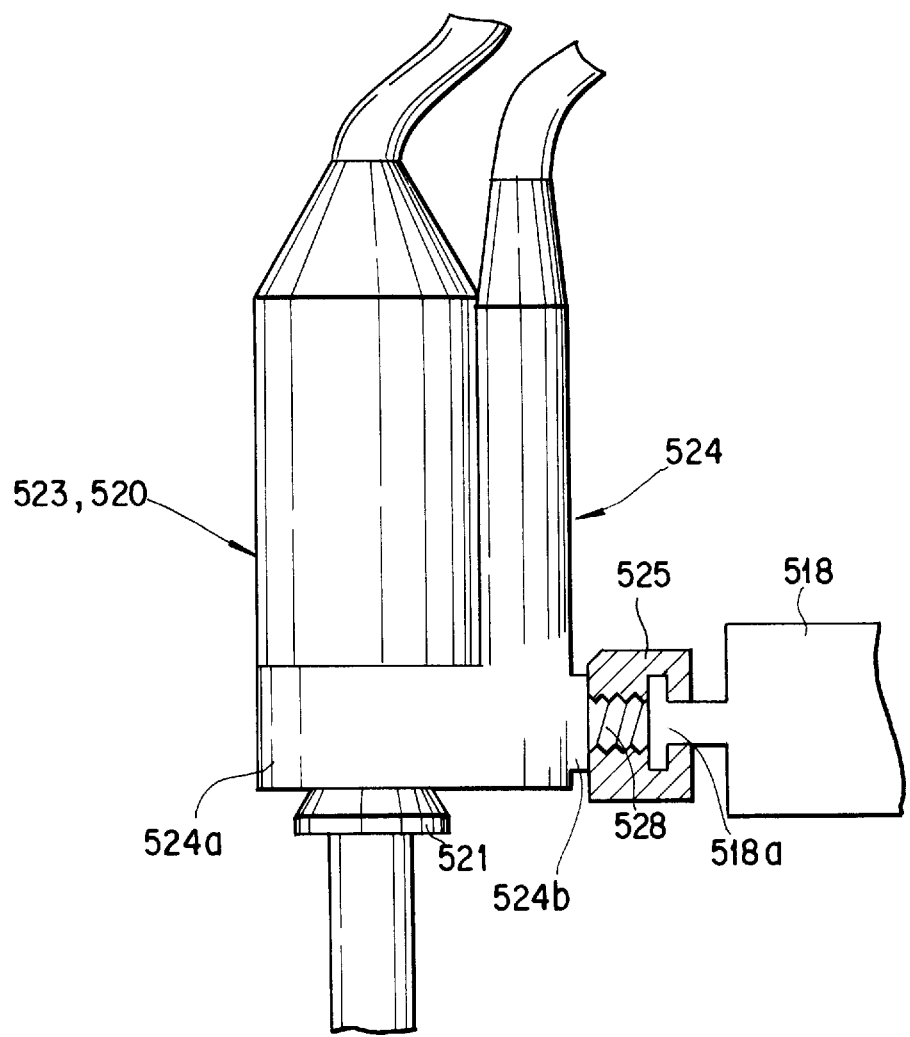
FIG. 55 is a sectional view showing a mechanism for connecting the holder section and arm section of the surgical manipulator used in the nineteenth embodiment.

FIG. 55 shows a mechanism for connecting the holder section 524 and the arm section 519. As already indicated, the holder section 524 is removably attached to the arm section 519 by the universal joint 518 which is connected to the distal end of the second drive shaft 519c. The holder section 524 can easily be coupled to the universal joint 518 by means of a single connecting nut 525.

As shown in FIG. 55, the universal joint 518 has a projection 518a having a flange at its distal end. The holder section 524 has a second member 524b which has a screw 528 cut in its circumferential surface. When the connecting nut 525 is set into engagement with the screw 528 of the second member 524b, with the connecting nut 525 mounted on the flange of the projection 518a, the holder section can be attached to the arm section 519.

When the connecting nut 525 is released from engagement with the screw 528, the holder section can easily be disconnected from the arm section 519.

The projection 518a of the universal joint 518 is made of electrically insulating material, and the holder section 524 is sealed in watertight fashion.

FIG. 56 shows the drive mechanism contained in the medical instrument 520 and the rotary mechanism contained in the holder section 524. FIG. 56 shows the case where the instrument 520 is attached to the holder section 524 by means of the connecting nut 521.

The rotary mechanism contained in the holder section 524 comprises an electric motor 545, a reduction unit 546, an encoder 550, a first pulley 547, a second pulley 548, and an endless belt 549. The motor 545, the reduction unit 546, the encoder 550 and the first pulley 547 are aligned substantially in a straight line. The reduction unit 546 is coupled to one end of the shaft of the motor 545, and the encoder 550 is connected to the other end of the motor 545. The first pulley 547 is mounted on the output shaft of the reduction unit 546. The components 545, 546, 550 and 547 are aligned in a substantially straight line. The second pulley 548 is a hollow cylinder secured to the first member 524a of the older section 524. The endless belt 549 is wrapped around the first and second pulleys 547 and 548. The rotation of the motor 545 can be transmitted to the medical instrument 520 fitted in the second pulley 548, by the reduction unit 546, the first pulley 547, the belt 549 and the second pulley 548. When the motor 545 is driven, the second pulley 578 is rotated, rotating the medical instrument 520.

As indicated above, the insertion section 520b of the medical instrument 520 has the holding forceps 517 fixed to its distal end. The insertion section 520b comprises a long pipe 538, a bending mechanism 537 and the forceps 517. The bending mechanism 537 has a plurality of segments which are coupled together, end to end, each rotatable with respect to either adjacent one. A pair of wires 539 and 540 are fastened, at one end, to the bending mechanism 537. The wires 539 and 540 are fastened, at the other end, to a first linear actuator 541 which is contained in the grip 520a and set in engagement with a pulley 561 incorporated in the grip 520a. When the linear actuator 541 is driven along its axis, one of the wires 539 and 540 is pulled, whereas the other wire is slackened, or vice versa. The segments of the bending mechanism 537 are thereby rotated, whereby the bending mechanism 537 turns upwards or downwards. Connected to the distal end of the linear actuator 541 is a free-lock mechanism 553, which will be described later.

A rod 542 is connected, at one end, to a link mechanism for opening and closing the holding forceps 517. The other end of the rod 542 is connected by a flexible rod 543 to one end of an operation rod 544. The other end of the operation rod 544 is connected to a second linear actuator 551 which is contained in the grip 520a. Therefore, when the second linear actuator 551 is driven along its axis, the rod 542, the operation rod 544 and the flexible rod 543 are thrust back and forth, actuating the link mechanism. The holding forceps 517 is thereby opened and closed.

The flexible rod 543 comprises an inner cable, a spring, a blade, and an outer casing. The inner cable is a strand of stainless wires connected to the operation rod 544, for transmitting a push and a pull to the operation rod 544. The spring is made of stainless steel, holding and protecting the inner cable. The blade covers the spring. The outer casing, which is made of ETFE, is sheath covering the blade.

The first linear actuator 541, which pulls and slacken the wires 539 and 540, comprises an electric motor 554, an encoder 555, a coupling 556, a feed screw 557 and a sliding mechanism 550. The encoder 555 is mounted on the shaft of the electric motor 554. The feed screw 557 is coupled to the motor 554 by the coupling 556. The sliding mechanism 550 is set in screw engagement with the feed screw 557 and connected to the wires 539 and 540.

Figure 57:
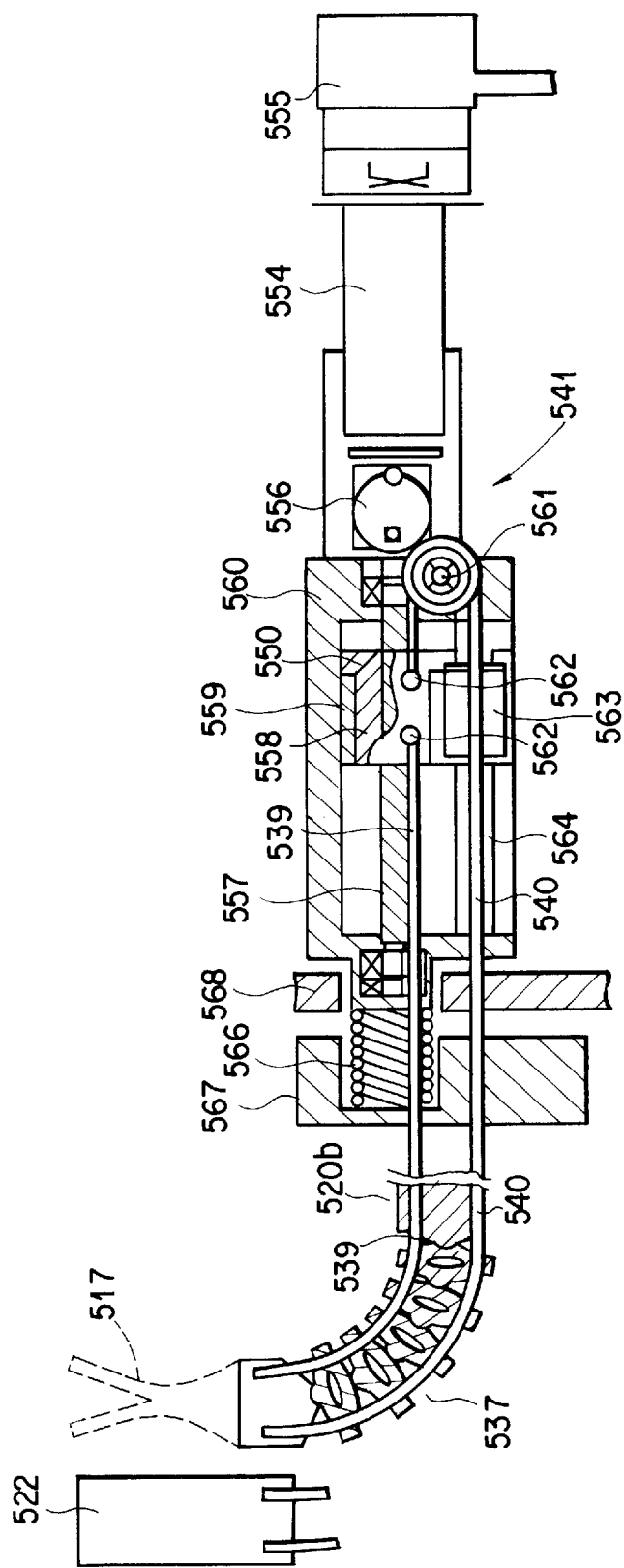
FIG. 57 is a side view of the bending mechanism of the medical instrument shown in FIG. 56.

As illustrated in FIG. 57, the sliding mechanism 550 comprises a nut 558, a nut housing 559 and a sliding shaft 564. The nut is mounted on the screw 557 and put in screw engagement therewith. The nut housing 559 supports the nut 558. The sliding shaft 564 enables the nut housing 559 to slide along the feed screw 557. A linear bush 563 extends parallel to the nut housing 559, in order to prevent the nut housing 559 from rotating. The sliding mechanism 550 is located, in its entirety, in a housing 560 which supports and holds the feed screw 557. A pulley 561 is rotatably connected to the housing 560. The wire 539 fastened to the bending mechanism 537 is fixed at its end to the nut housing 559 by a wire fastener 562. The wire 540, which is fastened to the bending mechanism 537, too, is wrapped around the pulley 561 and fixed at its end to the nut housing 559 by a wire fastener 562.

The second liner actuator 551 is identical to the first linear actuator 541, except for two respects. First, it has neither a wire fastener nor a pulley to fix the wire 539 or 540. Second, the operation rod 544 is secured to the bending mechanism 537.

The free-lock mechanism 553, which is connected to the distal end of the first linear actuator 541, will be described in detail, with reference to FIGS. 58A and 58B. As shown in these figures, the mechanism 553 comprises a compression spring 566, a spring holder 567, a sliding rod 569, a contact plate 565, and a guide member 568. The compression spring 566 is wound around the distal end portion of the housing 560. The spring holder 567 holds the compression spring 566, pushing the spring 566. The sliding rod 569 is connected to the spring holder 567 and can protrude outside the housing 560 through a hole 560a made in the distal end of the housing 560. The contact plate 565 is secured to the distal end of the sliding rod 569 and can abut on the first member 524a of the holder section 524 when biased by the compression spring 566. The guide member 568 guides the housing 560 in a predetermined direction.

Connected together by the sliding rod 569, the contact plate 565 and the spring holder 567 can move together, back and forth, along the axis of the medical instrument 520. Guided by the guide member 568, the housing 560 can move back and forth, also along the axis of the medical instrument 520.

The 3D scope 523 and the holder section 524 will be described in detail, with reference to FIG. 59.

Figure 59:
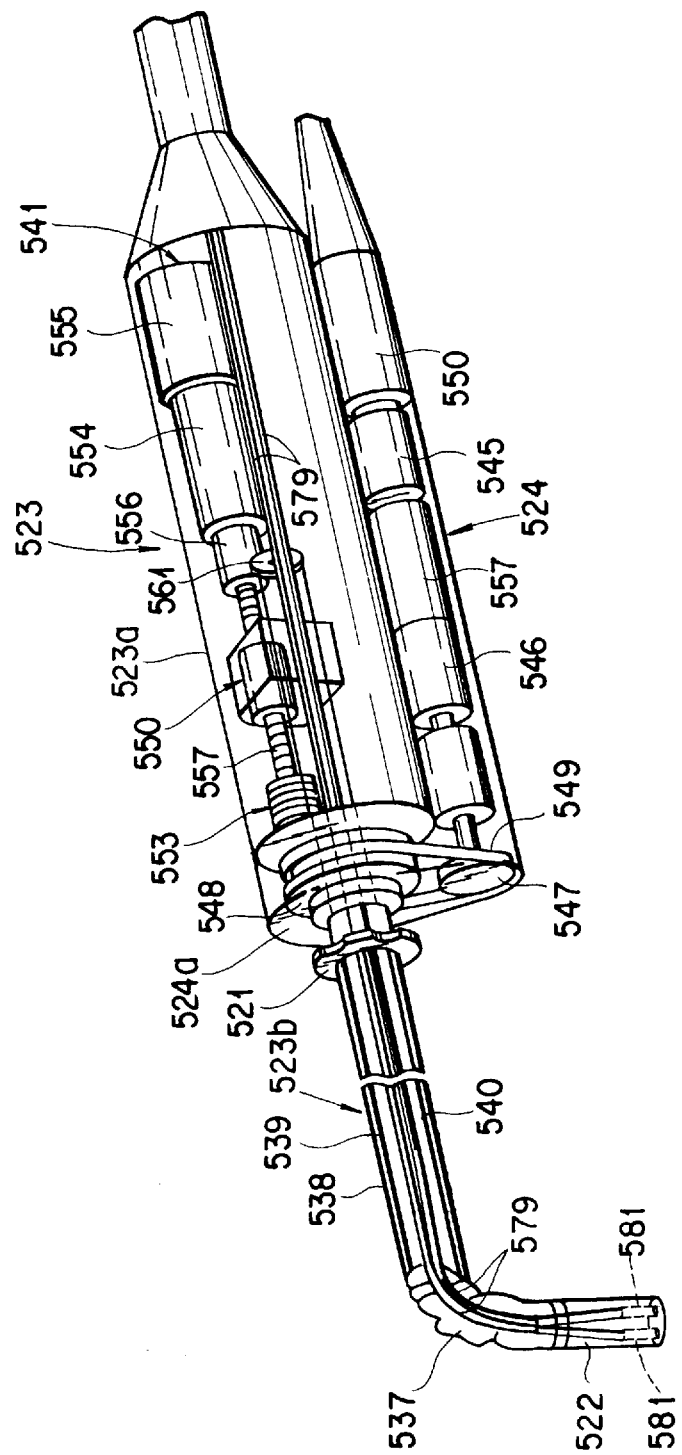
FIG. 59 is a perspective view of the 3D scope and holder section of the surgical manipulator shown in FIG. 50.

As can be seen from FIG. 59, the 3D scope 523 contains a bending mechanism, and the holder section 524 a rotary mechanism. In the condition shown in FIG. 59, the 3D scope 523 is fastened to the holder section 524 by the nut 531, as described above. The holder section 524 and the rotary mechanism contained in the section 524 are identical to those which have been described in detail with reference to FIG. 56. The components of the holder section 524 and the rotary mechanism are therefore designated at the same numerals as used in FIG. 56 and will not be described in detail.

The bending mechanism contained in the grip 523a of the 3D scope 523 is identical to the drive mechanism contained in the medical instrument 520, except that it has no second actuator to drive an operation rod. The bending mechanism will be described briefly.

As indicated above, the insertion section 523b of the 3D scope 523 has the imaging unit 522 attached to its distal end. The insertion section 523b comprises a long pipe 538, a bending mechanism 537 and the imaging unit 522.

The imaging unit 522 has two CCD cameras 581, each comprising a CCD sensor and an optical system. A cable 579 passes through the pipe 538 and electrically connects the CCD cameras 581 to a CCU 507 of the same type as those shown in FIG. 50.

The bending mechanism 537 has a plurality of segments which are coupled together, end to end, each rotatable with respect to either adjacent one. A pair of wires 539 and 540 are fastened, at one end, to the bending mechanism 537. The wires 539 and 540 are wrapped around a pulley 561 provided in the grip 523a and fastened, at the other end, to a linear actuator 541 contained in the grip 523a. The linear actuator 541 is identical in structure to the first linear actuator 541 incorporated in the medical instrument 520. When the linear actuator 541 is driven along its axis, one of the wires 539 and 540 is pulled, whereas the other wire is slackened, or vice versa. The segments of the bending mechanism 537 are thereby rotated, whereby the bending mechanism 537 turns upwards or downwards. Connected to the distal end of the linear actuator 541 is a free-lock mechanism 553 which is identical in structure to the mechanism 553 used in the medical instrument 520.

As can be understood from the preceding paragraph, the 3D scope 523 differs in structure from the medical instrument 520, only in that imaging unit 522 is used in place of the holding forceps 517. This may be best illustrated in FIG. 57 which shows imaging unit 522 along with the holding forceps 517.

The surgical manipulator system equipped with the manipulators 503 and 504 described above will now be explained.

Before the initiation of the surgery, the medical instrument 520 and holder section 524 of the surgical manipulator 503 have yet to be attached to the arm section 519. Both the instrument 520 and the holder section 524 are already sterilized.

To start the surgery, the arm section 519 is secured to the operating table 512 by means of the fastener 515. Next, the holder section 524 is attached to the projection 518a of the universal joint 518. More specifically, as shown in FIG. 55, the connecting nut 525 is set into engagement with the screw 528 of the holder section 524, while keeping the nut 525 in engagement with the flange of the 518a. Then, as shown in FIG. 54, the connecting nut 521 is set into engagement with the screw 535 of the insertion section 520b, with the section 520b inserted in the hole 529 of the holder section 524. As a result, the medical instrument 520 is attached to the holder section 524.

Similarly, the 3D scope 523 and the holder section 524 of the observation manipulator 504 have yet to be attached to the arm section 519 before the initiation of the surgery. Both the 3D scope 523 and the holder section 524 are already sterilized. To start the surgery, the arm section 519, the holder section 524, and the 3D scope 523 are sequentially secured to the operating table 512.

The surgeon operates the master manipulator 501, while looking at the image of the interior of a body cavity, which is displayed by the TV monitor 511 or the HMD 510. As th surgeon operates the master manipulator 501, the surgical manipulator 503 is operated in the same way, performing the surgery on the object in the body cavity. To state more specifically, the master manipulator 501 detects the position and orientation of the surgeon's hand, and supplies the information representing the position and orientation of the hand to the motor control unit 502. The unit 502 remote-controls the surgical manipulator 503 in accordance with the information. To be more precise, the unit 502 controls the first and second drive shafts 519b and 519c of the arm section 519, the rotary mechanism of the holder section 524 and the bending mechanism of the instrument 520 in accordance with the information supplied from the master manipulator 501. The holding forceps 517 fixed to the distal end of the surgical instrument 520 is thereby controlled to assume the position and orientation represented by the information.

The surgical manipulator 503 and the observation manipulator 504 may interfere with each other when the surgeon moves the master manipulator 501 too much, eventually positioning the surgical manipulator 503 too close to the 3D scope 523. Alternatively, the arm sections 519 of the manipulators 503 and 504 may be so positioned that neither the forceps 517 nor the 3D scope 523 can move to desired points in the body cavity. Either problem can be solved, merely by removing the instrument 520 and the 3D scope 523 from the first and second holder sections 524, respectively, and by switching the positions of the instrument 520 and the 3D scope 523.

After the surgery has been performed, the holder section 524 and the medical instrument 520 are removed from the arm section 519 and sterilized along with the 3D scope 523. The arm section 519 can be sterilized as well, but should better be covered with a piece of sterilizing cloth. The sterilizing cloth is taken off the arm section 519 and discarded after the section 519 has been thoroughly sterilized.

The operations of the surgical manipulator 503 and the observation manipulator 504 will be explained separately, to facilitate understanding.

It will first be described how to operate the surgical manipulator 503. Before used in surgery, the medical instrument 520 remains detached from the holder section 524 and sterilized, as described above. The instrument 520 is maintained watertight by means of an O-ring so that it may be sterilized well. The surgical manipulator 503 is positioned with its TCP located near the object of surgery. Then, the insertion section 520b is inserted into the trocar 530, while held in the hole 529 of the holder section 524. Thereafter, the medical instrument 520 is attached to the holder section 524 by means of the connecting nut 521.

In the holder section 524, the rotation of the electric motor 545 is transmitted to the second pulley 548 by the reduction unit 546 and the first pulley 547, the endless belt 549, as can be understood from FIG. 56. As the second pulley 548 is rotated, the medical instrument 520, which is fastened to the connecting nut 521, is rotated as a whole.

The holding forceps 517 fixed to the distal end of the surgical instrument 520 is driven by the first linear actuator 541. The forceps 517 holds the object when closed, and releases the object when opened. The bending mechanism 537 is bent upwards or downwards by the linear actuator 551. The free-lock mechanism 553 is operated by tightening the connecting nut 521, thereby attaching the medical instrument 520 to the holder section 524. Namely, the instrument 520 is set into locked condition in which the drive force of the linear actuator 541 is transmitted directly to the bending mechanism 537. When the connecting nut 521 is loosened, the instrument 520 is set into unlocked condition in which the bending mechanism 537 can be easily bent by external forces.

The operation of the free-lock mechanism 553 will be explained below.

Figure 58:
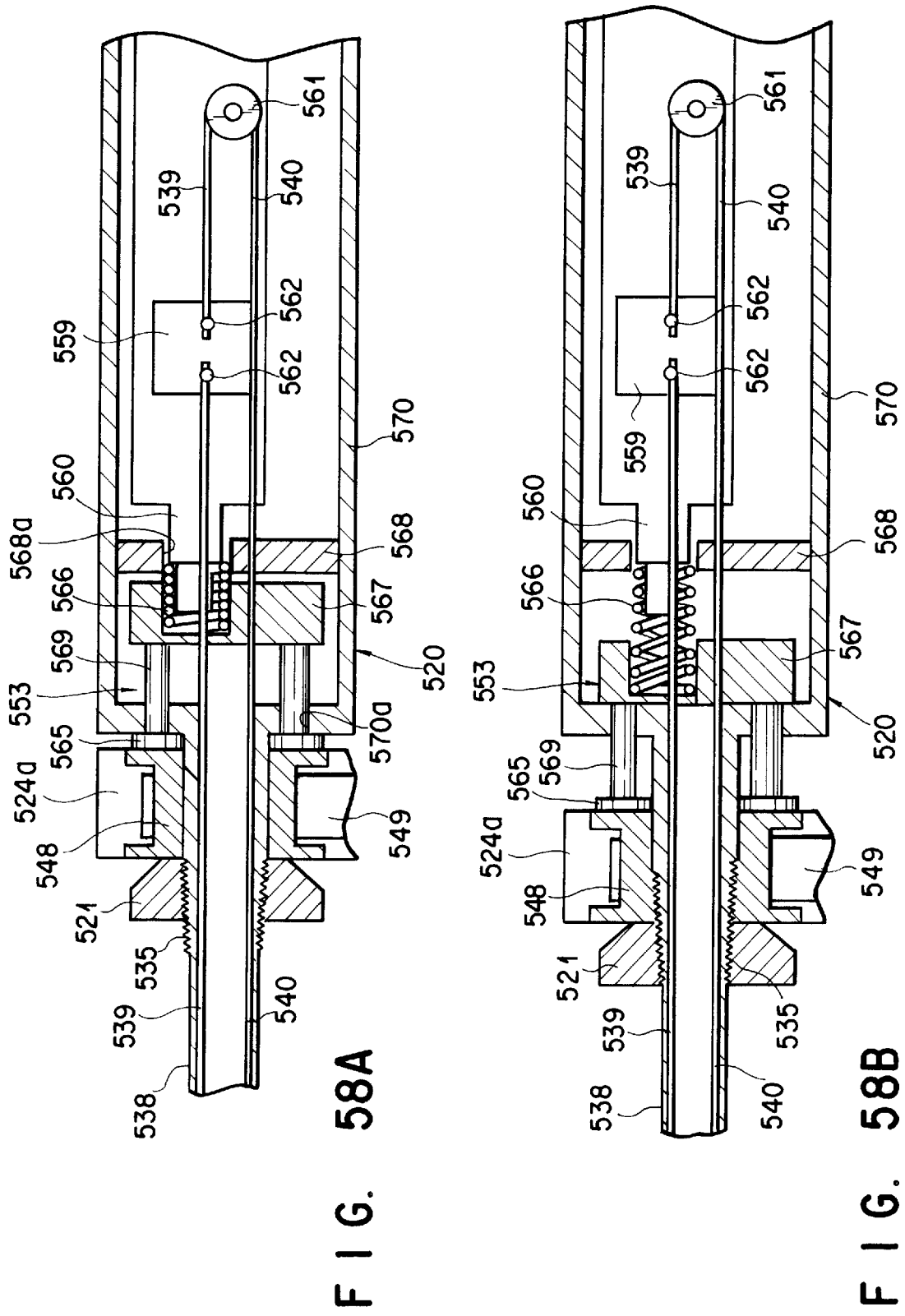
FIGS. 58A and 58B are sectional views illustrating the free-lock mechanism for the medical instrument shown in FIG. 56.

The connecting nut 521 is set in engagement with the screw 535 of the insertion section 520b, with the section 520b guided through the hole 529 of the holder section 524, as shown in FIG. 58B. Then, the pulley 548 of the holder section 524 contacts the contact plate 565. As the nut 521 is tightened, the contact plate 565, the sliding rod 569 and the spring holder 567 can move together, to the right, or toward the proximal end. As the spring holder 567 is moved to the right, it compresses the compression spring 566. The spring 566 urges the housing 560 of the first linear actuator 541 to slide to the right on the guide member 568. The compression spring 566 does not make the actuator 541 to slide so. Rather, its force increases the tension on the wires 539 and 540. This is because the housing 560 is fastened to the wires 539 and 540 by the pulley 561 and the nut housing 559. In other words, the spring 566 tightens the wires 539 and 540. Both wires 539 and 540 therefore transmit all drive force of the linear actuator 541 to the bending mechanism 537. The mechanism 537 is thereby bent reliably. Namely, the bending mechanism 537 is set in locked state by the linear actuator 541 and is bent in a desired manner.

When the connecting nut 521 is tightened, fastening the instrument 520 to the holder section 524, as illustrated in FIG. 58B, the compression spring 566 has but a small bias, and the tension on the wires 539 and 540 is low. The bending mechanism 537 can be bent easily by an external force. In this condition, the compression spring 566 absorbs the drive force of the first linear actuator 541. No large force is applied to the bending mechanism 537. The bending mechanism 537 is in an unlocked state.

The force of the compression spring 566 can be changed by tightening or loosening the connecting nut 521, to thereby vary the tension on the wires 539 and 540. To put it another way, it is possible to adjust the tension on the wires 539 and 540 by turning the connecting nut 521 in one direction or the other.

While remaining in the locked state, the bending mechanism 537 is driven by the first linear actuator 541 in the following way.

As already described, the bending mechanism 537 is bent by pulling the wire 539 and slackening the wire 540, or vice versa. It is the first linear actuator 541 (FIG. 57) that pulls and slacken each of these wires 539 and 540. When the electric motor 554 is driven, the feed screw 557 rotates, moving the nut housing 559 along with the nut 558. As the nut 558 is moved to the right in FIG. 57, the wire 539 is pulled to the right. At this time, the wire 540 is moved to the left since it is wrapped around the pulley 561. As a result of this, the bending mechanism 537 is bent upwards as illustrated in FIG. 57. Conversely, when the nut 558 is pulled to the left, pulling the wire 539 to the left and the wire wire 540 to the right, the bending mechanism 537 is bent downwards.

When the second linear actuator 551 is driven in the same way as the first linear actuator 541, the nut housing is moved to the left or the right. Then, the operation rod 544 is driven forward to open the holding forceps 517, or backward to close the holding forceps 517.

It will now be described how to operate the observation manipulator 504 by using the HMD 510 only, not using the TV monitor 511.

At first, the surgeon puts on the HMD 510. The left-eye image and the right-eye image, obtained by the CCD cameras 581, are supplied to the display 510a through the cable 579. The display 510a displays a 3D image of the interior of the body cavity, which the surgeon sees. The surgeon turns his or her head to see the object he or she intend to treat. The 3D digitizer 510b (i.e., the manipulator driver 505 shown in FIG. 50) detects the position and orientation of the surgeon's head and generates a signal representing the position and orientation of the head. In accordance with this signal, the motor control unit 502 controls the drive shafts 519b and 519c of the arm section 519, the rotary mechanism of the holder section 524 and the bending mechanism of the 3D scope 523, thereby setting the imaging unit 522 attached to the distal end of the 3D scope 523. This enables the surgeon to observe the object as if he or she were in the body cavity.

The holder section 524 and arm section 519 of the observation manipulator 504 are identical to those of the surgical manipulator 503. Therefore, the rotary mechanism in the holder section 524 and the bending mechanism 537 in the 3D scope 523, and the free-lock mechanism 553 operates in the same way as their counterparts of the surgical manipulator 503.

More specifically, in the holder section 524, the rotation of the electric motor 545 is transmitted to the second pulley 548 by the reduction unit 546 and the first pulley 547 and the endless belt 549. The second pulley 548 is thereby rotated, and the 3D scope 523, which is fastened to the connecting nut 521, is rotated as a whole.

The connecting nut 521 is set in engagement with the screw 535 of the insertion section 523b, with the section 523b guided through the hole 529 of the holder section 524, as shown in FIG. 58A. Then, the pulley 548 of the holder section 524 contacts the contact plate 565. As the nut 521 is tightened, the contact plate 565, the sliding rod 569 and the spring holder 567 can move together, to the right, namely toward the proximal end. Thereafter, the same sequence of operations takes place as in the surgical manipulator 503. Finally, all drive force of the linear actuator 541 is transmitted to the bending mechanism 537, and the mechanism 537 is thereby bent reliably. Namely, the bending mechanism 537 is set in locked state by the linear actuator 541. It is bent in a desired manner, against any external force applied to it.

When the connecting nut 521, which connects the 3D scope 523 to the holder section 524, is loosened as illustrated in FIG. 58B, the compression spring 566 has but a small bias, and the tension on the wires 539 and 540 is low. The bending mechanism 537 can be bent easily by an external force.

As explained above, the holder section 524 of either manipulator (503 or 504) can be detached from the universal joint 518 of the arm section 519. Once detached from the universal joint 518, the holder section 524 can be sterilized with ease. Similarly, since the medical instrument 520 and the 3D scope 523 can be removed from the respective holder sections 524, they can be easily sterilized, particularly those portions which have contacted living tissues located in the body cavity. Furthermore, once detached from the arm sections 519, the holder sections 523, the instrument 520 and the 3D scope 523 can be stored in sterilized condition and can therefore be maintained in better conditions than otherwise. The distal end of the 3D scope 523 may get dirty or clouded in the course of the surgery. If this happens, the 3D scope 523 can be removed from the holder section 519, washed and sterilized, and attached back to the holder section 519—within a short period of time. This serves to enhance the efficiency of surgery.

Since the projection 518a of the universal joint 518 is made of electrically insulating material, it electrically insulates the joint 518 from the holder section 524. An electric current would not flow to the arm section 519 from, for example, a cautery knife.

Various kinds of medical tools, such as a holding forceps, an ablation forceps, a needle-holding forceps, a clamp forceps and a cautery knife, can be attached to the distal end of the instrument instrument 520. The surgeon can fast replace the tool of any kind, attached to the instrument 520, with another tool of any other kind in the midst of the surgery.

As the surgery proceeds, the surgical manipulator 503 and the observation manipulator 504 may interfere with each other. The interference can be eliminated, merely by switching the instrument 520 and the 3D scope 523 in terms of their positions. This is possible simply because the arm sections 519 of the manipulators 503 and 504 are identical in structure. The surgeon can have great freedom of observing and treating the object of surgery. That is, the surgical manipulator system has high operability.

In the nineteenth embodiment, the medical instrument 520 and the 3D scope 523 are connected to and removed from the respective holder sections 524, in interlock with the operation of the free-lock mechanisms 553.

More precisely, when the instrument 520 is attached to the associated holder section 524, the free-lock mechanism 553 automatically locks the bending mechanism 537, whereby the drive force of the linear actuator 541 is reliably transmitted to the bending mechanism 537. When the connecting nut 521 is loosened to pull the instrument 520 from the body cavity, the free-lock mechanism 553 automatically unlocks the bending mechanism 537, regardless of the surgeon's intention. The bending mechanism 537 can thereby be bent freely, so that the surgeon can remove the instrument 520 from the body cavity, smoothly through the trocar 530.

Should the surgeon fail to unlock the bending mechanism 537 to remove the instrument 520 from the body cavity, the mechanism 537 is automatically unlocked when the surgeon loosens the nut 521. Once unlocked, the bending mechanism 537 can be bent freely. The instrument 520 can therefore be pulled from the body cavity, smoothly through the trocar 530, and the insertion section 520*b* of the instrument 520 is not damaged at all.

The surgeon need not be bothered to lock the bending mechanism 537 after attaching the instrument 520 to the holder section 524 or to unlock the mechanism 637 before removing the instrument 520 from the body cavity. The same holds true of the operation of the 3D scope 523. Hence, with the surgical manipulator system according the nineteenth embodiment it is possible for the surgeon to perform a transcutaneous endoscope surgery in high safety.

The free-lock mechanism 553 can not only interrupt and resume the transmission of a drive force to the bending mechanism 537, but also change this drive force by tightening the connecting nut 521 to any desired degree. If the data representing a bending angle desirable for the mechanism 537 has been destroyed, the drive force is be reduced greatly so that the mechanism 537 may easily be bent with an external force.

As has been described, the insertion section of either manipulator can be detached from the main section of the manipulator. Once detached from the main section, the insertion section can be sterilized with ease. Moreover, since some components other than the insertion section can be removed from the main section of the manipulator, they can be easily sterilized. Further, once detached from the main section, these components can be stored in sterilized condition and can therefore be maintained in better conditions. The manipulators may interfere with each other in the course of surgery. The interference can be eliminated, merely by switching the insertion sections of the manipulators in terms of their positions. In brief, the nineteenth embodiment gives the surgeon great freedom of observing and treating the object of surgery, makes it easy to sterilize the insertion sections (e.g., an endoscope and a medical instrument), and can eliminate interference, if any, between the insertion sections easily and quickly.

The twentieth embodiment of this invention will be described with reference to FIG. 60 and FIGS. 61A and 61B.

This embodiment is a surgical manipulator system which is similar, as a whole, to the system of the nineteenth embodiment (FIG. 50). The components similar or identical to those of the nineteenth embodiment are designated in FIGS. 60, 61A and 61B, and will not be explained in detail.

This embodiment is characterized by the provision of two fastening devices for fastening a master manipulator and a surgical manipulator, respectively. As shown in FIG. 60, the first fastening device 608 is connected to the proximal end of the master manipulator 501 and removably secured to the bedside rail 513 of the operating table 512. Similarly, the second fastening device 608 is connected to the proximal end of the surgical manipulator 503 and removably secured to the bedside rail 513.

The fastening devices 608 are identical in structure. Only the first fastening device 608 connected to the surgical manipulator 503 will be described below, in detail.

Figure 60:
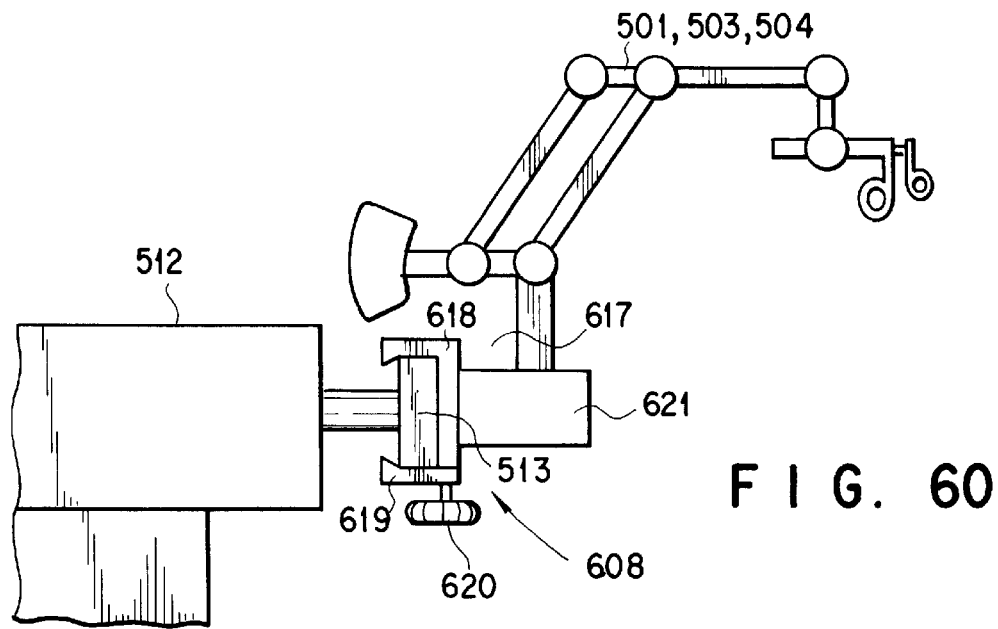
FIG. 60 is a side view of the fastening device used in the twentieth embodiment of the invention, for fastening a surgical manipulator to the operating table.
Figure 61A:
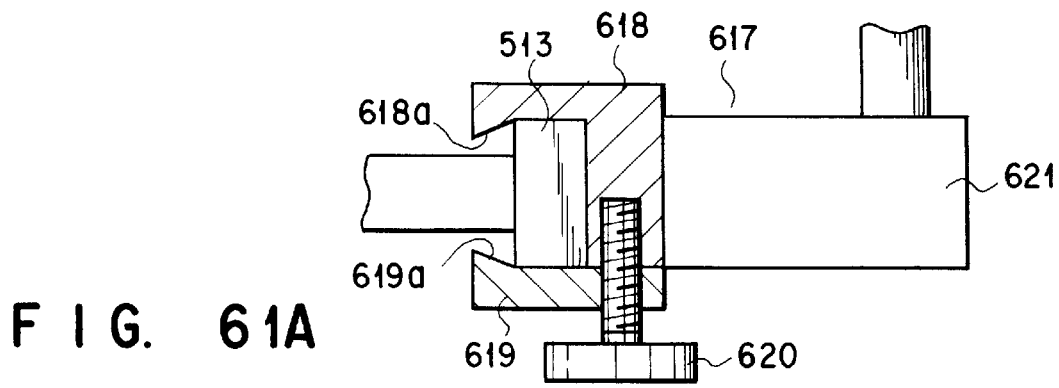
FIGS. 61A and 61B are vertical sectional views of the fastening device shown in FIG. 60.
Figure 61B:
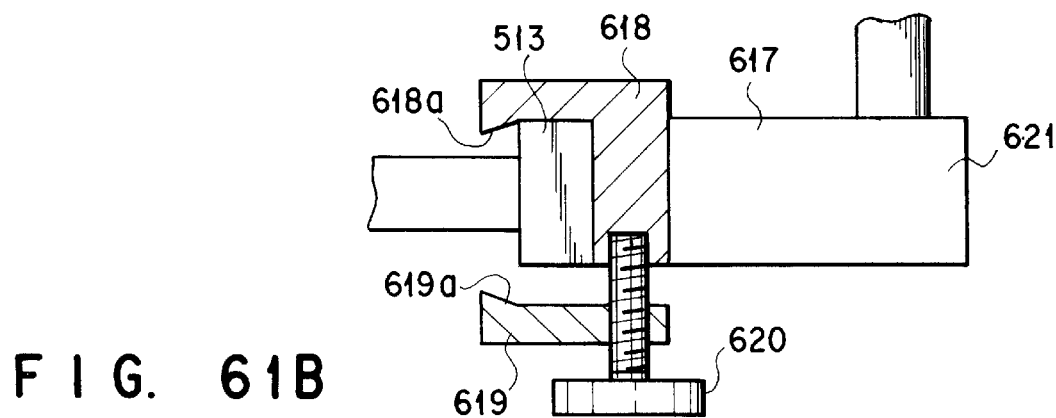

As shown in FIGS. 60, 61A and 61B, the first fastening device 608 comprises a clamp mechanism 617 and a main body 621. The main body 621 is connected to the proximal end of the surgical manipulator 503. The clamp mechanism 617 comprises a stationary clamp 618, a movable clamp 619, and a fastening knob 620. The stationary clamp 618 is connected to the main body 621. The clamps 618 and 619 have engagement members 618*a* and 619*a*, respectively. The members 618*a* and 619*a* can contact the upper end and lower end of the bedside rail 513, respectively. The stationary clamp 618 has a screw hole, whereas the movable clamp 619 has a through hole. The fastening knob 620 has a screw.

To secure the surgical manipulator 503 to the bedside rail 513, the fastening knob 620 is turned in one direction, with the screw passing through the hole of the movable clamp 619, thereby driving the screw into the screw hole of the stationary clamp 618. The clamps 618 and 619 clamp the bedside rail 513 between them, as shown in FIG. 61A. The surgical manipulator 503 is thereby fastened to the bedside rail 513.

To remove the surgical manipulator 503 from the bedside rail 513, the fastening knob 620 is turned in the opposite direction, moving the movable clamp 619 away from the stationary clamp 618, as shown in FIG. 61B. The fastening device 608 can then be removed, together with the manipulator 503, from the bedside rail 513.

In preparation for surgery to be performed by using the surgical manipulator system, the surgical manipulator 503 and the master manipulator 501 are secured to the same side of the operating table 512 as shown in FIG. 50, by means of the first and second fastening devices 608. An observation manipulator 504 is secured to the operating table 512. A medical instrument 520 is attached to the surgical manipulator 503, and a 3D scope 523 to the observation manipulator 504. The instrument 520 and the 3D scope 523 are inserted into a body cavity as illustrated in FIG. 50. An image of the interior of the body cavity, provided by the 3D scope 523, is displayed by the HMD 510 the surgeon 513 wears and also by the TV monitor 511 located near the operating table 512.

The surgeon 514 starts surgery on an object present in the body cavity. That is, he or she operates the master manipulator 501, thereby remote-controlling the surgical manipulator 503, while observing the image of the interior of a body cavity, which is displayed by the HMD 510 or the TV monitor 511.

As indicated above, the surgical manipulator 503 is fastened to the same side of the operating table 512 as the master manipulator 501. This means that the surgeon 516 remains within a reach of the surgical manipulator 503 while operating the master manipulator 501. Should it become necessary for the surgeon 516 to operate the surgical manipulator 503, as in emergency, he or she can immediately start operating the surgical manipulator 503. Since the surgeon 516 stands by the patient 514 while while operating the master manipulator 501, the patient 514 feels much relieved.

The twenty-first embodiment of the invention will be described with reference to FIGS. 62 and 63, which show the support mechanisms for a master manipulator 501 and a surgical manipulator 503.

Figure 62:
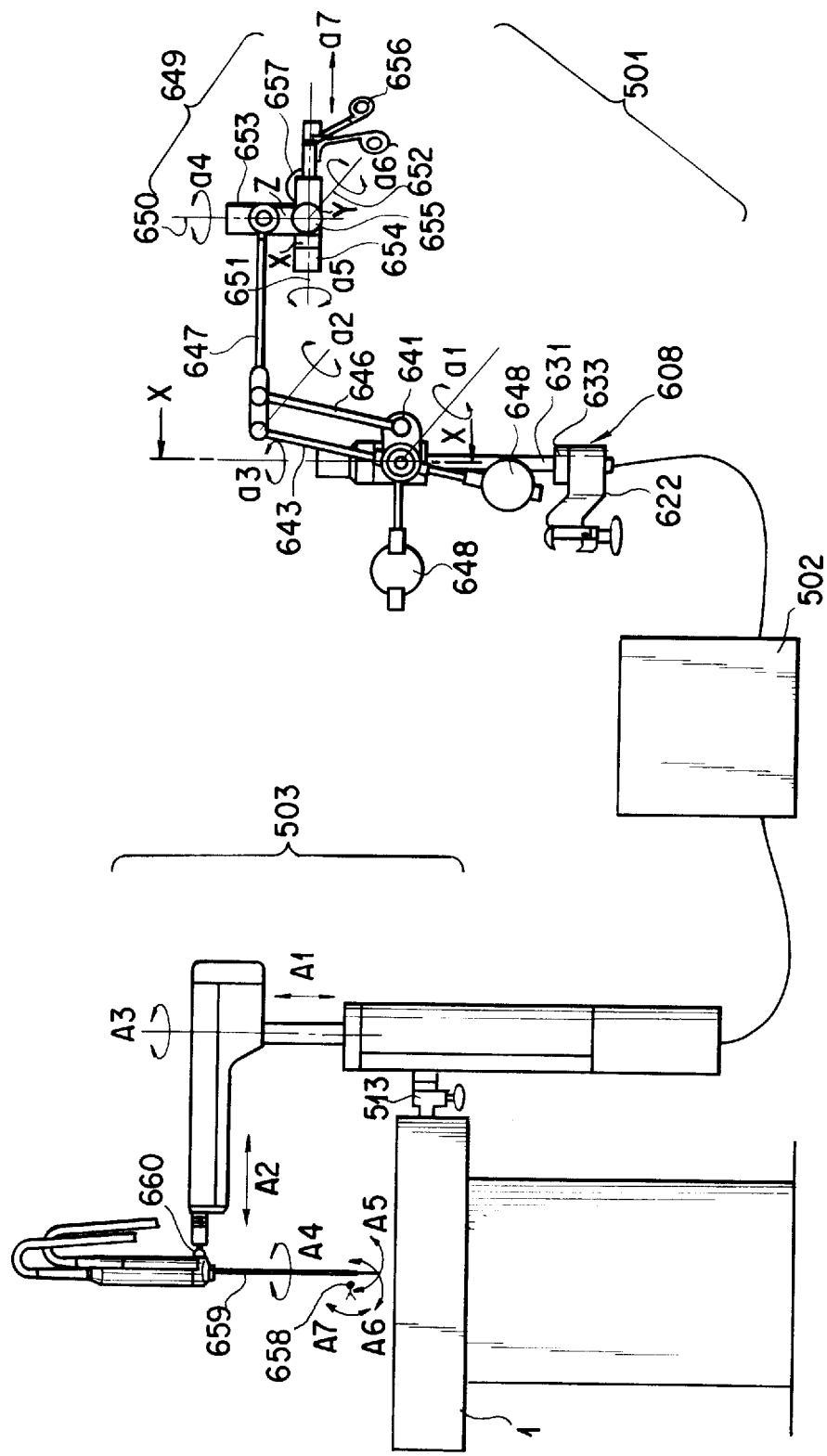
FIG. 62 shows the mechanisms supporting the manipulators incorporated in the surgical manipulator system according to the twenty-first embodiment of the present invention.

As shown in FIG. 62, a fastening device 608 of the same type used in the twentieth embodiment (FIG. 60) secures a master manipulator 501 to an operating table. To state more correctly, the vertical pillar 631 connected to the main body 622 of the device 608 supports the horizontal body 632 of the master manipulator 501. The pillar 631 can be moved vertically with respect to the device 608 by rotating a height-adjusting knob 633 mounted on the main body 622 of the fastening device 608.

Figure 63:
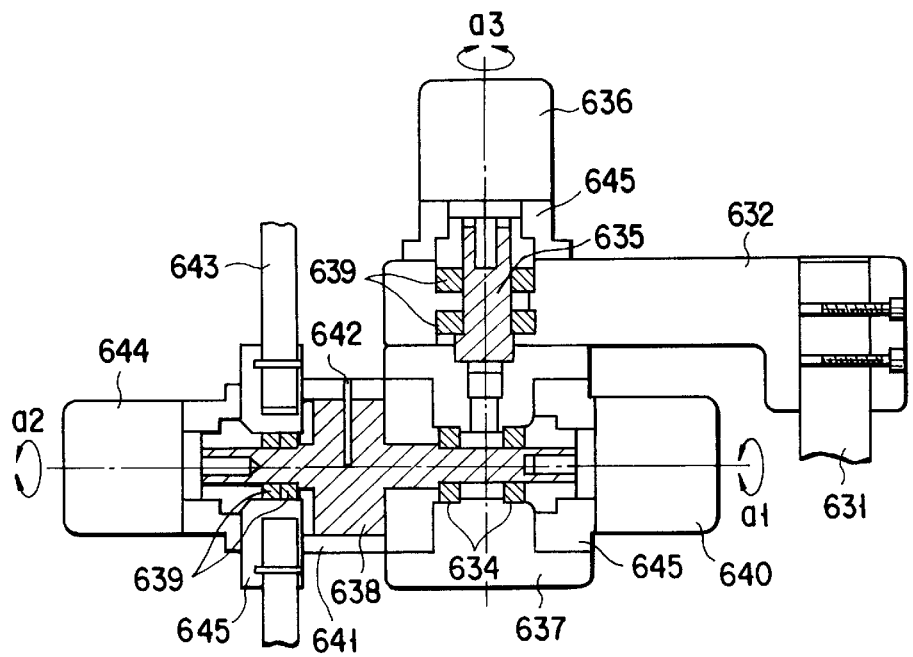
FIG. 63 is a sectional view taken along line X—X in FIG. 62.

As shown in FIGS. 62 and 63, the horizontal body 632 of the master manipulator 501 is mounted on a vertical shaft 635. The vertical shaft 635 is supported by a bearing 639 and can rotate around its axis $a_3$. Its angle of rotation is detected by an encoder 636 which is attached to the upper end of the vertical shaft 635. A horizontal member 637 is secured to the lower end of the vertical shaft 635 and is rotated around the axis $a_3$ when the shaft 635 rotates. A bearing 634 supports a horizontal shaft 638. An encoder 640 is connected to one end of the horizontal shaft 638, for detecting the angle by which the horizontal member 637 and the horizontal shaft 638 rotate relative to each other around an axis $a_1$. A horizontal arm 641 is fastened to the horizontal shaft 638 by means of a pin 642. A vertical arm 643 is supported by a bearing 639. An encoder 644 is connected to one end of the vertical arm 643, for detecting an angle by which the horizontal shaft 638 and the vertical arm 643 rotate relative to each other around an axis $a_2$. The encoders 636, 640 and 644 are mounted on three bases 645, respectively.

A vertical arm 646 is rotatably connected at its lower end to one end of the horizontal arm 641 such that the arm 646 remains parallel to the vertical arm 643 at all times. A horizontal arm 647 is rotatably connected at one end to the upper end of the vertical arm 643 and at a middle portion to the upper end of the vertical arm 646. The vertical arms 643 and 646 and the horizontal arms 641 and 647 constitute a parallel link. A weight 648 is connected to one end of the horizontal arm 641, and a weight 648 to one end of the vertical arm 643. These weights 648 serve to secure gravity balance among the arms 641, 643, 646 and 647.

As shown in FIG. 62, a handle section 649 is removably connected to the distal end of the horizontal arm 647. The handle section 649 has three axes 650, 651 and 652. An arm X, an arm Y and an arm Z can rotate around these axes 650, 651 and 652, respectively. The angles $a_4$, $a_5$ and $a_6$ through which the arm X, the arm Y and the arm Z are rotated can be detected by encoders 653, 654 and 655. The angle by which a handle 656 rotates can be detected by an encoder 657. The information representing the angles of rotations, which the encoders 636, 640, 644, 653, 654, 655 and 657, is supplied to a motor control unit 502.

The motor control unit 502 calculates the position and orientation of the handle section 649 from the information, the lengths of the vertical arms 643 and 646 and the lengths of the horizontal arm 647. The unit 502 controls the surgical manipulator 503 in accordance with the position and orientation of the handle section 649 and the angle of rotation of the handle 656 detected by the encoder 657. More precisely, the unit 502 moves the vertical support of the manipulator 502 in the direction of arrow $A_1$, rotates the vertical support in the direction of arrow $A_2$, and moves the horizontal arm of the manipulator 503 in the direction of arrow $A_2$. Further, the unit 502 rotates the insertion section 659 of the manipulator 503 in the direction of arrow $A_4$, bends the distal end portion of the manipulator 503 in the direction of arrow $A_5$ or $A_6$, and open or closes the instrument 658 attached to the distal end of the manipulator 503. The horizontal arm and the insertion section 659 are connected, end to end, by a free joint 660.

When the surgeon 516 holds and moves the handle 656 in any direction in a space, the encoders detect the angles of rotation around the axes $a_1$ to $a_6$. From these angles of rotation and the lengths of the arms 643, 646 and 647, the motor control unit 502 calculates the position and orientation of the handle section 649. In accordance with the position and orientation of the section 649, the unit 502 remote-controls the surgical manipulator 503, making the manipulator 503 assume the position corresponding to that of the handle section 649 and the same orientation as that of the handle section 649. When the surgeon 516 opens or closes the handle 656, the encoder 657 detects the angle of rotation of the handle 656, and the motor control unit 502 controls the surgical manipulator 503 such that the instrument 658 is opened or closed by the same angle of rotation.

The master manipulator 501 of the twenty-first embodiment comprises arms supported and connected by rotary mechanisms, other arms constituting a parallel link, and encoders for detecting angles by which various parts are rotated around various axes. The position and orientation of the surgeon's hand are determined from the angles of rotation detected by the rotary encoders. Therefore, this embodiment is advantageous in the following respects:

a) The master manipulator is compact enough not to lower the efficiency of surgery. All movable parts of the master manipulator are rotatably supported, and no linear drive elements such as ball screws are required to drive the movable parts. The master manipulator can therefore be operated quite smoothly.

b) The parallel link enables the surgeon to move the handle in a relatively large space, whereby the tool center point (TCP) of the surgical manipulator can be moved in as large a space.

c) The position and orientation of the surgeon's hand are detected by rotary encoders which are not influenced by vibration. The system can be used along with any other surgical system that generates much vibration, and can therefore be versatile. Since the surgeon only needs to manipulate the handle to perform surgery, he or she need not make any complicated preparation or acquire any special skill. This helps to shorten the operation time and lighten the surgeon's burden.

The twenty-second embodiment of the invention will be described with reference to FIGS. 64 to 66 and FIGS. 67A and 67B.

Figure 64:
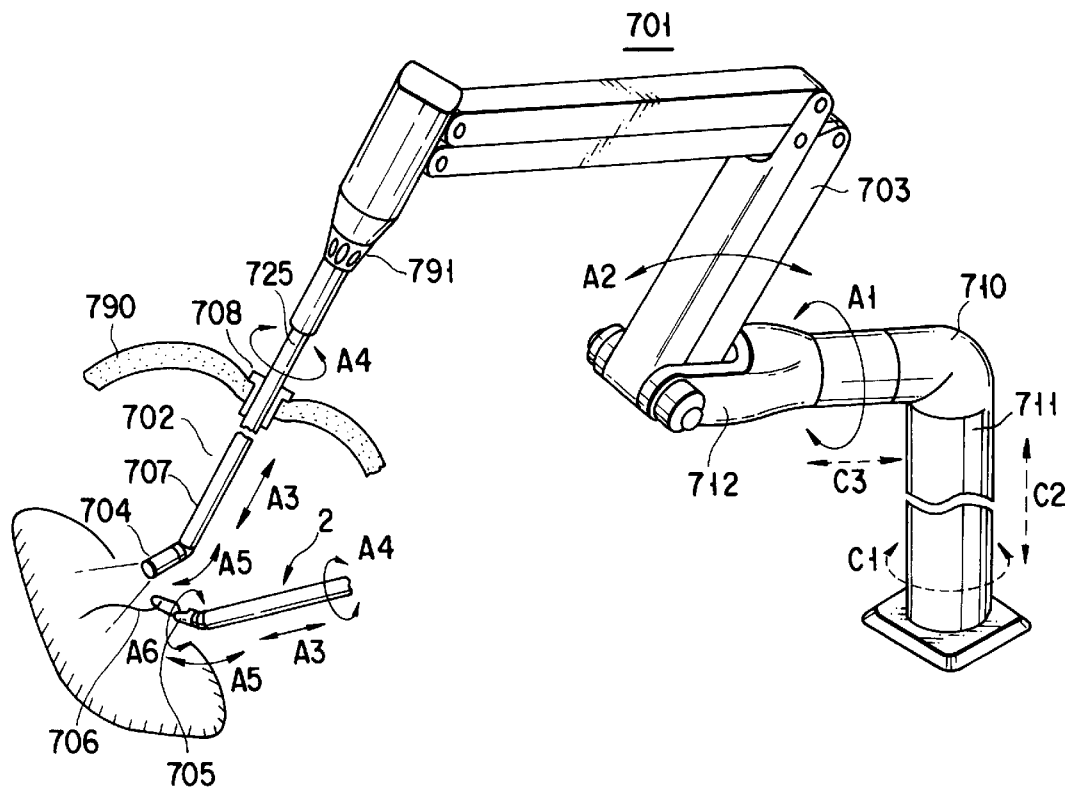
FIG. 64 is a perspective view of the surgical manipulator used in the surgical manipulator system according to the twenty-second embodiment of this invention.
Figure 65:
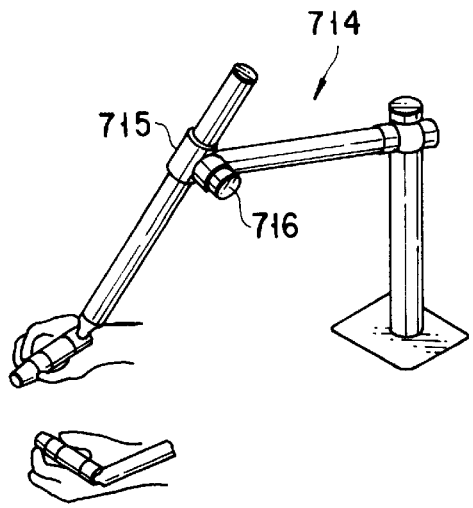
FIG. 65 is a perspective view of the master manipulator which is incorporated in the system according to the twenty-second embodiment and which has an arm for generating an operation command to the surgical manipulator.

As shown in FIG. 64, the surgical manipulator 701 of this embodiment comprises a manipulator body 703 and a straight insertion section 702. The manipulator body 703 is a multi-joint arm and has a point-locking mechanism and a position adjusting mechanism, both designed to position the insertion section 702. The insertion section 702 is connected at its proximal end to the distal end of the manipulator body 703. The section 702 is thin enough to be inserted into a body cavity through an opening 708 incised in the body wall 790. An endoscope 704, used as an end effector, is attached to the distal end of the insertion section 702. Although not shown in FIG. 64, the twenty-second embodiment has another surgical manipulator which is identical to the manipulator 701. A medical instrument 705, used as an end effector, is attached to the distal end of the insertion section of the other surgical manipulator. What kind of an end effector should be attached to the either surgical manipulator depends on which type of surgery is to be performed.

As shown in FIG. 64, only one bent part is provided between the insertion section 702 and the endoscope 704. The same is true of the insertion section 702 of the other surgical manipulator and the medical instrument 705. The endoscope 704 and the instrument 705 are much shorter than the insertion section 702 of either surgical instrument. The endoscope 704 has an illumination unit and an observation unit. The medical instrument 705 has a forceps 706 for holding tissues, for peeling tissues off an organ, effecting suture or holding a needle.

The number of axes the manipulator 701 has is determined by the degree of freedom needed in order to set the end effecter in any desired position and any desired orientation, and also by the position of the opening 708 which is incised in the body wall 790.

Generally, the manipulator body 703 must have six degrees of freedom in order to observe or treat an organ located at a given position in the body cavity. Since the image obtained by the endoscope 704 is rotated by means of image processing, however, five degrees of freedom are sufficient for the manipulator body 703. By contrast, the manipulator body of the other surgical manipulator (not show) having the medical instrument 705 as end effecter, needs to have six degrees of freedom. As for the position of the opening 708, it is required that the TCP of the insertion section 702 of either surgical manipulator be maintained at a specific position with respect to the opening 708 throughout the surgery. Otherwise, the insertion section 702 would apply an excessive force on the body wall 790. To this end, the insertion section 702 must be held immovable in three axes, and accordingly needs to have three degrees of freedom.

Therefore, the surgical manipulator 701 having the endoscope 704 must have eight degrees of freedom, whereas the surgical manipulator (not shown) having the instrument 705 must have nine degrees of freedom. It follows that the manipulator 701 needs to have eight axes, and the manipulator (not shown) nine axes. Nonetheless, the surgical manipulator 701 shown in FIG. 64 may require but only five axes, by virtue of the provision of a point-locking mechanism illustrated in FIG. 66.

Figure 66A:
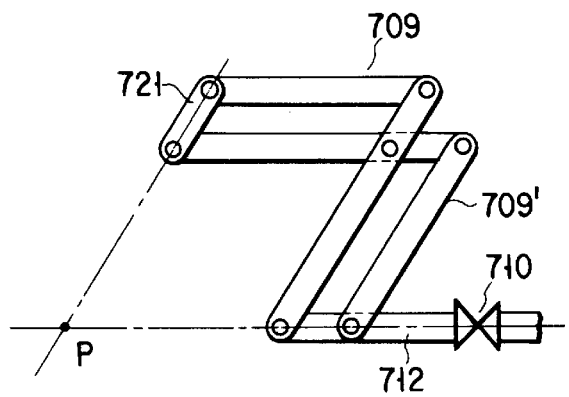
FIGS. 66A and 66B are diagrams of the point-locking mechanism for positioning the surgical manipulator shown in FIG. 64.
Figure 66B:
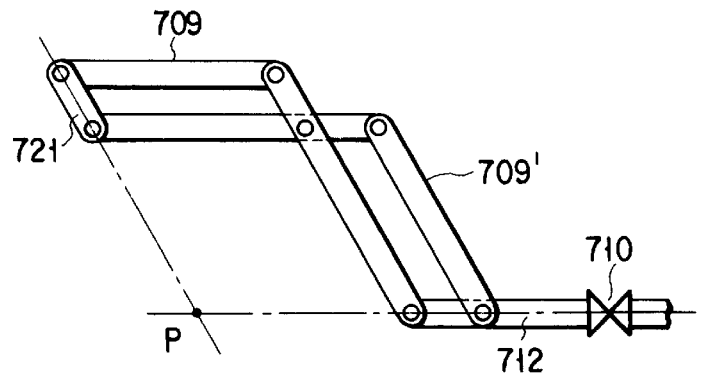

As shown in FIGS. 66A and 66B, the point-locking mechanism is comprised of six bars which are rotatably linked by six fulcrum pins, forming two parallelogrammatic links 709 and 709! which are contrapositive to each other. The first parallelogrammatic link 709 is the distal part of the point-locking mechanism, and the second parallelogrammatic link 709' is the proximal part thereof. A shaft 710 is connected to the bar 712 which is stationary and one of the four bars constituting the second link 709'. The point-locking mechanism can therefore be rotated around the axis of the bar 712 when the shaft 710 is rotated. Point P at which the axis of the stationary bar 712 intersects with that of the bar 721 of the first link 709 does not move at all, no matter how the six bars are moved in the same plane as the manipulator body 703 swings and how much the point-locking mechanism is rotated around the axis of the stationary bar 712.

As mentioned above, the manipulator body 703 has a position adjusting mechanism which is located at the proximal side of the point-locking mechanism. The position adjusting mechanism is a support section 711 shown in FIG. 64. The section 711 can rotate around its axis (in the direction of arrow C1 in FIG. 64) and which can move up and down (in the direction of arrow C2). The section 711 supports the shaft 710, which can be rotate (in the direction of arrow A1) and back and forth (in the direction of arrow C3). Therefore, when the support section 711 is moved vertically and the shaft 710 is moved linearly with respect to the section 711, the position and orientation of the stationary bar 712 is changed. Ultimately, the point P defined above is moved. Needless to say, once the position adjusting mechanism and the second link 709' are locked after the point P has been shifted to a desired position, the point P remains at that position even if the second link 709' is rotated in the direction of arrow A2 and the stationary bar 712 is rotated around its axis.

Hence, once the position adjusting mechanism has been so adjusted that the insertion section 702 is set in a specific position in the opening 708, the insertion section 702 remains at this position even if the position adjusting mechanism is moved. Thus, when the position adjusting mechanism is operated, with the point P located at the opening 708, the TCP of the insertion section 702 can be freely moved in the body cavity without exerting any excessive force to the body wall 790. Since the point-lock mechanism prevents the insertion section 702 from moving in the opening 708 incised in the body wall 790 when the manipulator 701 s operated, the insertion section 702 need not have three degrees of freedom. It suffices for the surgical manipulator 701 to have five axes in the case where the endoscope 704 is used as the end effecter, or six axes in the case where the medical instrument 705 is used as the end effecter.

The mechanism for driving the insertion section 702 with the endoscope 704 used as the end effecter will be described, with reference to FIGS. 67A and 67B.

Figure 67A:
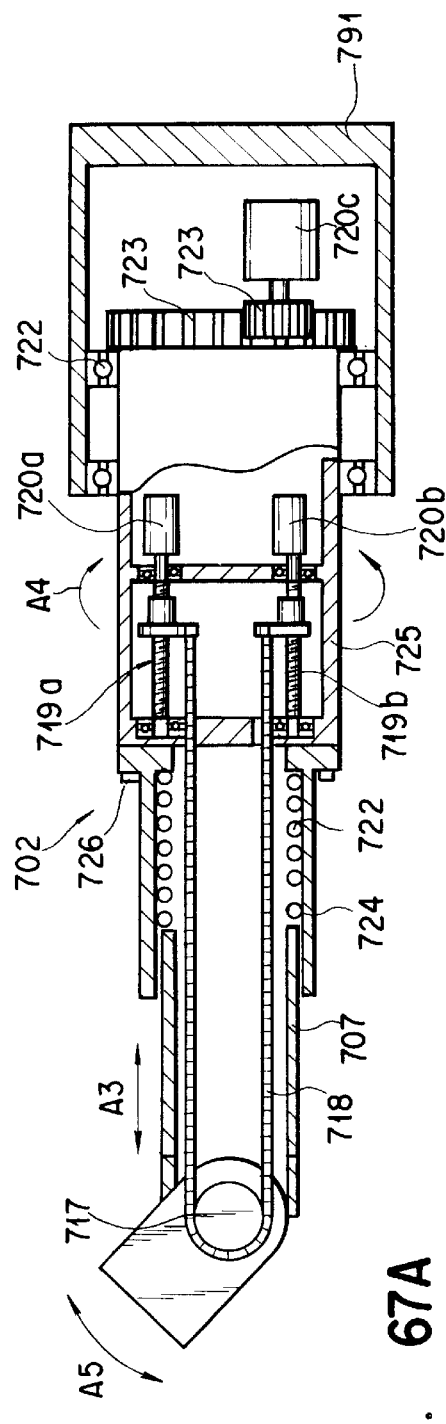
FIGS. 67A and 67B are sectional views showing the mechanism for driving the insertion section of the surgical manipulator shown in FIG. 64.
Figure 67B:
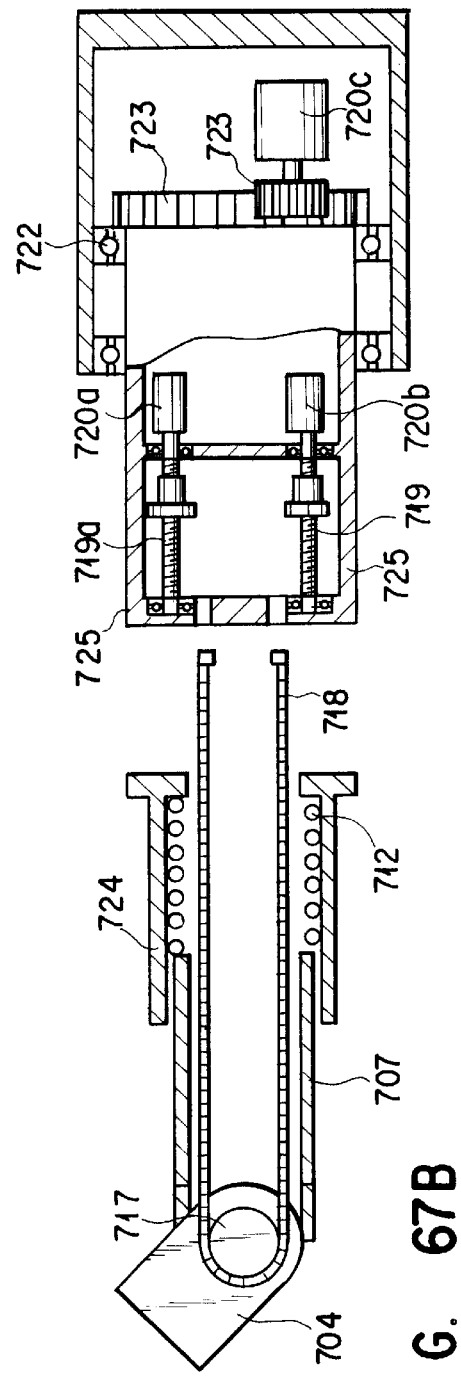

As shown in FIG. 67A, the insertion section 702 comprises a movable cylinder 707, a guide cylinder 724 and a rotary cylinder 725. The cylinder 707 can move back and forth. The guide cylinder 724 supports and guides the movable cylinder 707. The rotary cylinder 725 supports the guide cylinder 724 and can rotate in the direction of arrow A4. The rotary cylinder 725 has the above-mentioned bar 721 and supported by a proximal section 791 which moves in the same way as the bar 721.

A pulley 717 is fastened to a member which supports the endoscope 704 and which can be moved to rotate the endoscope 704 in the direction of arrow A5. A wire 718 is wrapped around the pulley 717. The ends of the wire 718 are fastened to two ball screws 719a and 719b, which are rotatably supported in the rotary cylinder 725. The ball screws 719a and 719b are rotated by electric motors 720a and 720b, respectively. The movable cylinder 707 is biased toward the distal end of the insertion section 702, by a spring 732 always applying a tension on the wire 718.

When the motors 720a and 720b are driven, the ball screws 719a and 719b pull the respective ends of the wire 718 to the right. Subsequently, the movable cylinder 707 is moved to the right for half the sum of the distances the ends of the wire 718 have been pulled. The pulley 717 is thereby rotated in the direction of arrow A5 by a circumferential distance equal to the difference between the distances the ends of the wire 718 have been pulled to the right.

The rotary cylinder 725 is supported by a bearing 722 and connected to an electric motor 720c by gears 723. The guide cylinder 724 is fastened to the rotary cylinder 725 by bolts 726. When the bolts 726 are unscrewed and the wire 718 is disconnected from the ball screws 719a and 719b, the movable cylinder 707 and the guide cylinder 724, both to be inserted into a body cavity, can be removed from the proximal portion of the insertion section 702, as is illustrated in FIG. 67B. The movable cylinder 707 and the guide cylinder 724 can then be washed and sterilized.

The components of the surgical manipulator 701 shown in FIG. 64 are linearly moved or rotated in the directions of arrows A1 to A6 by means of actuators and transmission members. The actuators are driven in accordance with commands generated by a controller (not shown) electrically connected to the surgical manipulator 701. The controller can generate commands by playback method and master-slave method. In the playback method, the controller generates commands from the operation patterns already programmed and stored. In the master-slave method, the controller generates commands as a surgeon operates a master manipulator 714 shown in FIG. 65. The master manipulator 714 has a multi-joint mechanism 715 and encoders 716. The mechanism 715 has as many degrees of freedom as the surgical manipulator 701. The encoders are provided at the respective joints of the mechanism 715.

As explained above, the surgical manipulator 701 has five degrees of freedom (arrows A1 to A5) when the endoscope 704 is used as end effecter, and six degrees of freedom (arrows A1 to A6) when the medical instrument 705 is used as end effecter. The point-lock mechanism and the position adjusting mechanism cooperate to set the TCP of the insertion section 702 at a desired position in a body cavity. More precisely, the components of the point-lock mechanism are moved in the directions of arrows C1, C2 and C3, thereby setting the point P in the opening 708, and the components of the position adjusting mechanism are moved in the directions of arrows A1 and A2, thereby setting the TCP of the insertion section 702 at the desired position in the body cavity.

The TCP of the insertion section 702 is then moved to a target object in the body cavity, by moving the components of the insertion section 702 in the directions of arrows A3, A4 and A5. Namely, the TCP of the end effecter attached to the distal end of the movable cylinder 707 is brought to the target object as the cylinder 707 is moved in the direction of arrow A3, the rotary cylinder 725 is rotated in the direction of arrow A4, and the end effecter is rotated in the direction of arrow A5. Since the movable cylinder 707 is straight and thin, it approaches the target object from the opening 708 in a straight path, not contacting any other object present in the body cavity. The end effecter is rotated to have its orientation adjusted, thus having its TCP located exactly at the target object. The end effecter does not contact any other object, either, while being rotated. This is because it is far shorter than the movable cylinder 707.

As has been described, the surgical manipulator 701 is so designed that the TCP of the end effecter coupled to the insertion section 702 can move in a large space in a body cavity, and that neither the insertion section nor the end effecter contacts any object other than the target object. In other words, the manipulator 701 has many degrees of freedom, applying no excessive force on the target object and enabling the end effecter to treat the target object or provide the surgeon with an image of the target object. It is desired that the end effecter have a length one-fifth or less the length of the movable cylinder 707, as measured from the center of the pulley 717.

Figure 68:
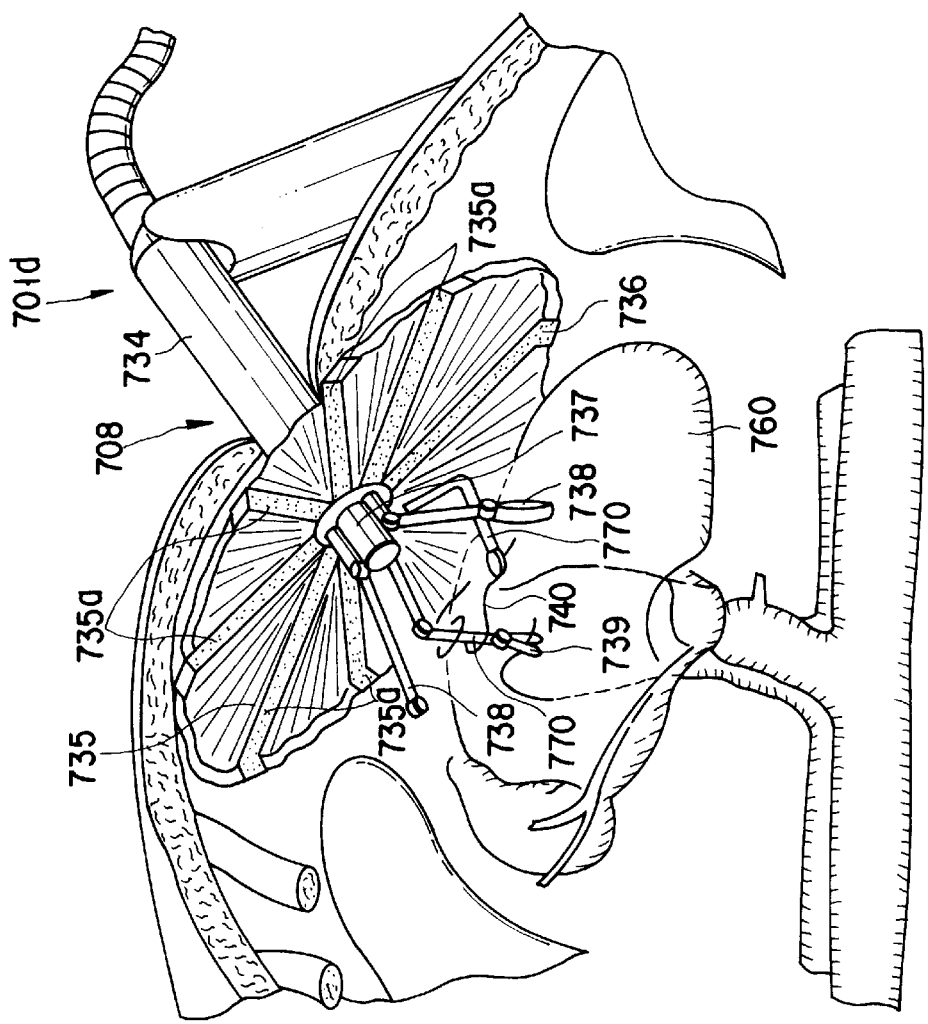
FIG. 68 is a diagram explaining how to approach to the kidney the insertion section of the surgical manipulator used in the twenty-third embodiment of the invention.

The twenty-third embodiment of the invention will be described with reference to FIG. 68 and FIGS. 69A to 69D. FIG. 68 shows a surgical manipulator 701d which is designed to extract the kidney 760. The main body of the manipulator 701d has the same structure as that of the surgical manipulator used in the first embodiment. Alternatively, the main body may have a different structure.

The surgical manipulator 701d comprises a straight insertion section 734, an expander 735, a tissue crusher 736, a 3D endoscope 737, micro-manipulators 738, and two-armed micro-manipulators 770. The expander 735 is mounted on the distal end of the insertion section 734. It is constructed like a parasol, having a plurality of ribs 735a and a flexible cover connected to the ribs 735a, and can be opened after inserted into a body cavity. The tissue crusher 736 and the 3D endoscope 737 are connected to the expander 735 and located inside thereof. The micro-manipulators 738 are connected to the distal end of the insertion section 734, for holding an ablation forceps and a pusher-remover. The two-armed micro-manipulators 770 are provided to apply a suture. A touch sensor 739 is mounted on the holding surface of the first two-armed micro-manipulator 770. The kidney 760 is severed from the urethra and the kidney artery is too large to pass through an opening 708 incised in the body wall. To extract the kidney 760 outside the body wall, the expander 735 is closed, wrapping up the kidney 760, and the tissue crusher 736 is driven, crushing the kidney 760. The tissue crusher 736 has an ultrasonic oscillator for crushing the kidney 760 and a suction device for extracting the crushed tissue.

Figure 69C:
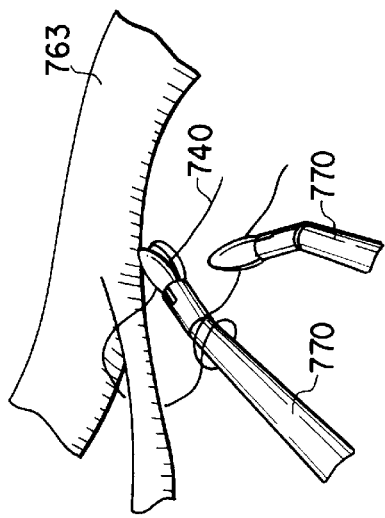
FIGS. 69A to 69D are diagrams for explaining how the end effecter of the surgical manipulator shown in FIG. 68 is operated in order to suture an artery.
Figure 69D:
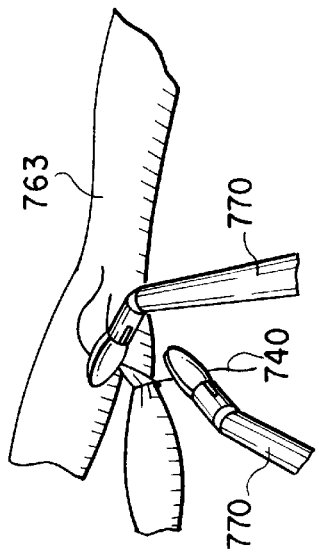
Figure 69A:
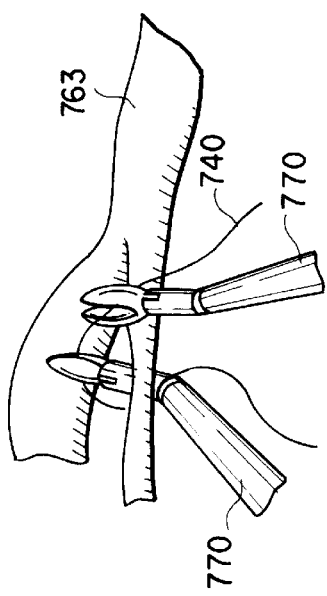
Figure 69B:
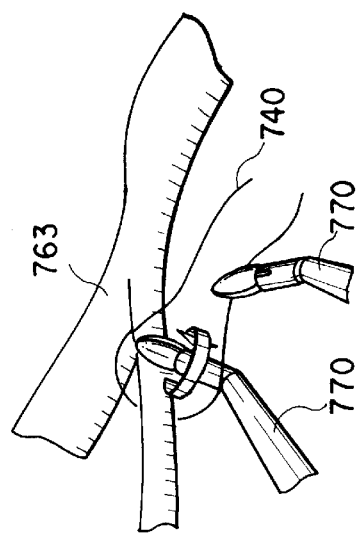

FIGS. 69A to 69E show how the two-armed micro-manipulators 770 are operated to tie up the kidney artery 763 before the kidney 760 is severed from the kidney artery 763. First, the micro-manipulators 770 are operated to wrap a suture 740 around the artery 763 as illustrated in FIGS. 69A and 69B. Then, they are operated to tighten the suture 740, tying up the kidney artery 763, as shown in FIGS. 69C and 69D. The two-armed micro-manipulators 770 automatically conduct this sequence of cumbersome operations in accordance with a prepared program.

In the twenty-third embodiment, the expander 735 expands the body cavity and protects the inner wall thereof, without performing a pneumoperitoneal operation. Further, the touch sensor 739 serves to protect the kidney 760 against damage. Automatically controlled, the micro-manipulators 738 and 770 scarcely contact any organ than the kidney 760. Should they be moved toward other organs, they are stopped by the expander 735. No force is applied onto the other organ while the surgical manipulator 701d is functioning.

As has been described, with the twenty-second and twenty-third embodiments it is possible to set the insertion section at a desired position, next to move the insertion section straight to a target object present in a body cavity, then to orientate the end effecter toward the object. As a result, the target object can be observed clearly or treated readily. Since the insertion section need not be bent in a complex manner, it does not damage any object other than the target one. Furthermore, since the end effecter is far shorter than the insertion section, it can treat the target object only and obtains an image of the target object only.

The 3D position sensor used in the embodiments described above will be explained, with reference to FIGS. 70A to 70E.

Figure 70A:
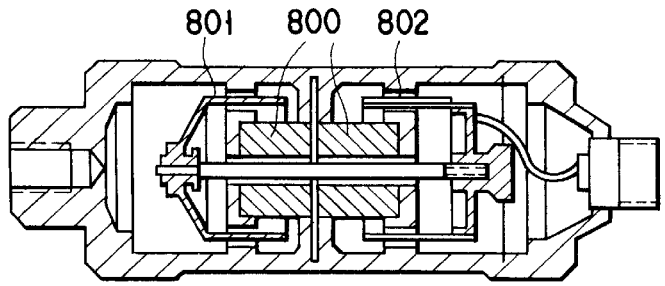
FIGS. 70A to 70D are diagrams showing various types of 3D position sensors.

FIG. 70A shows an electromotive pickup sensor which can be used as the 3D position sensor. This pickup sensor has a permanent magnet 800 and a pair of coils 801 and 802 sandwiching the magnet 800. The second coil 802 moves across the magnetic field of the magnet 800 and generates an electromotive force which is proportional to the speed at which it moves. The output of the pickup sensor is proportional to the speed of the coil 802. The first coil 801 is used to achieve electromagnetic braking. The coils 801 and 802 function as weights. The output of this pickup sensor must be electrically integrated to detect the position of an object. To detect a 3D position of the object, three electromotive pickup sensors need to be combined, with their detection axes a (i.e., detected vectors) intersect at right angles to one another as shown in FIG. 70D.

Figure 70B:
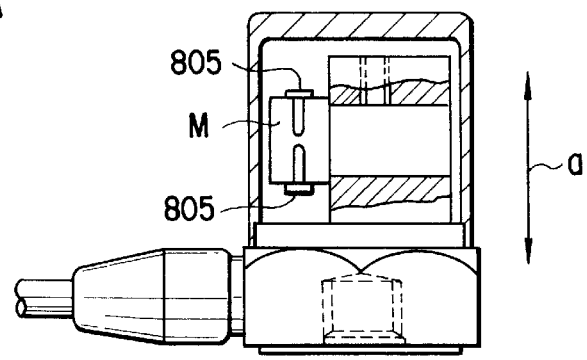

FIG. 70B shows a variable-resistance pickup sensor which can be used as the 3D position sensor. This sensor is designed to detect the strain on a strain gauge or a semiconductor strain gauge, in the form of a change in electrical resistance. More precisely, the sensor of FIG. 70B is an acceleration pickup which have four semiconductor gauges 805, one weight M and a DC bridge circuit. The DC bridge circuit detects the changes in the resistances of the gauges 805, which are proportional to the displacement of the weight M. The output of the DC bridge circuit, which is acceleration, must be electrically integrated twice in order to detect the position of an object. To detect a 3D position of the object, three variable-resistance pickup sensors need to be combined, with their detection axes a (i.e., detected vectors) intersecting at right angles to one another as shown in FIG. 70D.

Figure 70C:
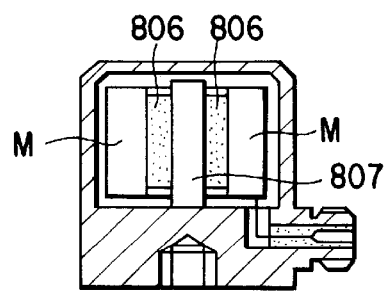
Figure 70D:
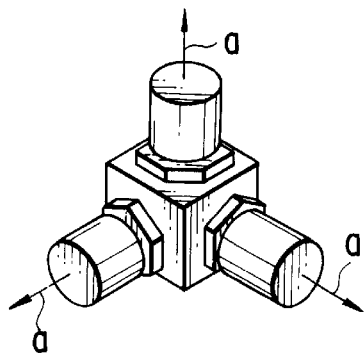

FIG. 70C shows a piezoelectric pickup sensor which can be used as the 3D position sensor, too. The piezoelectric pickup sensor has a hollow cylindrical weight M, a piezoelectric element 806 and a post 807. The element 806 is mounted on the post 807 and secured thereto. The weight M is secured to the upper and lower ends of the post 807, and concealing the piezoelectric element 806. When applied with a stress proportional to acceleration, the element 806 accumulates an electrical charge proportional to the stress. Thus, the charge corresponds to the acceleration. The output of the piezoelectric pickup sensor must be electrically integrated twice in order to detect the position of an object. To detect a 3D position of the object, three piezoelectric pickup sensors need to be combined, with their detection axes a (i.e., detected vectors) intersecting at right angles to one another as shown in FIG. 70D.

A servo acceleration pickup can be as the 3D position sensor, as well. This pickup sensor has a weight and a servo amplifier. The displacement of the weight is detected, and a current proportional to the displacement is fed back to the serve amplifier, thereby generating an electromotive force proportional to the displacement of the weight. The force is applied to the weight to sensor the position of the weight. The feedback current is proportional to the acceleration. The output of the servo acceleration pickup sensor must be electrically integrated twice in order to detect the position of an object. To detect a 3D position of the object, three servo acceleration pickup sensors need to be combined, with their detection axes a (i.e., detected vectors) intersecting at right angles to one another as shown in FIG. 70D.

Figure 70E:
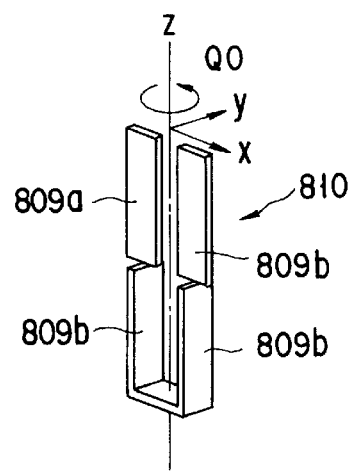
FIG. 70E is a diagram showing a gyroscope mechanism.
Figure 4:
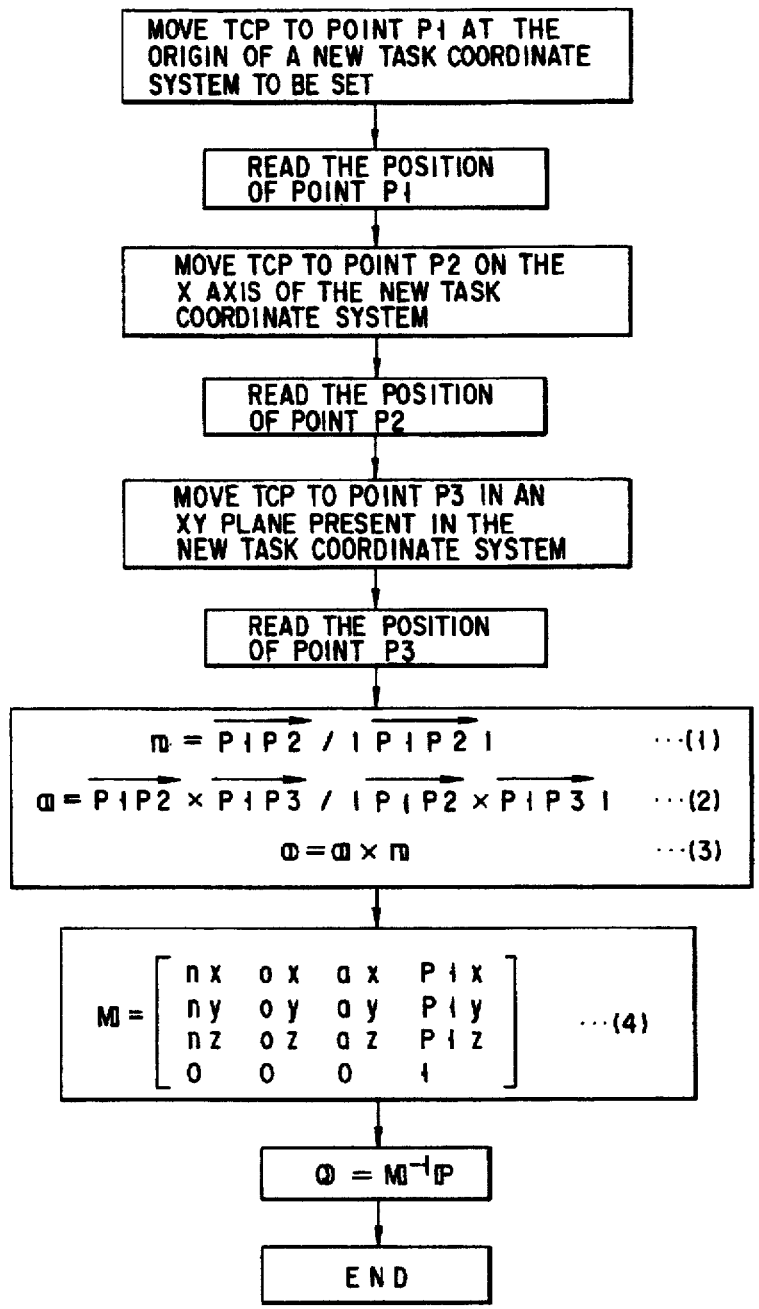

FIG. 70E shows an oscillation gyroscope which can be used as the 3D position sensor This sensor functions, utilizing the dynamic phenomenon that an oscillating object generates a Coriolis force when applied with an angular velocity. In other words, the sensor acts like the well-known Fourcault pendulum. As shown in FIG. 70E, a piezoelectric device 809 comprising a detecting element 809a and a driving element 809b is adhered to a tuning fork or an oscillator 810 shaped like a tuning fork. Angular velocity $Q_0$ is applied to the oscillator 810 which is oscillating. Then, the oscillator 810 generates Coriolis forces acting in the direction of oscillation (X axis) and in the direction (Y axis) perpendicular to the direction of oscillation. The element 809b extending in the Y axis detects the angular velocity $Q_0$. The angular velocity $Q_0$ is integrated, obtaining an angle. The oscillation gyroscope may be attached to the surgeon, for example, to his or her head, to detect the orientation of the head.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

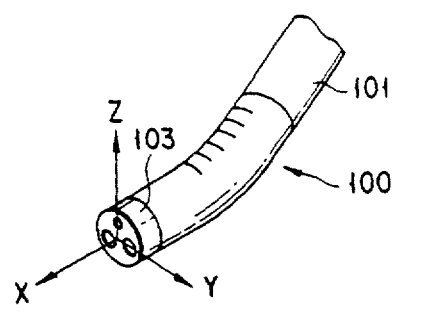
FIG. 19A
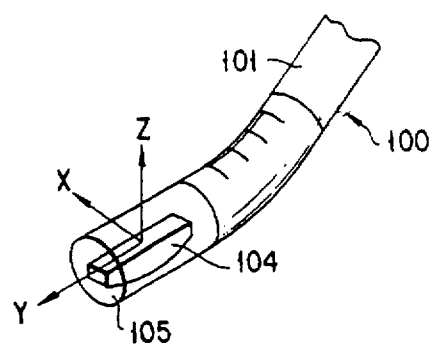
FIG. 19B
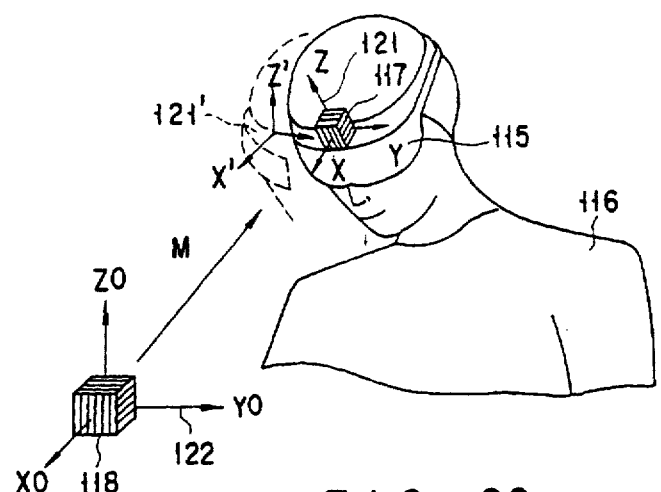
FIG. 20
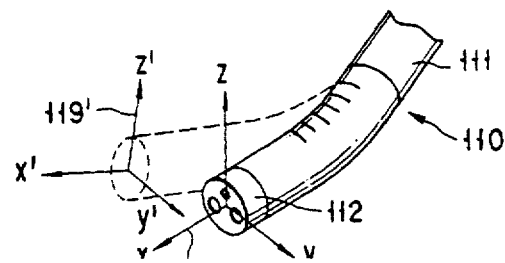

What is claimed is:

1. A surgical manipulator system comprising:

at least one surgical manipulator which holds a surgical device for performing a desired operation;

at least one operating means for controlling said surgical manipulator;

detecting means for detecting one of the following:
   (a) a geometrical relationship between said at least one surgical manipulator and said at least one operating means, and
   (b) a geometrical relationship between said at least one surgical manipulator and another surgical manipulator; and drive control means for controlling said at least one surgical manipulator in response to said operating means and said detecting means such that said surgical device performs a desired operation.

2. The system according to claim 1, wherein said detecting means comprises:

a first position detecting means for detecting at least one of a position and orientation of said at least one operating means by using a first base coordinate system as a reference;

a second position detecting means for detecting at least one of a position and orientation of said at least one surgical manipulator by using a second base coordinate system as a reference; and a coordinate-system conversion means for converting the coordinate system of one of said operating means and said surgical manipulator, to the coordinate system of the other of said operating means and said surgical manipulator, so as to operate said operating means and said surgical manipulator in a common coordinate system.

3. The system according to claim 2, wherein said second position detecting means includes a coordinate-system conversion means for converting the first base coordinate system to the second base coordinate system.

4. The system according to claim 1, wherein said surgical device is one selected from the group consisting of an endoscope, an ultrasonic echo probe, a surgical microscope, a holding forceps, a surgical knife, a suture applicator, a syringe, an ablation forceps, a needle-holding forceps and a clamp forceps.

5. The system according to claim 1, wherein said at least one operating means is one selected from the group consisting of a master manipulator, a three-dimensional position sensor, an eye-axis detector which designates a position on the line of the eye axis, a joystick, a speech recognition unit which designates a geometrical relationship to said at least one surgical manipulator and a gyroscope.

6. The system according to claim 1, wherein said at least one operating means includes two operating means, and wherein said system further comprises calculating means for calculating first tool center points corresponding to a first operating means and second tool center points corresponding to a second operating means, said calculating means determining a difference between the first and second tool center points in order to operate said surgical device.

7. The system according to claim 6, wherein one of said two operating means is a master manipulator, and the other of said two operating means is a head-mounted display.

8. The system according to claim 6, wherein said drive control means controls said at least one surgical manipulator only when said difference between the first and second tool center points is within a predetermined range.

9. The system according to claim 8, wherein said drive control means stops said at least one surgical manipulator only when said difference between the first and second tool center points is outside the predetermined range.

10. The system according to claim 1, wherein said at least one surgical manipulator includes first and second surgical manipulators, and said detecting means comprises a permanent magnet attached to said first surgical manipulator and a Hall element attached to said second surgical manipulator.

11. The system according to claim 10, wherein said first surgical manipulator has an endoscope.

12. The system according to claim 1, wherein said at least one surgical manipulator comprises:

a first manipulator unit which holds first surgical means for treating an affected part of a subject; and a second manipulator unit which holds a second surgical device for providing an image of the affected part;

wherein said at least one operating means comprises:

a master manipulator for operating said first manipulator unit; and a sensor for guiding said second manipulator unit;

wherein said surgical manipulator system further comprises display means for displaying the image provided by said second surgical device; and wherein said sensor is adapted to be secured to a surgeon's head, and said second manipulator unit is moved in the same way as said sensor.

13. The system according to claim 1, further comprising a joint mechanism for connecting said surgical device to said surgical manipulator, said joint mechanism having a free rotational axis and at least one degree of freedom.

14. The system according to claim 1, further comprising a fastener means for removably fastening said surgical manipulator to an operating table.

15. The system according to claim 1, wherein:

said surgical device comprises a straight insertion section and a surgical section which is connected to a distal end of the insertion section and which is able to bend to:

(a) treat an affected part of a subject and (b) provide an image of the affected part of the subject, and said surgical manipulator comprises a coupling device for holding said insertion section, while allowing said insertion section to move back and forth in a longitudinal direction of the insertion section, and a position device for positioning said insertion section.

16. The system according to claim 1, further comprising a connecting mechanism for removably connecting said surgical device to said surgical manipulator.

17. The system according to claim 16, further comprising an operation section for bending said surgical device, and coupling means for controlling a magnitude of a force to be transmitted from said operation section to said surgical device, such that said surgical device is flexed without restriction.

18. The system according to claim 1, further comprising an operation section for bending said surgical device, and coupling means for controlling a magnitude of a force to be transmitted from said operation section to said surgical device, such that said surgical device is flexed without restriction.

* * * * *

UNITED STATES PATENT AND TRADEMARK OFFICE
CERTIFICATE OF CORRECTION

PATENT NO. : 5,876,325
DATED : March 2, 1999
INVENTOR(S) : Mizuno et al.

Page 1 of 4

It is certified that error appears in the above-identified patent and that said Letters Patent is hereby corrected as shown below:

Drawings,
Replace the sheets of drawings containing
Figs 4-8, 10, 14, 18A, 18B, 20 and 67A with the sheets attached hereto.

Signed and Sealed this

Twenty-ninth Day of January, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 5,876,325
DATED : March 2, 1999
INVENTOR(S) : Mizuno et al.

It is certified that error appears in the above-identified patent and that said Letters Patent is hereby corrected as shown below:

Drawings,
Replace the sheets of drawings containing
Figs 4-8, 10, 14, 18A, 18B, 20 and 67A with the sheets attached hereto.

This certificate supersedes Certificate of Correction issued January 29, 2002.

Signed and Sealed this

Twelfth Day of March, 2002

Attest:

Attesting Officer

JAMES E. ROGAN
Director of the United States Patent and Trademark Office